(12) United States Patent
Suessmuth et al.

(10) Patent No.: US 11,225,465 B2
(45) Date of Patent: Jan. 18, 2022

(54) ALBICIDIN DERIVATIVES, THEIR USE AND SYNTHESIS

(71) Applicant: TECHNISCHE UNIVERSITÄT BERLIN, Berlin (DE)

(72) Inventors: Roderich Suessmuth, Berlin (DE); Dennis Kerwat, Berlin (DE); Stefan Graetz, Berlin (DE); Iraj Behroz, Berlin (DE); Leonard Von Eckardstein, Berlin (DE); Patrick Michael Durkin, Berlin (DE); Marius Morkunas, Berlin (DE); John Weston, Kelkheim (DE)

(73) Assignee: TECHNISCHE UNIVERSITÄT BERLIN, Berlin (DE)

( * ) Notice: Subject to any disclaimer, the term of this patent is extended or adjusted under 35 U.S.C. 154(b) by 40 days.

(21) Appl. No.: 16/631,737

(22) PCT Filed: Dec. 21, 2017

(86) PCT No.: PCT/EP2017/084120
§ 371 (c)(1),
(2) Date: Jan. 16, 2020

(87) PCT Pub. No.: WO2019/015794
PCT Pub. Date: Jan. 24, 2019

(65) Prior Publication Data
US 2020/0165214 A1    May 28, 2020

(30) Foreign Application Priority Data

Jul. 18, 2017 (DE) .................... 10 2017 212 264.1

(51) Int. Cl.
| | |
|---|---|
| C07C 229/02 | (2006.01) |
| C07C 235/64 | (2006.01) |
| C07C 255/28 | (2006.01) |
| C07D 211/34 | (2006.01) |
| C07D 211/66 | (2006.01) |
| C07D 213/56 | (2006.01) |
| C07D 229/02 | (2006.01) |
| C07D 233/64 | (2006.01) |
| C07D 233/90 | (2006.01) |
| C07D 249/04 | (2006.01) |
| C07D 265/30 | (2006.01) |
| C07D 295/15 | (2006.01) |
| A61P 31/04 | (2006.01) |

(52) U.S. Cl.
CPC ............ C07D 265/30 (2013.01); A61P 31/04 (2018.01); C07C 235/64 (2013.01); C07C 255/28 (2013.01); C07D 211/34 (2013.01); C07D 211/66 (2013.01); C07D 213/56 (2013.01); C07D 229/02 (2013.01); C07D 233/64 (2013.01); C07D 233/90 (2013.01); C07D 249/04 (2013.01)

(58) Field of Classification Search
CPC ..... A61P 31/04; C07C 229/02; C07C 235/64; C07C 255/28; C07D 211/34; C07D 211/66; C07D 213/56; C07D 229/02; C07D 233/64; C07D 233/90; C07D 249/04; C07D 265/30; C07D 295/15
See application file for complete search history.

(56) References Cited

U.S. PATENT DOCUMENTS

| | | |
|---|---|---|
| 4,525,354 A | 6/1985 | Birch et al. |
| 2017/0204052 A1 | 7/2017 | Kim et al. |

FOREIGN PATENT DOCUMENTS

| | | |
|---|---|---|
| WO | 2014/125075 A1 | 8/2014 |
| WO | 2015/003816 A2 | 1/2015 |
| WO | 2015/174747 A1 | 11/2015 |
| WO | 2016/082934 A1 | 6/2016 |

OTHER PUBLICATIONS

Grätz, S., et al., "Synthesis and Antimicrobial Activity of Albicidin Derivatives with Variations of the Central Cyanoalanine Building Block," ChemMedChem, vol. 11, No. 14, pp. 1499-1502 (Jun. 1, 2016).

Kretz J. et al., "Total Synthesis of Albicidin: A Lead Structure from *Xanthomonas albilineans* for Potent Antibacterial Gyrase Inhibitors," Angewandte Chemie International Edition in English, vol. 54, No. 6, pp. 1969-1973 (2015).

Vieweg, L. et al. "The Albicidin Resistance Factor AlbD is a Serine Endopeptidase That Hydrolyzes Unusual Oligoaromatic-Type Peptides," Journal of the American Chemical Society, vol. 137, No. 24, pp. 7608-7611 (Jun. 9, 2015).

*Primary Examiner* — Laura L Stockton
(74) *Attorney, Agent, or Firm* — Maschoff Brennan

(57) ABSTRACT

A chemical compound is provided according to general formula (1):

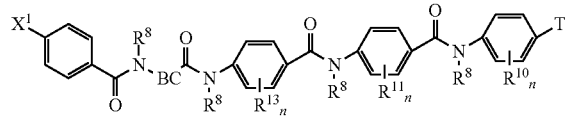

Formula 1

20 Claims, No Drawings

ALBICIDIN DERIVATIVES, THEIR USE AND SYNTHESIS

CROSS-REFERENCE TO A RELATED APPLICATION

This application is a National Phase Patent Application of International Patent Application Number PCT/EP2017/084120, filed on Dec. 21, 2017, which claims priority of German Patent Application Number 102017212264.1, filed on Jul. 18, 2017.

BACKGROUND

The disclosure relates to albicidin derivatives.

Albicidin is a natural product, isolated from *Xanthomonas albilineans* and heterologously expressed in *Xanthomonas axonopodis* pv *vesicatoria*. Its structure (see below) is based on peptides and amino acids, but it does not contain any proteinogenic amino acids.

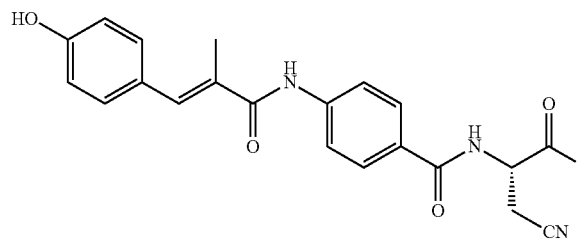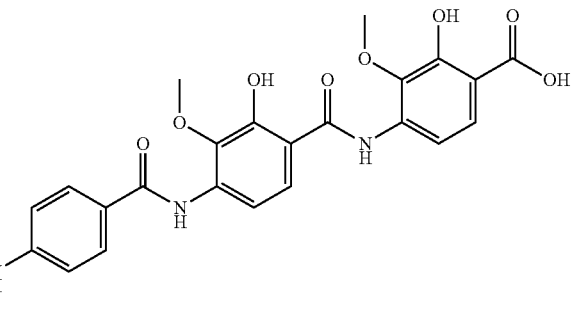

Albicidin is, on the one hand, a causative agent of the leaf scald disease in sugar cane and on the other hand a DNA-gyrase-inhibitor of prokaryotic cells (gram-positive and -negative). The mentioned properties make the natural product albicidin a potential antibiotic.

The known molecular structure of albicidin and available synthetic routes allows the development of a plurality of novel derivatives that may exhibit potential antimicrobial activities.

SUMMARY

The problem underlying the proposed solution is the provision of new compounds, which comprise antibiotic properties, a method of their synthesis and their use.

This problem is attained by the compounds as described herein.

Terms and Definitions

The term "purity" as used in the context of the present specification with respect to a preparation of a certain compound refers to the content of said compound relative to the sum of all compounds contained in the preparation. The term "compound" in this context is to be understood as a compound according to the general formula 1 (or any specific embodiments thereof) as well as any salts, hydrates or solvates thereof. Thus, the respective salts, hydrates or solvates are not considered as impurities according to the previous definition. The "purity" of a compound may be determined using elemental analysis, HPLC analysis using UV diode array detection also in combination with mass spectrometry detection, or quantitative NMR analysis.

The term "substituted" refers to the addition of a substituent group to a parent moiety. "Substituent groups" can be protected or unprotected and can be added to one available site or to many available sites in a parent moiety. Substituent groups may also be further substituted with other substituent groups and may be attached directly or by a linking group such as an alkyl, an amide or hydrocarbyl group to a parent moiety. "Substituent groups" amenable herein include, without limitation, halogen, subst. oxygen, subst. nitrogen, subst. sulphur, hydroxyl, alkyl, alkenyl, alkynyl, acyl (—C(O)R$^a$), carboxyl (—C(O)OR$^a$), aliphatic groups, alicyclic groups, alkoxy, substituted oxy (—OR$^a$), aryl, aralkyl, heterocyclic radical, heteroaryl, heteroarylalkyl, amino (—N(R$^b$)(R$^c$)), imino(=NR$^b$), amido (—C(O)N(R$^b$)(R$^c$) or —N(R$^b$)C(O)R$^a$), hydrazine derivates —NR$^a$NR$^b$R$^c$, tetrazolyl (CN$_4$H$_1$), azido (—N$_3$), nitro (—NO$_2$), cyano (—CN), isocyano (—NC), cyanato (—OCN), isocyanato (—NCO), thiocyanato (—SCN); isothio-cyanato (—NCS); carbamido (—OC(O)N(R$^b$)(R$^c$) or —N(R$^b$)C(O)OR$^a$), substituted thio (—SR$^b$), sulfinyl (—S(O)R$^b$), sulfonyl (—S(O)$_2$R$^b$), sulfonamidyl (—S(O)$_2$N(R$^b$)(R$^c$) or —N(R$^b$)S(O)$_2$R$^b$) and fluorinated groups such as —CH$_2$CF$_3$, —CHFCF$_3$, —CF$_2$CF$_3$, —CHF$_2$, —CH$_2$F, —CF$_3$, —OCF$_3$, —SCF$_3$, —SOCF$_3$ or —SO$_2$CF$_3$. Wherein each R$^a$, R$^b$ and R$^c$ is, independently, H or a further substituent group with a preferred list including without limitation, H, alkyl, alkenyl, alkynyl, cycloalkyl, alkoxy, acyl, aryl, heteroaryl, alicyclyl, heterocyclyl and heteroarylalkyl.

As used herein the term "alkyl," refers to a saturated straight or branched hydrocarbon moiety containing up to 8, particularly up to 4 carbon atoms. Examples of alkyl groups include, without limitation, methyl, ethyl, propyl, butyl, isopropyl, n-hexyl, octyl, and the like. Alkyl groups typically include from 1 to about 8 carbon atoms (C$_1$-C$_8$ alkyl), particularly with from 1 to about 4 carbon atoms (C$_1$-C$_4$ alkyl).

As used herein the term "cycloalkyl" refers to an interconnected alkyl group forming a saturated or unsaturated ring (whereby an unsaturated cycle can also be defined as "cycloalkenyl") or polyring structure containing 3 to 10, particularly 5 to 10 carbon atoms. Examples of cycloalkyl groups include, without limitation, cyclopropyl, cyclopentyl, cyclohexyl, norbornyl, decalinyl or adamantyl (derived from tricyclo[3.3.1.1]decane), and the like. Cycloalkyl groups typically include from 5 to 10 carbon atoms (C$_5$-C$_{10}$ cycloalkyl).

Alkyl or cycloalkyl groups as used herein may optionally include further substituent groups. A substitution on the cycloalkyl group also encompasses an aryl, a heterocyclyl or a heteroaryl substituent, which can be connected to the cycloalkyl group via one atom or two atoms of the cycloalkyl group (like tetraline).

As used herein the term "haloalkyl," refers to a saturated straight or branched hydrocarbon moiety containing 1 to 8, particularly 1 to 4, carbon atoms and at least one halogen atom, in particular Cl or F, connected to a carbon atom. Examples of haloalkyl groups include, without limitation, $CF_3$, $CHF_2$, $CH_2F$, $CH_2CF_3$, $CH_2CHF_2$, $CH_2CH_2F$, $CHFCF_3$, $CHFCHF_2$, $CHFCH_2F$, $CF_2CF_3$, $CF_2CHF_2$, $CF_2CH_2F$ and the like. Haloalkyl groups typically include 1 to 4 carbon atoms ($C_1$-$C_4$ haloalkyl). More particularly haloalkyl groups comprise only F as halogen atoms.

As used herein the term "halo cycloalkyl" refers to an interconnected alkyl group forming a saturated or unsaturated ring or polyring structure containing 3 to 10, particularly 5 to 10 carbon atoms and at least one halogen atom, in particular Cl or F, connected to a carbon atom. Examples of halo cycloalkyl groups include, without limitation, fluorocyclopropyl, chlorocyclohexyl, dichlorocyclohexyl, chloroadamantyl, and the like. Halo cycloalkyl groups typically include from 5 to 10 carbon atoms ($C_5$-$C_{10}$ cycloalkyl). More particularly cyclohaloalkyl groups comprise only F as halogen atoms.

Halo alkyl or halo cycloalkyl groups as used herein may optionally include further substituent groups. A substitution on the halo cycloalkyl group also encompasses an aryl, a heterocyclyl or a heteroaryl substituent, which can be connected to the halo cycloalkyl group via one atom or two atoms of the halo cycloalkyl group (like tetraline).

As used herein the term "alkenyl," refers to a straight or branched hydrocarbon chain moiety containing up to 8 carbon atoms and having at least one carbon-carbon double bond. Examples of alkenyl groups include, without limitation, ethenyl, propenyl, butenyl, 1-methyl-2-buten-1-yl, dienyl groups such as 1,3-butadienyl and the like. Alkenyl groups typically include from 2 to about 8 carbon atoms, more typically from 2 to about 4 carbon atoms. Alkenyl groups as used herein may optionally include further substituent groups.

As used herein the term "alkynyl," refers to a straight or branched hydrocarbon moiety containing up to 8 carbon atoms and having at least one carbon-carbon triple bond. Examples of alkynyl groups include, without limitation, ethynyl, 1-propynyl, 1-butynyl, and the like. Alkynyl groups typically include from 2 to about 8 carbon atoms, more typically from 2 to about 4 carbon atoms. Alkynyl groups as used herein may optionally include further substituent groups.

As used herein the term "carboxy," refers to an carboxy (—C(=O)—O— or —O—C(=O)—) alkyl moiety containing 1 to 8, particularly 1 to 4 carbon atoms comprising at least one carboxy moiety, wherein the carboxy group is used to attach the carboxy group to a parent molecule. Examples of carboxy groups include without limitation, formate, acetate, lactate, citrate, oxalate and the like. Carboxy groups as used herein may optionally include further substituent groups. In particular "carboxy" groups include straight or branched polycarboxy groups (polyester), which comprise several interconnected monomeric carboxy groups (e. g. —C(=O)—O—$CH_2$—$CH_2$—). Non limiting examples are polyethylester or polyacrylate.

As used herein the term "alkoxy," refers to an oxygen alkyl moiety containing 1 to 8, particularly 1 to 4 carbon atoms comprising at least one oxygen moiety, wherein the oxygen atom is used to attach the alkoxy group to a parent molecule. Examples of alkoxy groups include without limitation, methoxy, ethoxy, n-propoxy, isopropoxy, n-butoxy, sec-butoxy, tert-butoxy, n-pentoxy, neopentoxy, n-hexyloxy and the like. Alkoxy groups as used herein may optionally include further substituent groups. In particular "alkoxy" groups include straight or branched polyalkoxy groups (polyether), which comprise several interconnected monomer alkoxy groups (e. g. —O—$CH_2$—$CH_2$—). Non limiting examples are groups derived from polyethyleneglycol (PEG) or polypropylenglycol (PPG).

As used herein the term "heterocyclyl" refers to an interconnected alkyl group forming a saturated or unsaturated ring or polyring structure containing 3 to 10, particularly 5 to 10 carbon atoms in which at least one carbon atom is replaced with an oxygen, a nitrogen or a sulphur atom forming a non-aromatic structure. Examples of heterocyclyl groups include, without limitation, oxalanyl, pyrrolidinyl or piperidinyl. Heterocyclic groups as used herein may optionally include further substituent groups. A substitution on the heterocyclic group also encompasses an aryl, a cycloalkyl or a heteroaryl substituent, which can be connected to the heterocyclic group via one atom or two atoms of the heterocyclic group (comparable to indole or indoline).

As used herein the term "aryl" refers to a hydrocarbon with alternating double and single bonds between the carbon atoms forming an aromatic ring structure, in particular a six ($C_6$) to ten ($C_{10}$) membered ring or polyring structure. The term "heteroaryl" refers to aromatic structures comprising a five to ten membered ring or polyring structure, comparable to aryl compounds, in which at least one member is an oxygen or a nitrogen or a sulphur atom. Due to simplicity reasons they are denominated $C_5$ to $C_{10}$ heteroaryl, wherein at least one carbon atom is replaced with an oxygen, a nitrogen or a sulphur atom forming an aromatic structure. For example a $C_5$ heteroaryl comprises a five membered ring structure with at least one carbon atom being replaced with an oxygen, a nitrogen or a sulphur atom. Examples for such a $C_5$ heteroaryl are triazolyl, pyrazolyl, imidazolyl, thiophenyl, furanyl or oxazolyl. A $C_6$ heteroaryl can be pyridyl, pyrimidinyl or triazinyl. A $C_9$ heteroaryl can be indolyl and a $C_{10}$ heteroaryl can be quinolinyl. Aryl or hetero aryl groups as used herein may optionally include further substituent groups. A substitution on the hetero aryl group also encompasses an aryl, a cycloalkyl or a heterocyclyl substituent, which can be connected to the hetero aryl via one atom or two atoms of the hetero aryl group (comparable to indole). The same applies to an aryl group.

As used herein "*" indicates a stereo center of a L- or D-enantiomer, which is located on the tertiary carbon atom below the asterisk *, and wherein the compound of a general formula comprising "*" is an essentially pure L-enantiomer, an essentially pure D-enantiomer or a mixture of the L- and D-enantiomer of the same molecular formula, wherein in particular such a compound is an essentially pure L-enantiomer or an essentially pure D-enantiomer.

DESCRIPTION OF THE SOLUTION

According to a first aspect, the solution relates to compounds having a molecular structure as defined by formula (1)

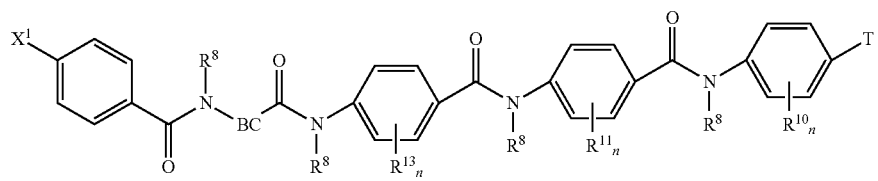

a) with BC being selected from

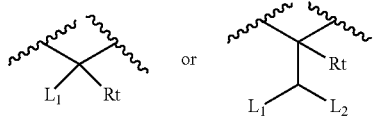

with $L_1$ being a substituted or unsubstituted aromatic heterocycle or a substituted or unsubstituted non-aromatic heterocycle, or —$NHR^d$ or —$NR^d_2$;

with Rt being selected from H or $C_1$-$C_4$ alkyl, with $L_1$ and Rt forming a non-aromatic heterocycle, in particular a N-heterocyclic ring, which is optionally substituted, with $L_2$ being selected from —H, —OH, —$OR^d$, and substituted or unsubstituted —$C_1$-$C_4$ alkyl, $C_1$-$C_6$ alkoxycarbonyl and $C_1$-$C_6$ alkylaminocarbonyl, with $R^d$ being selected from a substituted or unsubstituted $C_1$-$C_{16}$ alkyl, a substituted or unsubstituted $C_2$-$C_{16}$ alkenyl, in particular a substituted or unsubstituted $C_1$-$C_8$ alkyl, a substituted or unsubstituted $C_2$-$C_8$ alkenyl, a substituted or unsubstituted $C_3$-$C_{10}$ cycloalkyl, and all moieties optionally substituted with F, b) with $X^1$ being BA-$CONR^8$— with BA being selected from

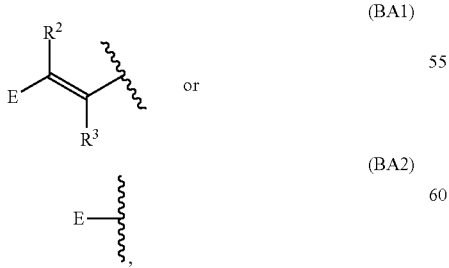

with $R^2$ and $R^3$ being selected, where applicable, independently from each other from —H, —F, —CN, —OH, a substituted or unsubstituted $C_1$-$C_3$ alkyl, a substituted or unsubstituted $C_1$-$C_3$ alkoxy or a $C_1$-$C_3$ haloalkyl, in particular with $R^2$ and $R^3$ being selected, where applicable, independently from each other from —H, —F, —CN, —OH, —$CH_3$, —$CH_2CH_3$, —$OCH_3$, —$OCH_2CH_3$, —$OCH_2CH_2CH_3$, —$OCH(CH_3)_2$, —$OCF_3$, —$CH_2CF_3$, —$CHFCF_3$, —$CF_2CF_3$, —$CHF_2$, —$CH_2F$ or —$CF_3$, more particularly with $R^2$ and $R^3$ being selected independently from each other from —H, —F, —$OCH_3$ or —$CH_3$, with the double being a Z or E-double bond;

with E being a substituted or unsubstituted $C_1$-$C_{16}$ alkyl, a substituted or unsubstituted $C_2$-$C_{16}$ alkenyl, a substituted or unsubstituted $C_2$-$C_{16}$ alkynyl, in particular a substituted or unsubstituted $C_1$-$C_8$ alkyl, a substituted or unsubstituted $C_2$-$C_8$ alkenyl, a substituted or unsubstituted $C_2$-$C_8$ alkynyl, a substituted or unsubstituted $C_3$-$C_{10}$ cycloalkyl, a substituted or unsubstituted $C_3$-$C_{10}$ heterocycle; in particular a substituted or unsubstituted $C_4$-$C_{10}$ heterocycle a substituted or unsubstituted $C_5$-$C_{10}$ heteroaryl, a substituted or unsubstituted $C_6$-$C_{10}$ aryl, wherein at least one optional substituent may be in particular aryl, alkoxy, hydroxy or halogen; such as fluor;

c) with each $R^8$ being —H, or $C_1$-$C_4$ alkyl, optionally substituted with one or more F, in particular with each $R^8$ being selected independently from each other from H or $CH_3$, more particularly $R^8$ being H, and d) with n of $R^{10}_n$ and n of $R^{11}_n$ being independently from each other 0, 1, 2, 3 or 4, in particular n of $R^{10}_n$ and n of $R^{11}_n$ being 0, 1, 2 or 3, and with each $R^{10}$ and $R^{11}$ being selected independently from any other $R^{10}$ and $R^{11}$ from —OH, —F, —Cl, —Br, —I, —CCH, —CN, —$N_3$, —$OC_1$-$C_6$ alkyl, optionally substituted with OH or F, such as, —$OCF_3$, —$NH_2$, —$NHCH_3$, —$N(CH_3)_2$, —$C_1$-$C_6$ alkyl, in particular —$CH_3$ or —$CH_2CH_3$, —$(CH_2)_m$-$OR_a$, —$CHCH_2$, —$CH_2OH$, —$SO_2NH_2$, —$SO_2N(CH_3)_2$, —$SO_2NHCH_3$, —$CH_3$, —$CF_3$ or —$NO_2$, —O—$PO_3H_2$, —O—$PO_3R_aH$ or —O—$PO_3R_{a2}$, in particular from —OH, —F, —$OCH_3$, —$OC_2H_5$, —$OiC_3H_7$, —$OnC_3H_7$, —$OCF_3$ or —$CF_3$, with $R_a$ being selected from
hydrogen,
a substituted or unsubstituted $C_1$-$C_{16}$ alkyl, a substituted or unsubstituted $C_2$-$C_{16}$ alkenyl, a substituted or unsubstituted $C_2$-$C_{16}$ alkynyl, or a $C_1$-$C_{16}$ haloalkyl, or
a substituted or unsubstituted $C_3$-$C_{10}$ cycloalkyl or a substituted or unsubstituted $C_3$-$C_{10}$ halo cycloalkyl;
with m being selected from 0, 1 or 2, in particular 0 or 1,
e) with T being selected from —$CO_2H$, —$SO_3H$, —C(=O)$OR_a$ or —CON($R_a$)$_2$ with $R_a$ having the above meaning, wherein in case of —CON($R_a$)$_2$ $R_a$ can be the same or different;
f) with n of $R^{13}{}_n$ being 0, 1, 2, 3 or 4, in particular n of $R^{13}{}_n$ being 0, 1, 2 or 3, and
with each $R^{13}$ being selected independently from any other $R^{13}$ from —OH, substituted or unsubstituted —$C_1$-$C_6$ alkyl, substituted or unsubstituted $C_1$-$C_6$ alkoxy or fluoro, in particular —OH or —$OCH_3$.

It is to be understood that with Rt and $L_1$, $L_2$ there could be two chiral centers here (providing $L_1$ and $L_2$ are not the same). Thus diastereoisomers are possible in addition to enantiomers.

In one embodiment of the present compound according to formula (1) the moiety $L_1$ is a five membered or six membered aromatic heterocycle or 3-7 membered non-aromatic heterocycle, preferably a five membered or six membered aromatic N-heterocycle or non-aromatic N heterocycle that may be substituted or unsubstituted.

In specific embodiments the moiety $L_1$ is a five membered aromatic N-heterocycle selected from a group comprising substituted or unsubstituted pyrroles, imidazoles, pyrazoles, triazoles, tetrazoles;
pyrazolone, preferably 3H-pyrazol-3-ones, 4H-pyrazol-4-ones, 1,2-dihydro-3H-pyrazol-3-ones, 2,4-dihydro-3H-pyrazol-3-ones, triazolones, preferably 1,2,4-triazol-3-one, imidazolones, pyrrolidones,
thiadiazoles, preferably 1,3,4-thiadiazoles, thiazoles, isothiazoles, thiazolidinediones; and
isoxazoles, oxazoles, oxadiazoles (1,3,4-oxadiazoles, 1,2,4-oxadiazoles).

In one variant moiety $L_1$ may not be —$CH_2(C_3H_3N_2)$ (imidazole).

The aromatic five membered heterocycles may be preferably substituted by a $C_1$-$C_6$ alkyl moiety, most preferably by a methyl or ethyl moiety. It is most preferred, if the N atom is substituted by a $C_1$-$C_6$ alkyl moiety, most preferably by a methyl or ethyl moiety.

In further embodiments of the present compound of formula (1) the moiety $L_1$ is a five membered non-aromatic N-heterocycle selected from a group comprising substituted or unsubstituted pyrrolidines, pyrazolidines,
hydantoines, imidazolidinones (imidazolidin-4-one), isoxazolidines, oxazolidinones (1,3,-oxazolidin-2-one);
isothiazolidines, isothiazolinone.

In yet further embodiments the moiety $L_1$ is a six membered aromatic N-heterocycle selected from a group comprising substituted or unsubstituted pyridines, pyridazines, pyrimidines, pyrazines, triazines and tetrazines.

In still another embodiment of the present compound of formula (1) the moiety $L_1$ is a six membered non-aromatic N heterocycle selected from a group comprising substituted or unsubstituted piperidines and piperazines or morpholines.

The non-aromatic 5 and 6 membered heterocyles may be preferably substituted by a $C_1$-$C_6$ alkyl moiety, most preferably by a methyl or ethyl moiety. It is most preferred, if the N atom is substituted by a $C_1$-$C_6$ alkyl moiety, most preferably by a methyl or ethyl moiety. For example, a suitable substituted N-heterocycle may be N-methyl piperidine.

In still another embodiment of the present compound of formula (1) the moiety $L_1$ is —$NHR^d$ or —$NR^d{}_2$ wherein Rd is a methyl or ethyl moiety.

The moiety $L_2$ may be selected from —H, —OH, —$OR^d$, and —$CH_3$, —$C_2H_6$ or —$C_3H_7$, with $R^d$ being substituted or unsubstituted $C_1$-$C_5$ alkyl, preferably a $C_1$-$C_3$ alkyl.

In a preferred embodiment the present compound may be of the general formulae (2)

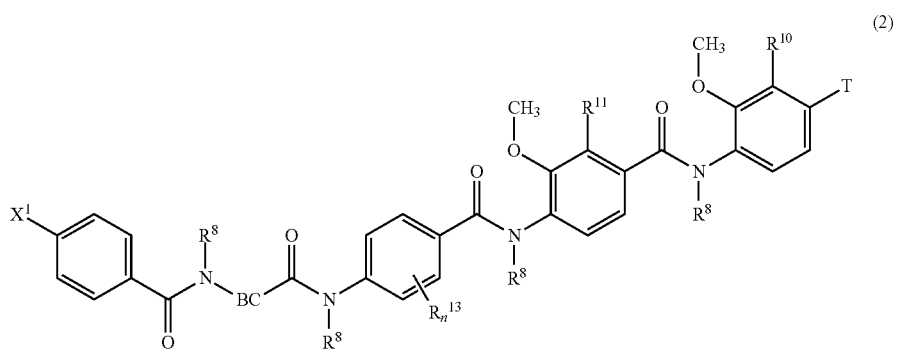

(2)

wherein $X^1$, BC, $R^8$, $R^{11}$, $R^{10}$, $R^{13}$ and T have the above meaning.

In another preferred embodiment the present compound may be of general formula (3)

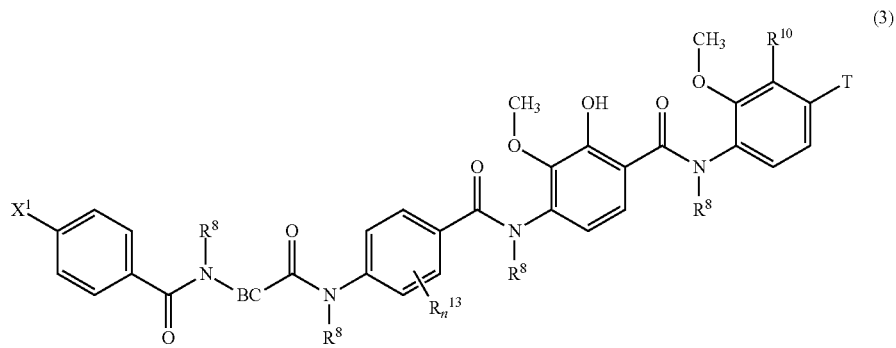

(3)

wherein $X^1$, BC, $R^8$, $R^{13}$ and T have the above meaning.

In another preferred embodiment the present compound may be of general formula (4a)

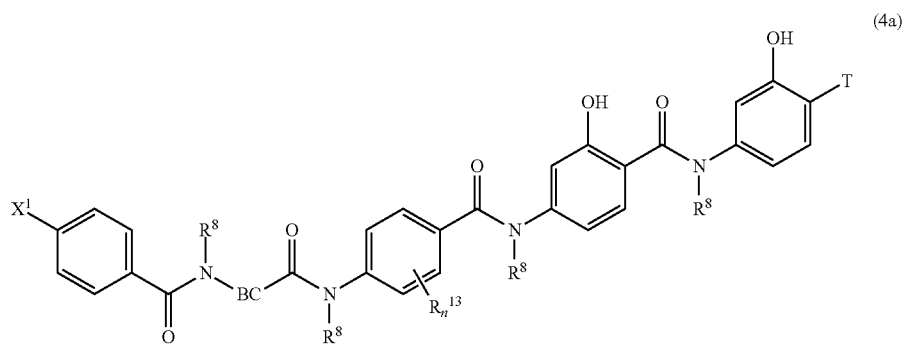

(4a)

wherein $X^1$, BC, $R^8$, $R^{13}$ and T have the above meaning.

In another preferred embodiment the present compound may be of general formula (4b)

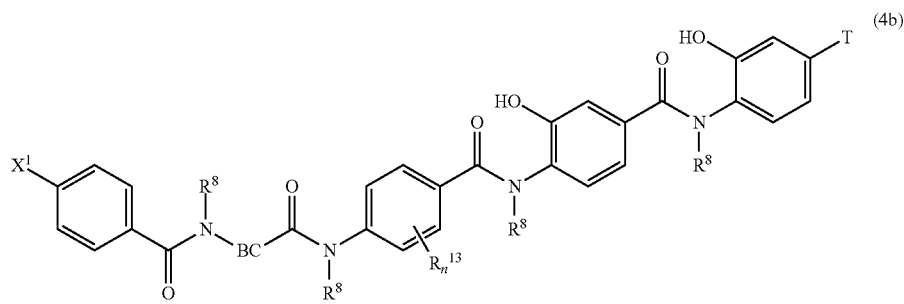

(4b)

wherein $X^1$, BC, $R^8$, $R^{13}$ and T have the above meaning.

In yet another preferred embodiment the present compound may be of general formula (4c)

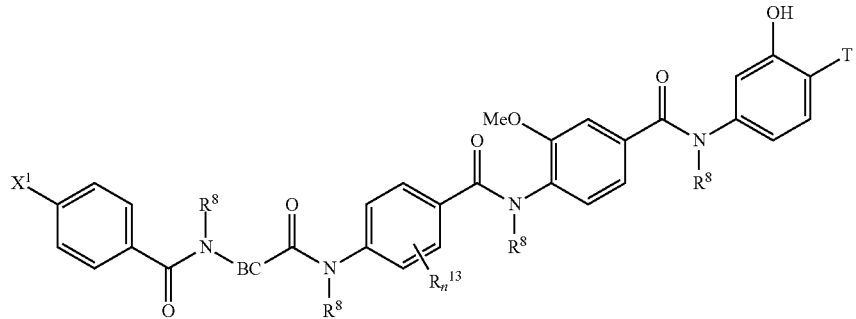

(20)

wherein $X^1$, BC, $R^8$, $R^{13}$ and T have the above meaning.

In another preferred embodiment the present compound may be of general formula (5)

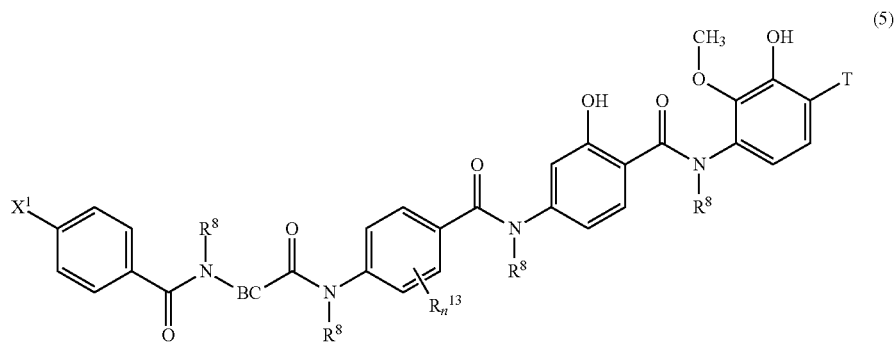

(5)

wherein $X^1$, BC, $R^8$, $R^{13}$ and T have the above meaning.

In another preferred embodiment the present compound may be of general formula (6)

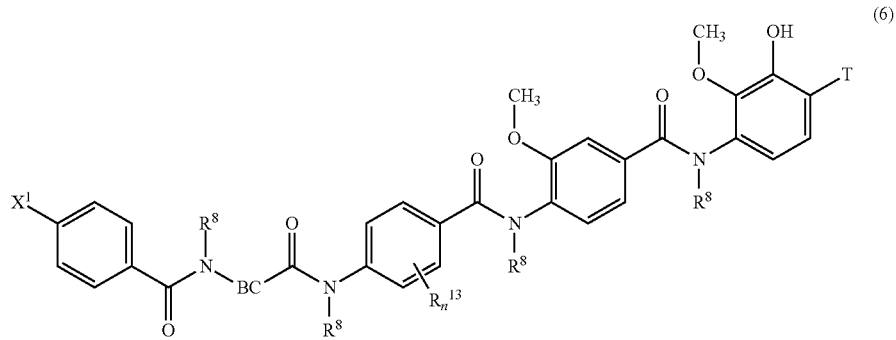

(6)

wherein $X^1$, BC, $R^8$, $R^{13}$ and T have the above meaning.

In another preferred embodiment the present compound may be of general formula (7)

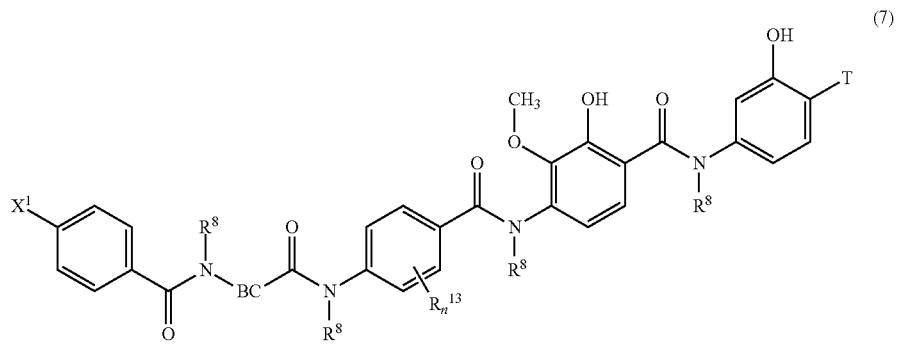

(7)

wherein $X^1$, BC, $R^8$, $R^{13}$ and T have the above meaning.

In another preferred embodiment the present compound may be of general formula (8)

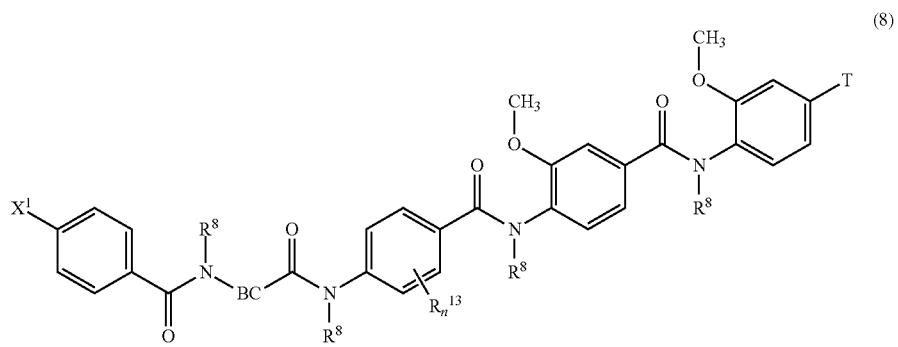

(8)

wherein $X^1$, BC, $R^8$, $R^{13}$ and T have the above meaning.

In another embodiment of the present compounds of general formula (1) and (2) the moiety $X^1$ is BA-CONHR$^8$—, with BA being BA1, with $R^2$ and $R^3$ having the same meaning as defined previously, and
with E being

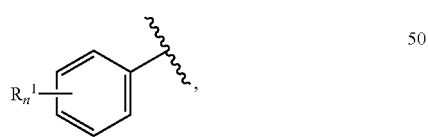

with n of $R^1_n$ being 0, 1, 2, 3, 4 or 5, in particular n of $R^1_n$ being 0, 1, 2 or 3, more particularly n of $R^1_n$ being 1, and
with each $R^1$ independently from any other $R^1$ being selected from —OH, —F, —Cl, —Br, I, —CCH, —CN, —N$_3$, —OCH$_3$, —OC$_2$H$_5$, —OC$_3$H$_7$, in particular —OiPr, —OCF$_3$, —OCHCCH, —NH$_2$, —NHCH$_3$, —N(CH$_3$)$_2$, —CH$_3$, —CH$_2$—CH$_3$, —CF$_3$, —OCONH$_2$, —NO$_2$, —OCH$_2$O—, —O—PO$_3$H$_2$, —O—PO$_3$RaH —O—PO$_3$Ra$_2$ or —(CH$_2$)$_m$—OR$_a$, with m and R$_a$ having the above meaning. $R^1$ is preferably —OH, —OCHCCH, —OCH$_3$, —OC$_2$H$_5$, —F, most preferably —F, —OH and —OCHCCH.

In another embodiment of the present compounds of general formula (1) and (2) the moiety $X^1$ is BA-CONHR$^8$—, with BA being BA2, with E being a substituted or unsubstituted $C_1$-$C_8$ alkyl, a substituted or unsubstituted $C_2$-$C_8$ alkenyl, a substituted or unsubstituted $C_2$-$C_8$ alkynyl, a substituted or unsubstituted $C_3$-$C_{10}$ cycloalkyl,
a substituted or unsubstituted $C_4$-$C_{10}$ heterocycle
a substituted or unsubstituted $C_5$-$C_{10}$ heteroaryl,
wherein at least one optional substituent may be in particular aryl, phenyl, methoxyphenyl or halogen; such as fluor;
or with E being

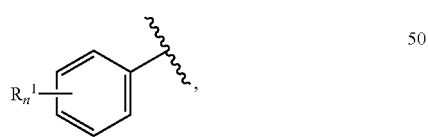

with n of $R^1_n$ being 0, 1, 2, 3, 4 or 5, in particular n of $R^1_n$ being 0, 1, 2 or 3, more particularly n of $R^1_n$ being 1, and
with each $R^1$ independently from any other $R^1$ being selected from —OH, —F, —Cl, —Br, I, —CCH, —CN, —N$_3$, —OCH$_3$, —OC$_2$H$_5$, —OC$_3$H$_7$, in particular —OiPr, —OCF$_3$, —OCHCCH, —NH$_2$, —NHCH$_3$, —N(CH$_3$)$_2$, —CH$_3$, —CH$_2$—CH$_3$, —CF$_3$, —OCONH$_2$, —NO$_2$, —OCH$_2$)—, —O—PO$_3$H$_2$, —O—PO$_3$RaH —O—PO$_3$Ra$_2$ or —(CH$_2$)$_m$—OR$_a$, with m and $R_a$ having the above meaning. $R^1$ is preferably —OH, —OCHCCH, —OCH$_3$, —OC$_2$H$_5$, —F most preferably —OH.

In some embodiments, $X^1$ is selected from

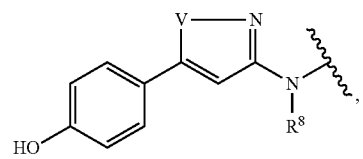

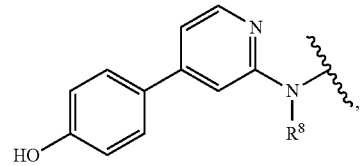

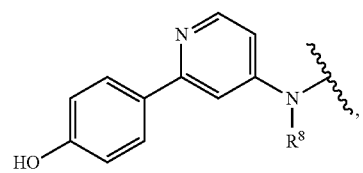

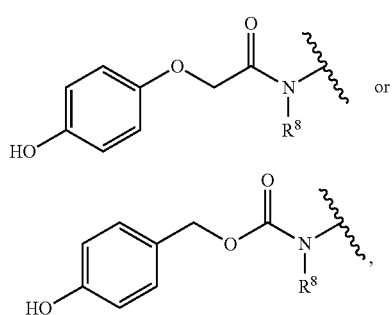

with $R^8$ being selected from H or CH$_3$, in particular $R^8$ is H and with V being selected from O, NH or S, in particular from O or NH.

In some embodiments, $X^1$ is selected from

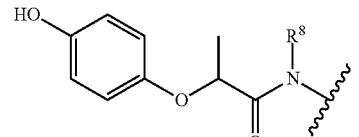

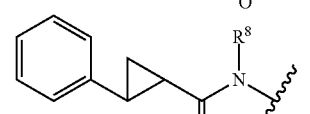

or

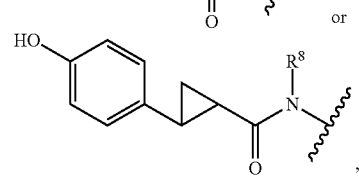

with $R^8$ being selected from H or CH$_3$, in particular $R^8$ is H. It is to be understood that all possible optical isomers may be covered.

In some embodiments, $X^1$ is selected from

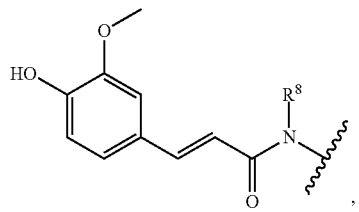

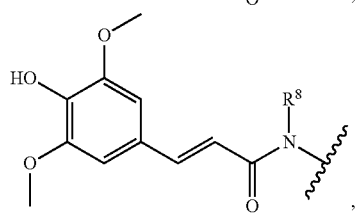

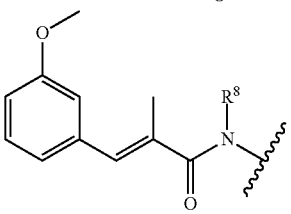

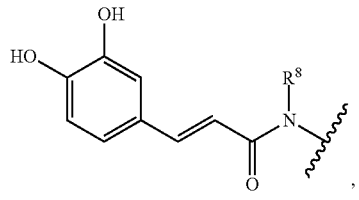

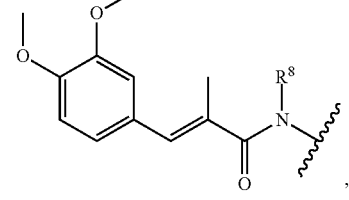

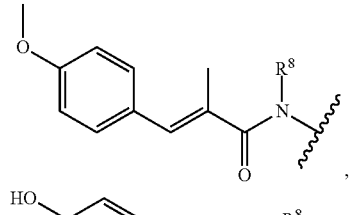

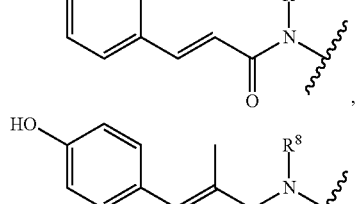

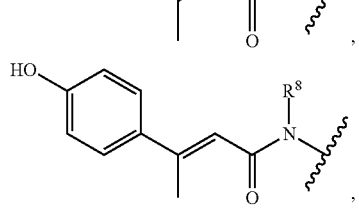

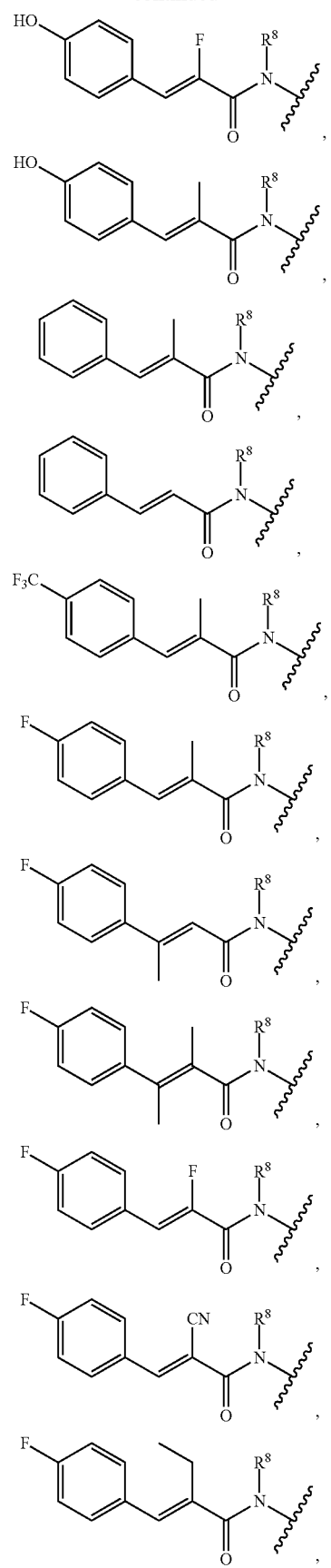
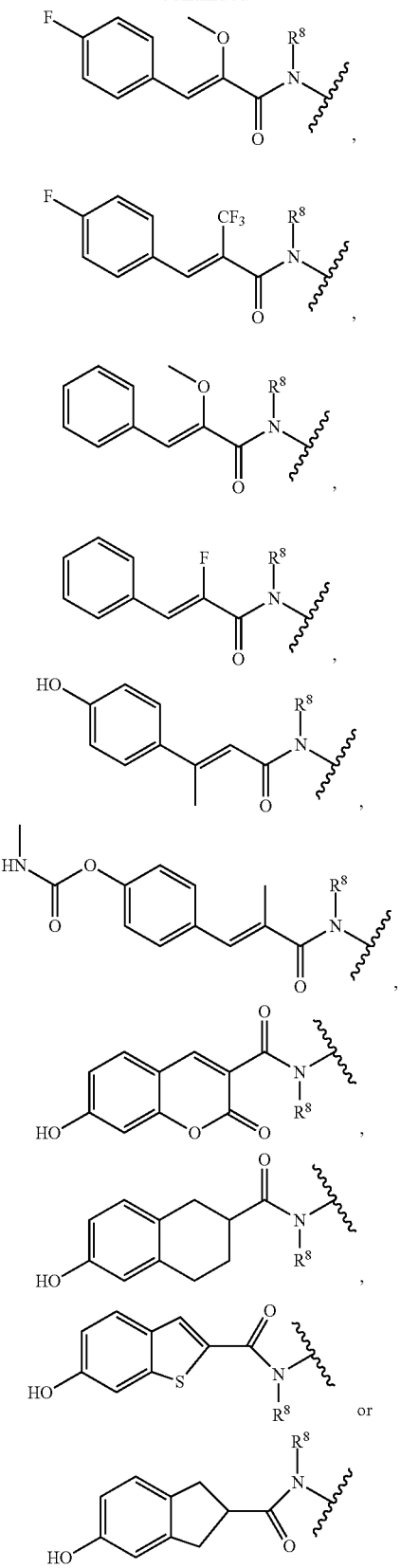
with $R^8$ being selected from H or $CH_3$, in particular $R^8$ is H.

In a more preferred embodiment $X^1$ is

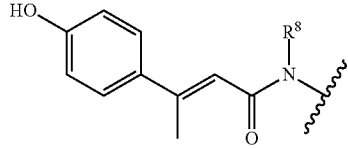

with $R^8$ being H.

In another preferred embodiment of the present compound n of $R^{10}{}_n$ and n of $R^{11}{}_n$ is 0, 1, 2, 3 or 4, in particular n of $R^{10}{}_n$ and n of $R^{11}{}_n$ is 0, 1, 2 or 3, and with each $R^{10}$ and with each $R^{11}$ independently from any other $R^{10}$ being selected from —OH, —F, —OCH$_3$, —OC$_2$H$_5$, —OnC$_3$H$_7$—OisoC$_3$H$_7$, —OCF$_3$, —CF$_3$ or —(CH$_2$)m-OR$_a$, with $R_a$ being selected from hydrogen, —CH$_3$, —CH$_2$CH$_3$, —CH$_2$CH$_2$CH$_3$, —CH$_2$CH$_2$CH$_2$CH$_3$, —CH(CH$_3$)$_2$, —CH$_2$CH(CH$_3$)$_2$, —C(CH$_3$)$_3$, —C$_6$H$_5$—CH$_2$C$_6$H$_5$, with m being selected from 1 or 2, more particularly with one $R^{10}$ or $R^{11}$ being —OH and the other $R^{10}$ or $R^{11}$ being —OCH$_3$, —OC$_2$H$_5$ or —OiPr respectively.

In one further preferred embodiment of $R^{13}{}_n$, n is 1 or 2, in particular 1, and $R^{13}$ is —OH, wherein in case of n is 1 $R^{13}$ is preferably in 2-position (i.e. ortho position to —CO—) or in 3-position (i.e. ortho-position to —NR$^8$—). In case n=2 one $R^{13}$ is OH (ortho position to —CO—) and the other is —OCH$_3$ (ortho-position to —NR$^8$—).

In yet another preferred embodiment of the present compound the moiety T is —CO$_2$H, —SO$_3$H, —C(=O)OR$^a$ or —CON(R$^a$)$_2$, with $R^a$ being selected from hydrogen, —CH$_3$, —CH$_2$CH$_3$, —CH$_2$CH$_2$CH$_3$, —CH$_2$CH$_2$CH$_2$CH$_3$, —CH(CH$_3$)$_2$, —CH$_2$CH(CH$_3$)$_2$, —C(CH$_3$)$_3$, —C$_6$H$_5$—CH$_2$C$_6$H$_5$;

with T being in particular —CO$_2$H.

According to a second aspect, the solution relates to compounds having a molecular structure as defined by general formula (9)

wherein BC being selected from

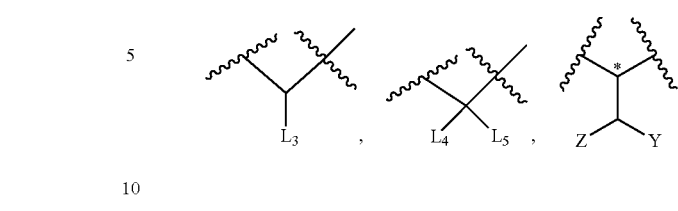

$L^3$, $L^4$ being selected independently from each other from —H, —CH$_3$, —CH$_2$CH$_2$CH$_2$NHC(NR$^c$)N(R$^b$)(R$^a$), —CH$_2$CON(R$^b$)(R$^a$), —CH$_2$C(=O)OR$^a$, —CH$_2$SR$^a$, —CH$_2$CH$_2$C(=O)N(R$^b$)(R$^a$), —CH$_2$CH$_2$C(=O)OR$^a$, —CH$_2$(C$_3$H$_3$N$_2$), —CH$_2$CH$_2$CH$_2$NH$_2$, —CH$_2$CH$_2$SCH$_3$, —CH$_2$(C$_6$H$_5$), —CH$_2$CH$_2$CH$_2$—, —CH$_2$OR$^a$, —CH(OR$^a$)CH$_3$, —CH$_2$(C$_8$H$_6$N)OR$^a$, —CH$_2$(C$_6$H$_4$)OR$^a$, —CH(CH$_3$)$_2$, —CCH, —CN, —OCH$_3$, —CF$_3$, —R$^a$, —CH(R$^b$)(R$^a$), —CH$_2$C(=O)R$^a$, —C(=O)OR$^a$, —OC(=O)NR$^b$R$^a$, —C(=O)NR$^b$R$^a$, —CH$_2$C(=O)NR$^b$ (OR$^a$), —CH$_2$S(O$_2$)R$^a$, —S(O$_2$)OR$^a$, —CH$_2$S(O$_2$)OR$^a$, —CH$_2$NR$^b$C(=O)R$^a$, —CH$_2$NR$^b$S(O$_2$)R$^a$, —CH$_2$P(=O)(OR$^b$)(OR$^a$), —CH$_2$P(=O)(OR$^b$)(R$^a$), —CH$_2$P(=O)(R$^b$)(R$^a$) or —CH$_2$S(O$_2$)NR$^b$R$^a$, and with $R^a$ and $R^b$ being selected, where applicable, independently from each other from a substituted or unsubstituted $C_1$-$C_4$ alkyl, a substituted or unsubstituted $C_1$-$C_4$ carboxy, a substituted or unsubstituted $C_2$-$C_4$ alkenyl, a substituted or unsubstituted $C_2$-$C_4$ alkynyl, or a $C_1$-$C_4$ haloalkyl, or a substituted or unsubstituted $C_3$-$C_{10}$ cycloalkyl or a substituted or unsubstituted $C_3$-$C_{10}$ halo cycloalkyl, or a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or a substituted or unsubstituted $C_5$-$C_{10}$ heteroaryl, or a substituted or unsubstituted $C_6$-$C_{10}$ aryl, with $L^5$ being selected from —CH$_3$, —CH$_2$CH$_3$, —OCH$_3$, —OCH$_2$CH$_3$, a $C_1$-$C_2$-fluoro alkyl, —NH$_2$;

with Y being —CN, —C(=O)OH, —C(=O)OCH$_3$, —C(=O)OCH$_2$CH$_3$, —C(=O)NHCH$_3$, —C(=O)NHCH$_2$CH$_3$, —C(=O)N(CH$_3$)$_2$, —C(=O)N(CH$_2$CH$_3$)$_2$, —C(=O)N(CH$_3$)(CH$_2$CH$_3$) or —C(=O)NH$_2$,

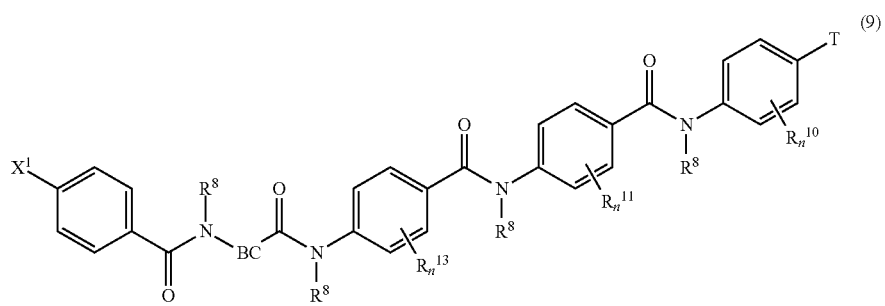

(9)

with Z being —H, —OH, —CH$_3$, —CH$_2$CH$_3$, —OCH$_3$, —NH$_2$, —NHCH$_3$, —N(CH$_3$)$_2$, —N(CH$_3$)$_3^{30}$, wherein X$^1$, BC, R$^8$, R$^{11}_n$, R$^{10}_n$ and T have the above meaning, and with n of R$^{13}_n$ being 1, 2, 3 or 4, in particular n of R$^{13}_n$ being 1 or 2, and with each R$^{13}$ being selected independently from any other R$^{13}$ from —OH, substituted or unsubstituted —C$_1$-C$_6$ alkyl or substituted or unsubstituted C$_1$-C$_6$ alkoxy;

In a preferred embodiment n is 1 and R$^{13}$ is OH, wherein R$^{13}$ is preferably in 2-position (i.e. ortho position to —CO—) or in 3-position (i.e. ortho-position to —NR8-).

In an embodiment of the compound of general formula (9) BC is selected from

L$^3$, L$^4$ being selected independently from each other from —H, —CH$_3$, —CH$_2$CH$_2$CH$_2$NHC(NR$^c$)N(R$^b$)(R$^a$), —CH$_2$CON(R$^b$)(R$^a$), —CH$_2$C(=O)OR$^a$, —CH$_2$SR$^a$, —CH$_2$CH$_2$C(=O)N(R$^b$)(R$^a$), —CH$_2$CH$_2$C(=O)OR$^a$, —CH$_2$(C$_3$H$_3$N$_2$), —CH$_2$CH$_2$CH$_2$NH$_2$, —CH$_2$CH$_2$SCH$_3$, —CH$_2$(C$_6$H$_5$), —CH$_2$OR$^a$, —CH(OR$^a$)CH$_3$, —CH$_2$(C$_8$H$_6$N)OR$^a$, —CH$_2$(C$_6$H$_4$)OR$^a$, —CH(CH$_3$)$_2$, —CN, —OCH$_3$, —CH(R$^b$)(R$^a$), —CH$_2$C(=O)R$^a$, —C(=O)OR$^a$, —OC(=O)NR$^b$R$^a$, —C(=O)NR$^b$R$^a$, —CH$_2$C(=O)NR$^b$ (OR$^a$), or —CH$_2$NR$^b$C(=O)R$^a$, L$^5$ being selected from —CH$_3$, —CH$_2$CH$_3$, —OCH$_3$, —OCH$_2$CH$_3$, —NH$_2$, Z being H and Y being CN or —C(=O)NH$_2$, more preferably Z being H and Y being CN.

It is to be understood that in case of moieties R$^{10}$, R$^{11}$ and R$^{13}$ of the compounds of general formula (9) the substitutional pattern may be the same as depicted in one of the formula (2)-(8); i.e. in particular R$^{10}$ and R$^{11}$ may have similar meanings and positions as depicted in one of the compounds of formula (2)-(8).

Variants of the compound of general formula (9) are also included, wherein R$^{13}_n$ is absent (i.e. n is 0). In this case is it is to be understood that albicidin is excluded. In these specific variants BC is

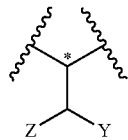

with Z being H and Y being CN,

X1 is

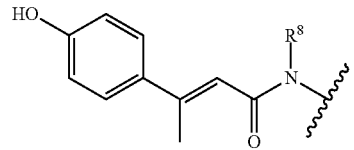

with R$^8$ being H,

T is —CO$_2$H, and

R$^{10}$ and R$^{11}$ are —OH or —OCH$_3$ with the specific substitutional arrangement as depicted in any of the formulas (4)-(8).

Particular embodiments of the solution are one the following compounds:

Compound 1

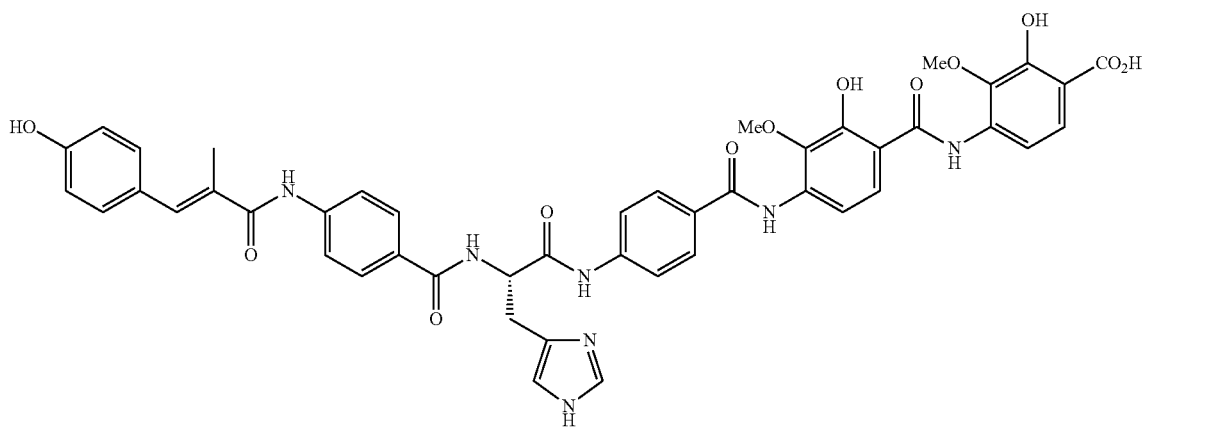 [SMILES: COc1c(NC(=O)c2ccc(NC(=O)c3ccc(NC(=O)[C@H](Cc4c[nH]cn4)NC(=O)c4ccc(NC(=O)/C(C)=C/c5ccc(O)cc5)cc4)cc3)c(OC)c2O)ccc(C(=O)O)c1O]

Compound 2
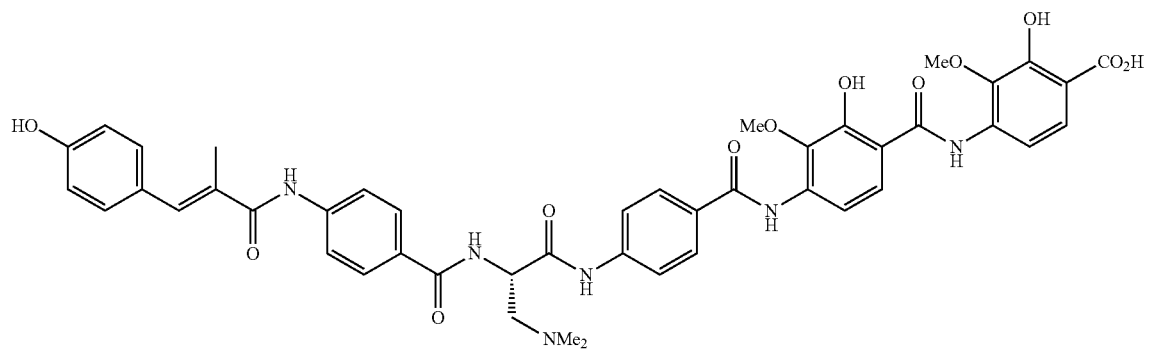 [SMILES: COc1c(NC(=O)c2ccc(NC(=O)c3ccc(NC(=O)[C@H](CN(C)C)NC(=O)c4ccc(NC(=O)/C(C)=C/c5ccc(O)cc5)cc4)cc3)c(OC)c2O)ccc(C(=O)O)c1O]
Compound 3
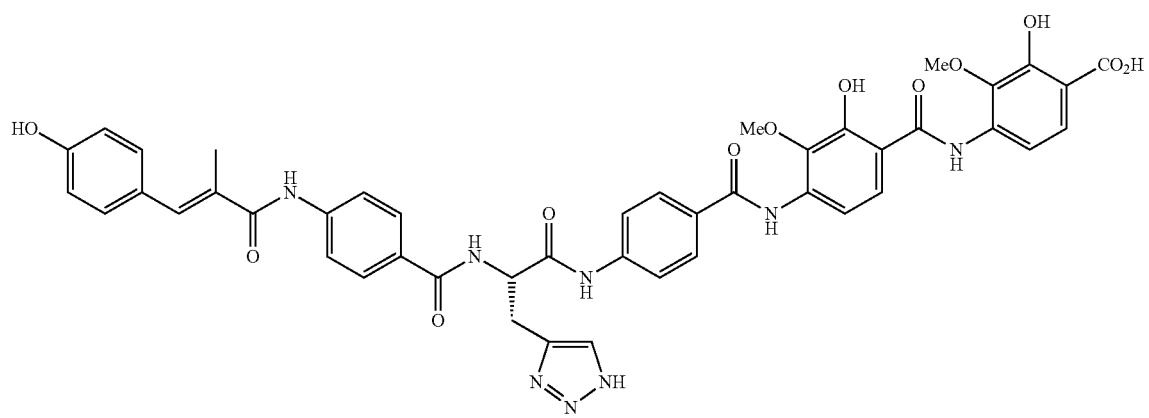
Compound 4
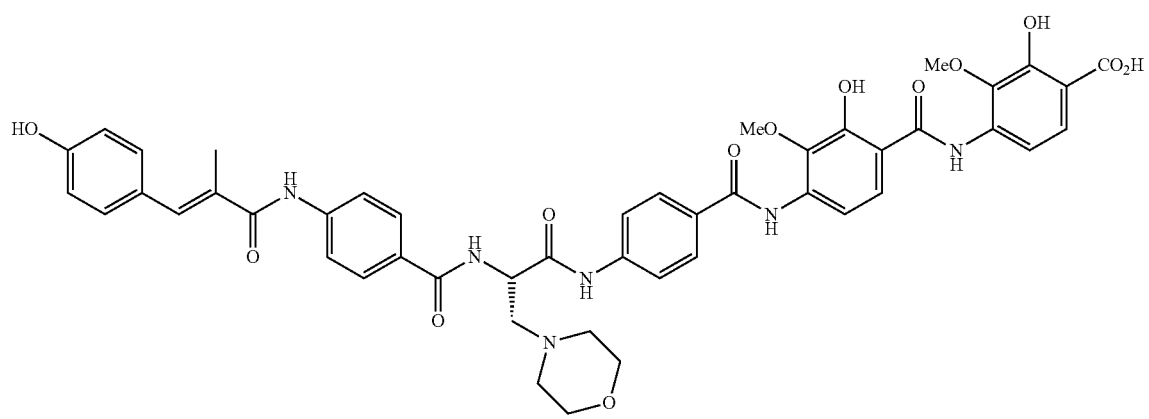

Compound 5
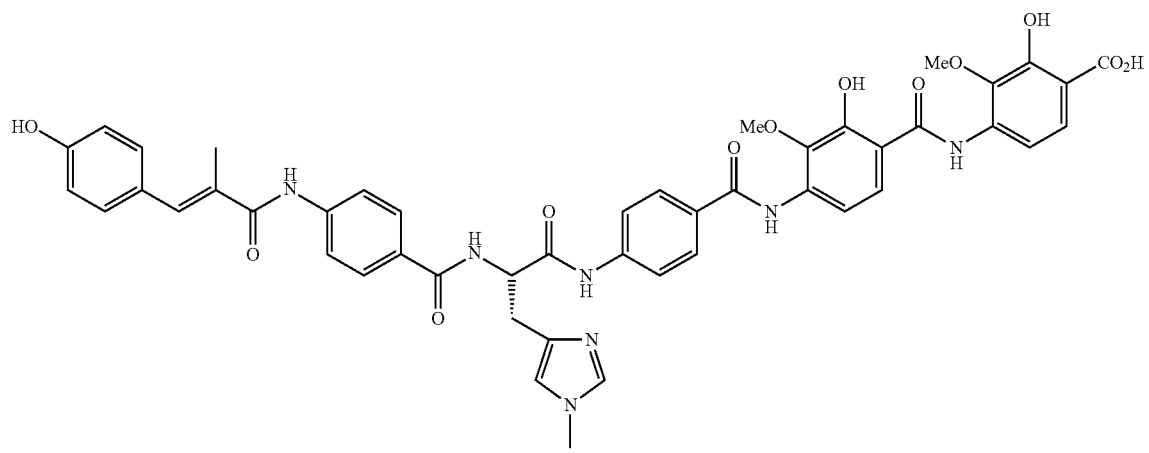
Compound 6
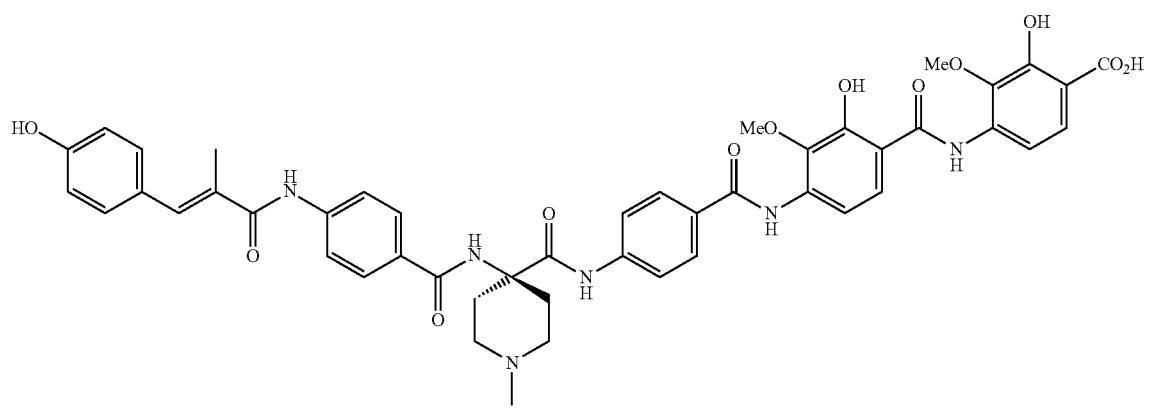
Compound 7
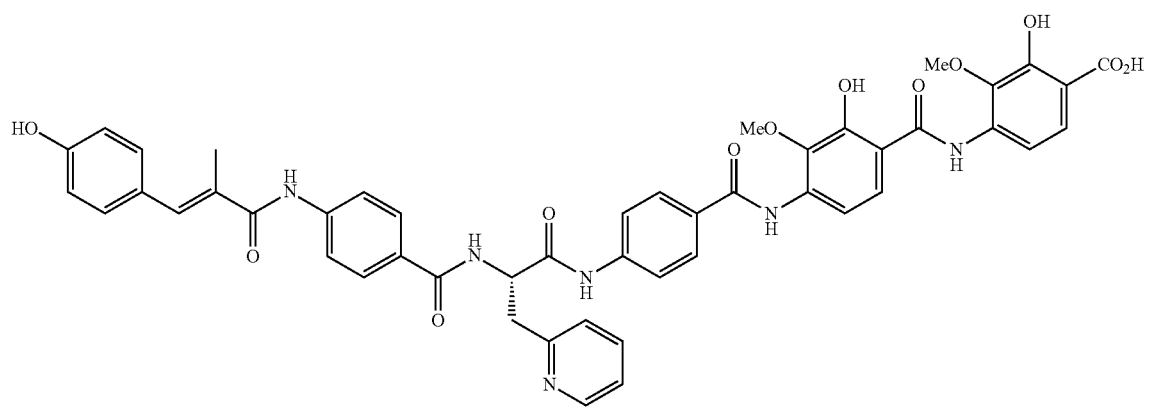

-continued
Compound 8
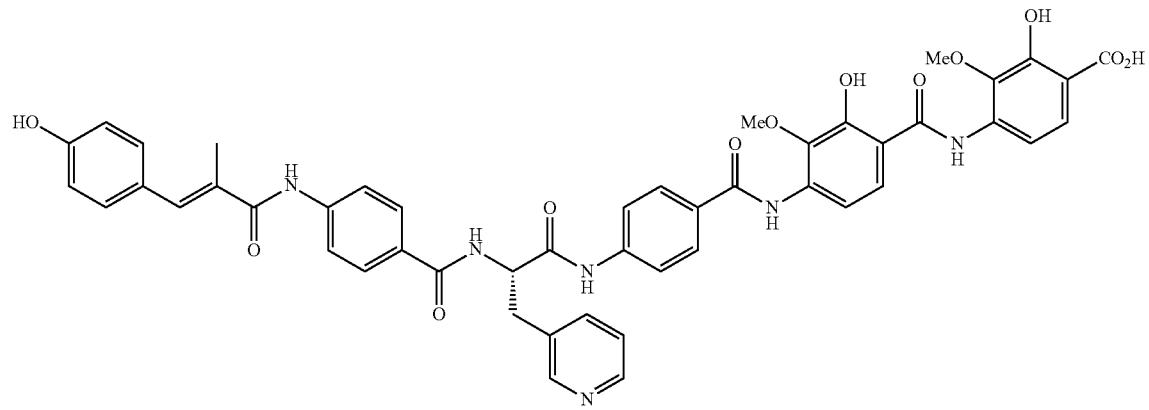 [SMILES: COc1c(NC(=O)c2ccc(NC(=O)c3ccc(NC(=O)[C@H](Cc4cccnc4)NC(=O)c4ccc(NC(=O)/C(C)=C/c5ccc(O)cc5)cc4)cc3)c(OC)c2O)ccc(C(=O)O)c1O]
Compound 9
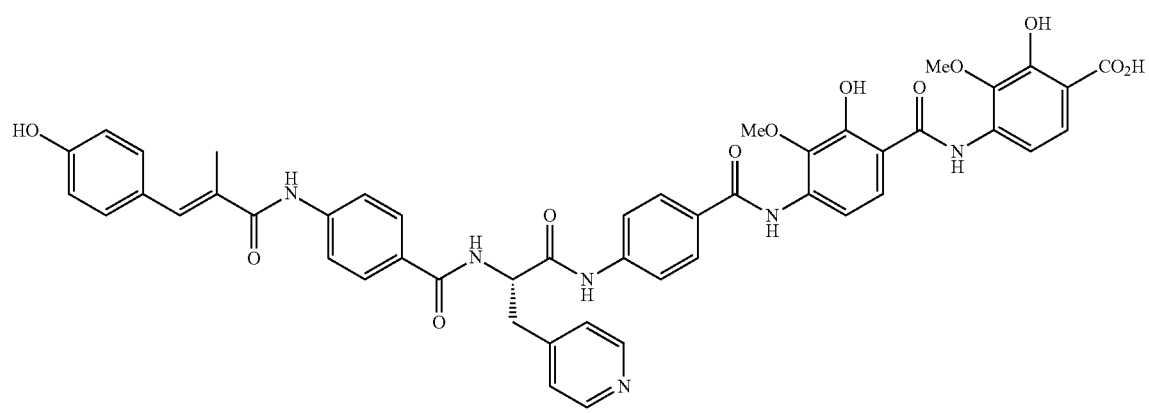 [SMILES: COc1c(NC(=O)c2ccc(NC(=O)c3ccc(NC(=O)[C@H](Cc4ccncc4)NC(=O)c4ccc(NC(=O)/C(C)=C/c5ccc(O)cc5)cc4)cc3)c(OC)c2O)ccc(C(=O)O)c1O]
Compound 10
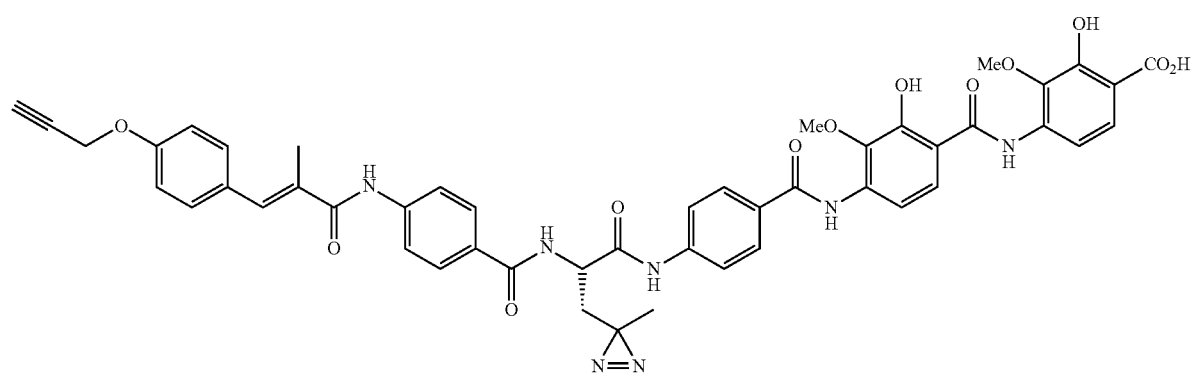
Compound 11
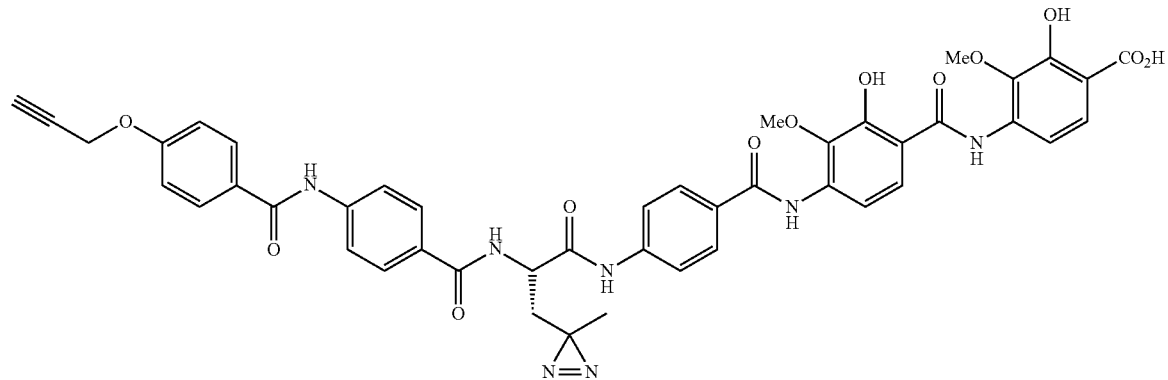

-continued
Compound 12
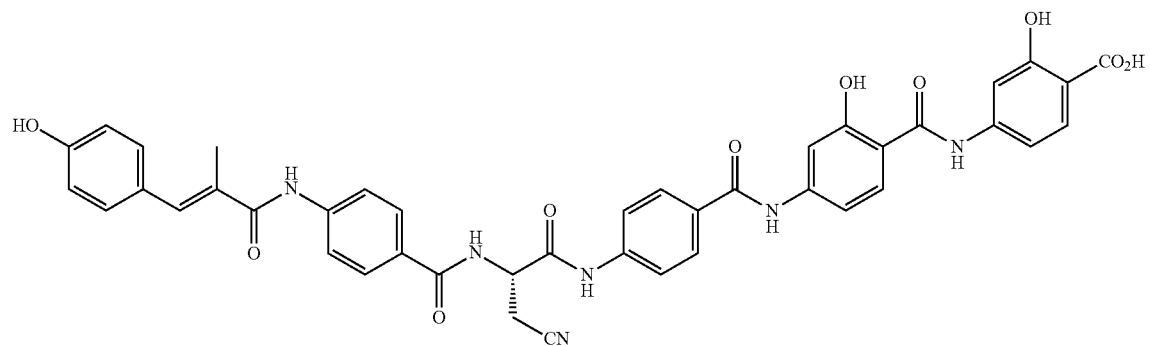 [SMILES: C/C(=C\c1ccc(O)cc1)C(=O)Nc1ccc(C(=O)N[C@@H](CC#N)C(=O)Nc2ccc(C(=O)Nc3ccc(C(=O)Nc4ccc(C(=O)O)c(O)c4)c(O)c3)cc2)cc1]
Compound 13
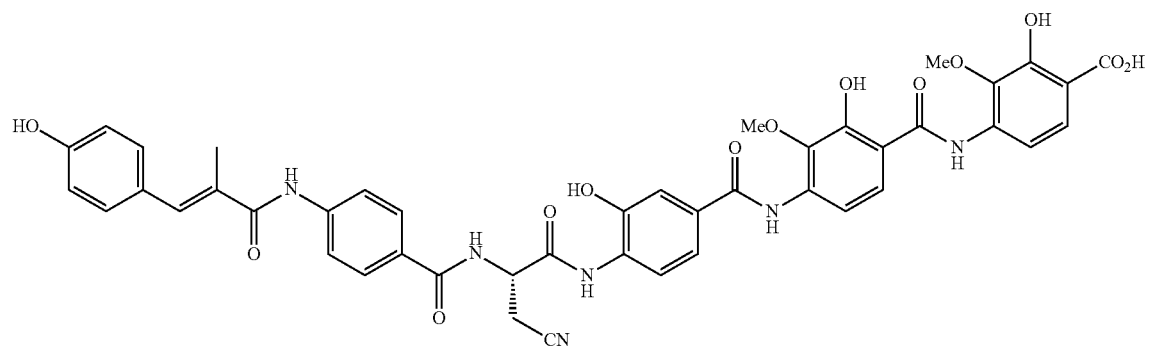 [SMILES: COc1c(NC(=O)c2ccc(NC(=O)c3ccc(NC(=O)[C@H](CC#N)NC(=O)c4ccc(NC(=O)/C(C)=C/c5ccc(O)cc5)cc4)c(O)c3)c(OC)c2O)ccc(C(=O)O)c1O]
Compound 14
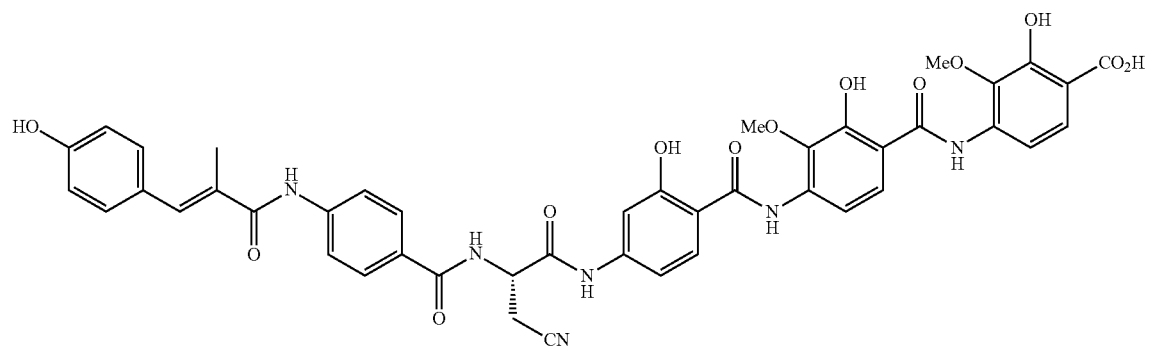 [SMILES: COc1c(NC(=O)c2ccc(NC(=O)c3ccc(NC(=O)[C@H](CC#N)NC(=O)c4ccc(NC(=O)/C(C)=C/c5ccc(O)cc5)cc4)cc3O)c(OC)c2O)ccc(C(=O)O)c1O]
Compound 15
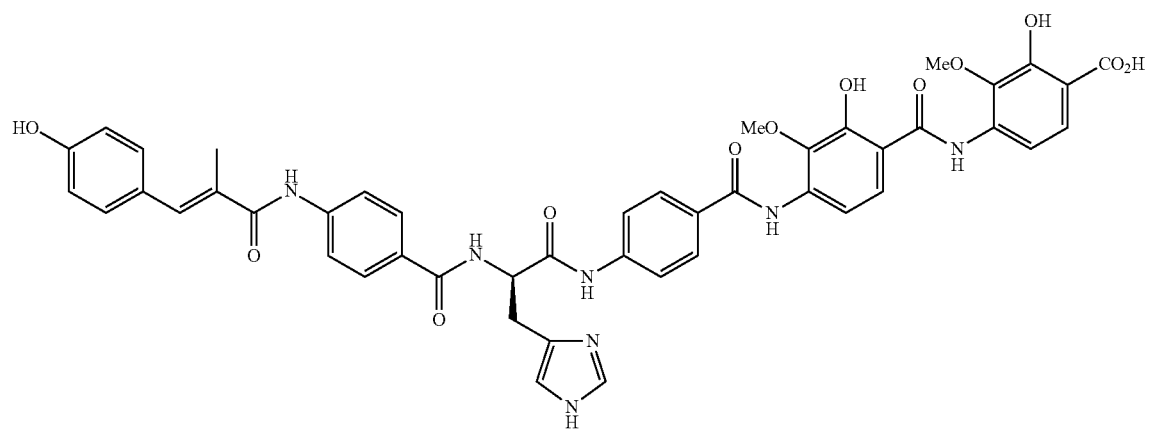

-continued
Compound 16
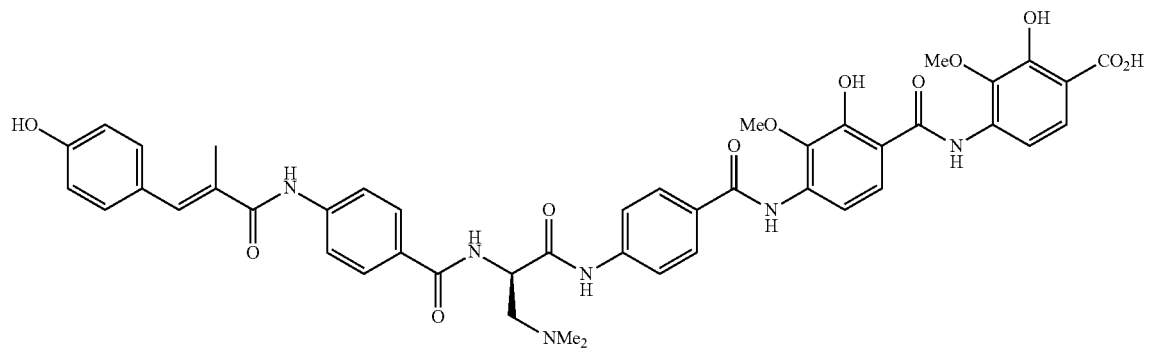
Compound 17
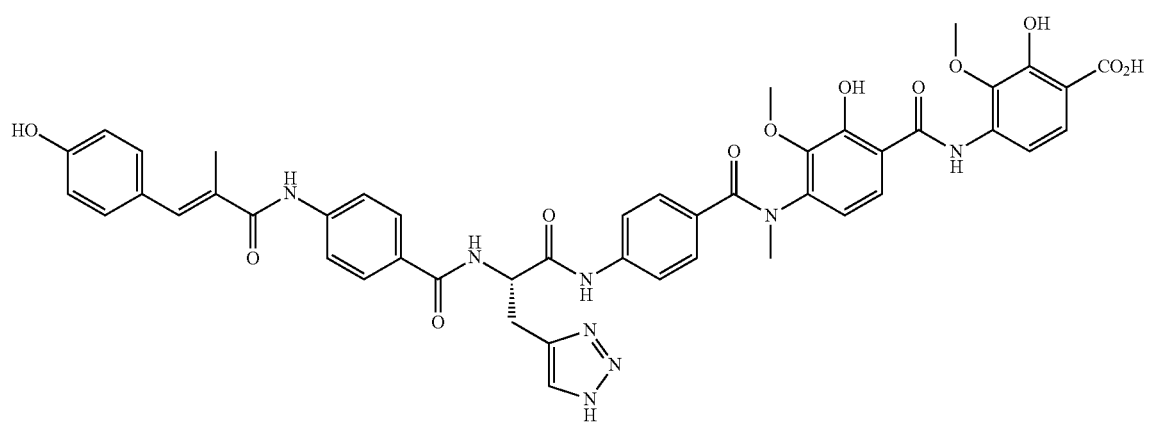 [SMILES: COc1c(NC(=O)c2ccc(N(C)C(=O)c3ccc(NC(=O)[C@H](Cc4c[nH]nn4)NC(=O)c4ccc(NC(=O)/C(C)=C/c5ccc(O)cc5)cc4)cc3)c(OC)c2O)ccc(C(=O)O)c1O]
Compound 18
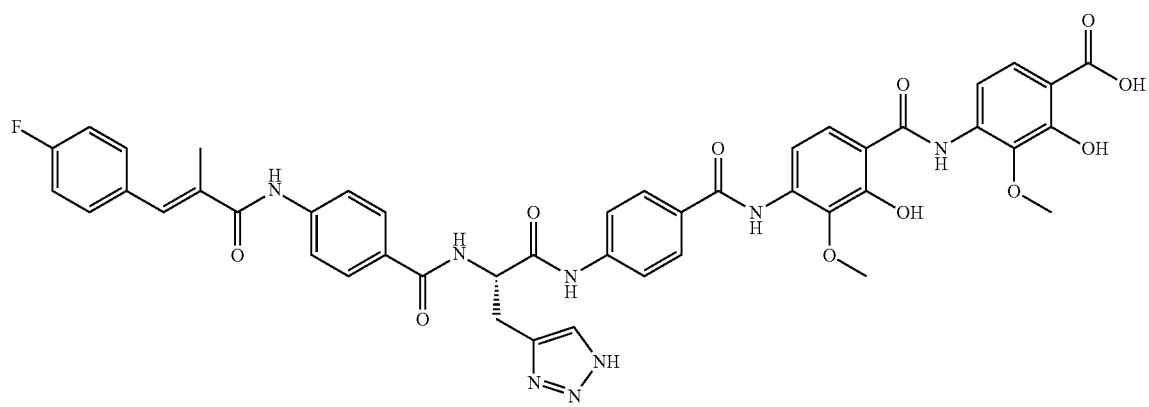 [SMILES: COc1c(NC(=O)c2ccc(NC(=O)c3ccc(NC(=O)[C@H](Cc4c[nH]nn4)NC(=O)c4ccc(NC(=O)/C(C)=C/c5ccc(F)cc5)cc4)cc3)c(OC)c2O)ccc(C(=O)O)c1O]
Compound 19
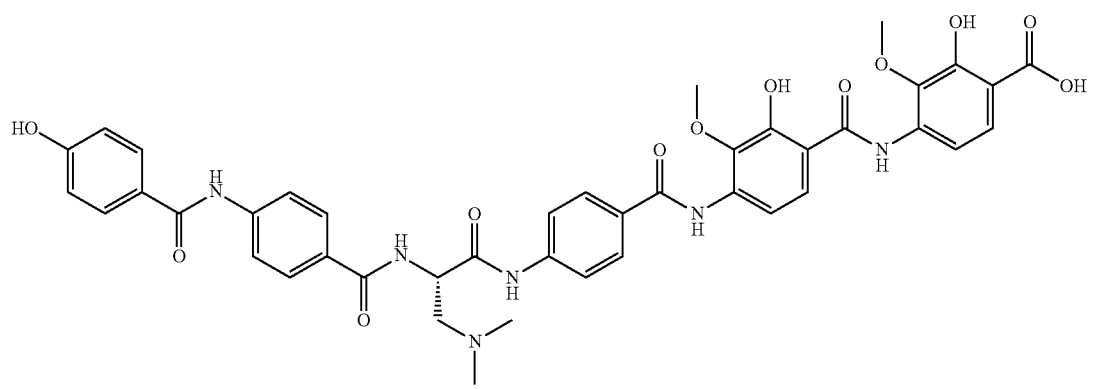

Compound 20
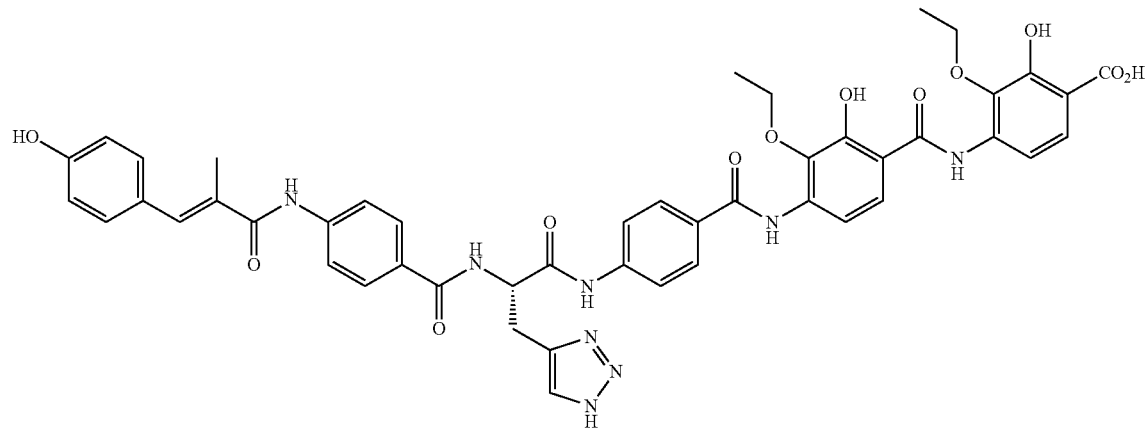
Compound 21
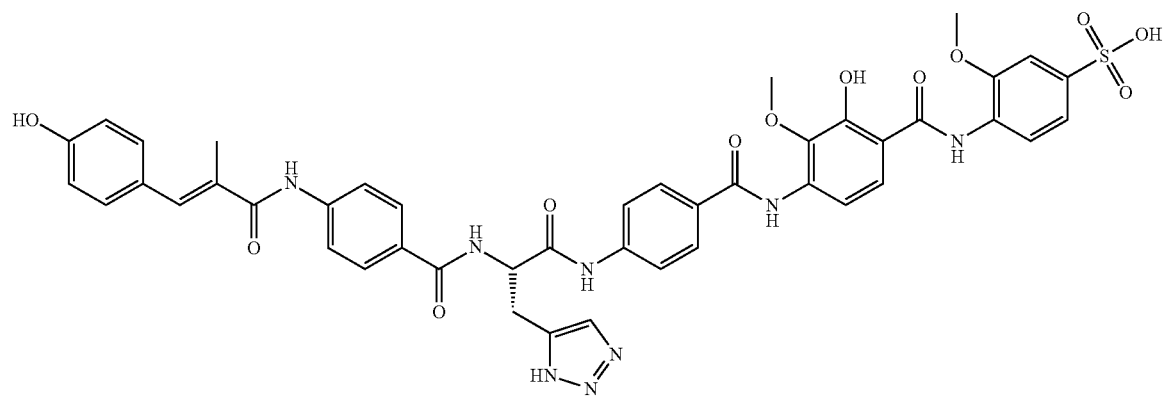
Compound 22
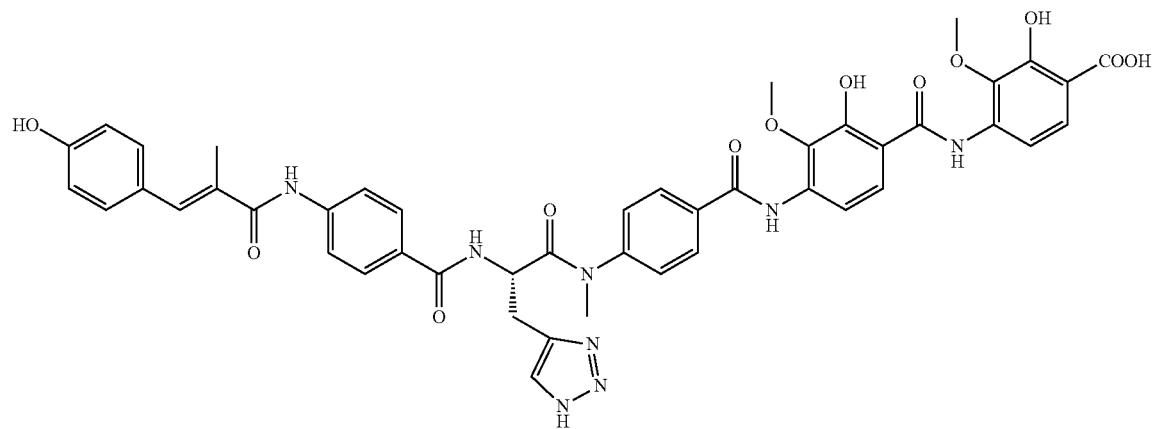

-continued
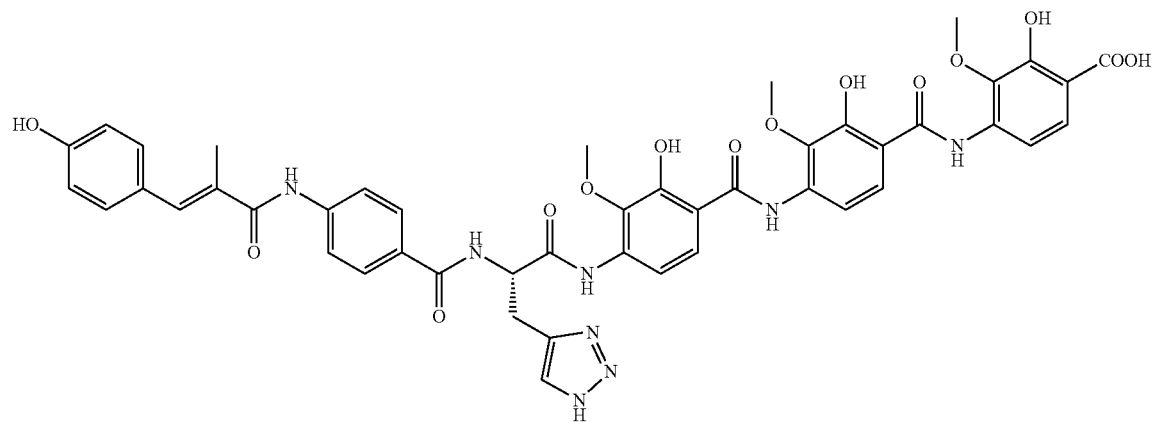
Compound 23
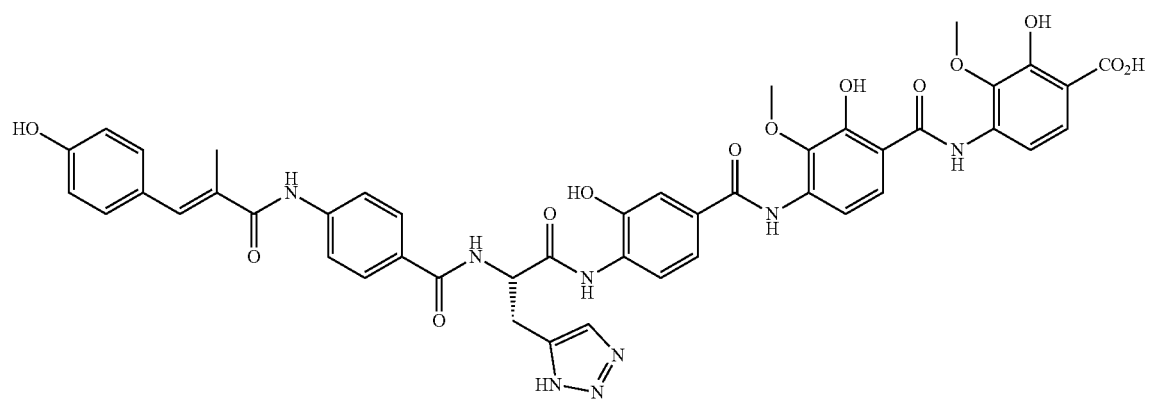
Compound 24
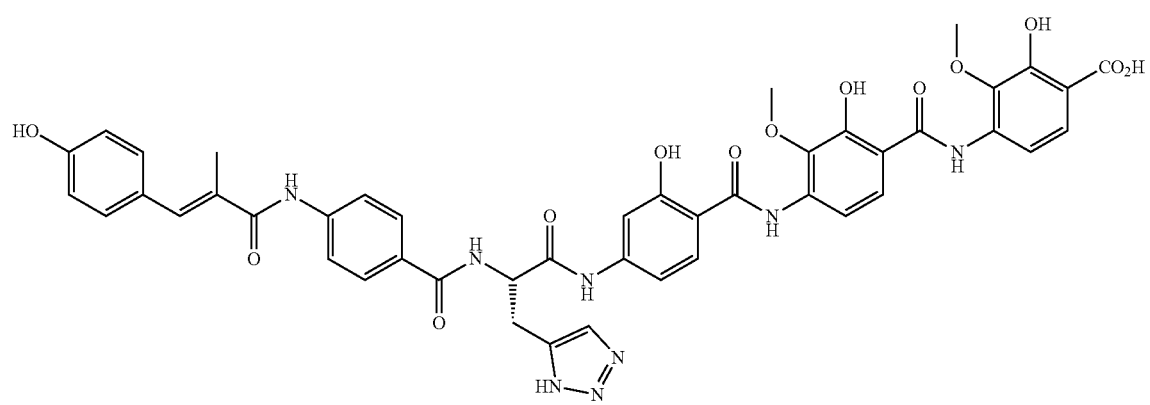
Compound 25

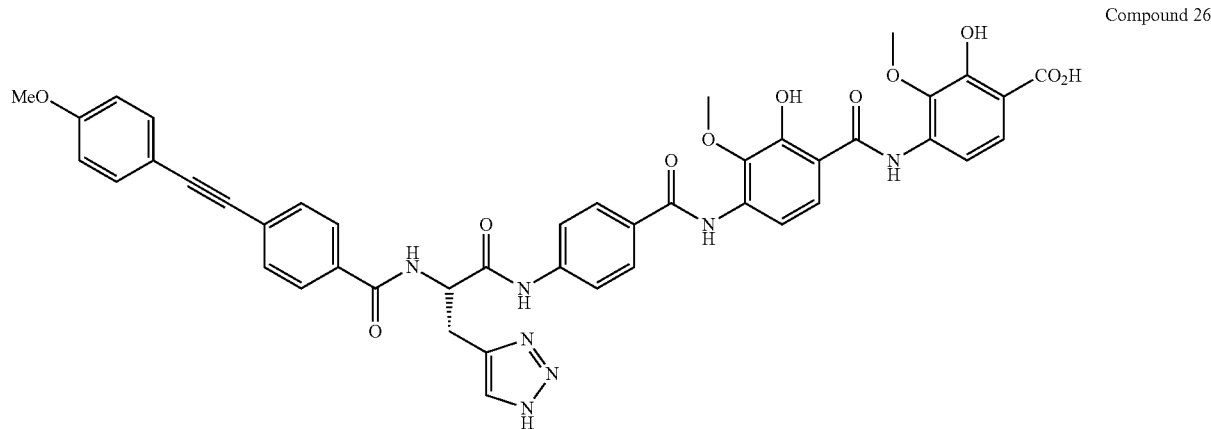

Compound 26

The compounds of the solution may be used in a method of treatment of diseases, in particular for use in a method of treatment of bacterial infections. For this purpose, the present compounds may be provided in a pharmaceutical acceptable form.

Pharmaceutically acceptable salts of the present compounds mean both their organic and inorganic salts as described in Remington's Pharmaceutical Sciences (17th edition, page 1418 (1985)). Because of the physical and chemical stability and the solubility, preference is given for acidic groups inter alia to sodium, potassium, calcium and ammonium salts; preference is given for basic groups inter alia to salts of maleic acid, fumaric acid, succinic acid, malic acid, tartaric acid, methylsulfonic acid, hydrochloric acid, sulfuric acid, phosphoric acid or of carboxylic acids or sulfonic acids, for example as hydrochlorides, hydrobromides, phosphates, sulfates, methanesulfonates, acetates, lactates, maleates, fumarates, malates, gluconates, and salts of amino acids, of natural bases or carboxylic acids. The preparation of pharmaceutically acceptable salts from compounds of the formula (I) which are capable of salt formation, including their stereoisomeric forms, takes place in a manner known per se. The present compounds form stable alkali metal, alkaline earth metal or optionally substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. Where the compounds of the formula (I) have basic groups, stable acid addition salts can also be prepared with strong acids. Suitable pharmaceutically acceptable acid addition salts of the compounds of the solution are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. The hydrochloride salt is a preferred salt.

Salts with a pharmaceutically unacceptable anion such as, for example, trifluoroacetate likewise belong within the framework of the solution as useful intermediates for the preparation or purification of pharmaceutically acceptable salts and/or for use in non-therapeutic, for example in vitro, applications.

The solution furthermore relates to pharmaceutical preparations (or pharmaceutical compositions) which contain an effective amount of at least one of the present compounds and/or its pharmaceutically acceptable salts and a pharmaceutically acceptable carrier, i. e. one or more pharmaceutically acceptable carrier substances (or vehicles) and/or additives (or excipients). The pharmaceuticals can be administered orally, for example in the form of pills, tablets, lacquered tablets, coated tablets, granules, hard and soft gelatine capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the solution are prepared in a manner known per se and familiar to one skilled in the art, pharmaceutically acceptable inert inorganic and/or organic carrier substances and/or additives being used in addition to the compound(s) of the formula (I) and/or its (their) pharmaceutically acceptable salts and/or its (their) prodrugs. For the production of pills, tablets, coated tablets and hard gelatine capsules it is possible to use, for example, lactose, corn starch or derivatives thereof, talc, stearic acid or its salts, etc. Carrier substances for soft gelatine capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of the present compounds and/or their pharmaceutically acceptable salts and/or their prodrugs. The amount of the active ingredient of the formula (I) and/or its pharmaceutically acceptable salts and/or its prodrugs in the pharmaceutical preparations normally is from about 0.5 to about 1000 mg, preferably from about 1 to about 500 mg.

A prodrug within the meaning of the solution is a precursor chemical compound of a biological active compound of the solution. Instead of administering the active compound or drug, a prodrug might be used instead to improve the absorption, distribution, metabolization and excretion. Prodrugs are often designed to improve bioavailability when a drug itself is poorly absorbed from the gastrointestinal tract. A prodrug may also be used to improve the selectively of the drug. This reduces adverse or unintended effects of a drug, especially important in treatments like chemotherapy, which can have severe unintended and undesirable side effects.

In addition to the active compound according to the solution and/or their pharmaceutically acceptable salts and to carrier substances, the pharmaceutical preparations can contain one or more additives such as, for example, fillers, disintegrants, binders, lubricants, wetting agents, stabilizers, emulsifiers, preservatives, sweeteners, colorants, flavourings, aromatizers, thickeners, diluents, buffer substances, solvents, solubilizers, agents for achieving a depot effect, salts for altering the osmotic pressure, coating agents or antioxidants. They can also contain two or more of the present compounds and/or their pharmaceutically acceptable salts.

In case a pharmaceutical preparation contains two or more of the present compounds the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the present compounds allows a great deal of control over the biological and physico-chemical properties of the compounds and thus allows the selection of such desired compounds. Furthermore, in addition to at least one compound and/or its pharmaceutically acceptable salts, the pharmaceutical preparations can also contain one or more other therapeutically or prophylactically active ingredients.

When using the present compounds the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behaviour it may be necessary to deviate upwards or downwards from the daily dose indicated.

The compounds of the solution may also exist in various polymorphous forms, for example as amorphous and crystalline polymorphous forms. All polymorphous forms of the compounds of the solution belong within the framework of the solution and are a further aspect of the solution.

The compounds of the solution may be present as optical isomers or as mixtures thereof. The solution relates both to the pure isomers and all possible isomeric mixtures and is hereinafter understood as doing so, even if stereochemical details are not specifically mentioned in every case. Enantiomeric mixtures of compounds of the general formula 1, which are obtainable by the process or any other way, may be separated in known manner—on the basis of the physical-chemical differences of their components—into pure enantiomers, for example by fractional crystallisation, distillation and/or chromatography, in particular by preparative HPLC using a chiral HPLC column.

According to the solution, apart from separation of corresponding isomer mixtures, generally known methods of diastereoselective or enantioselective synthesis can also be applied to obtain pure diastereoisomers or enantiomers, e.g. by carrying out the method described hereinafter and using educts with correspondingly suitable stereochemistry.

It is advantageous to isolate or synthesise the biologically more active isomer, provided that the individual compounds have different biological activities.

Methods of Synthesis

Methods for synthesizing the compounds of the present are described in detail in WO 2014/125075 A1.

One general procedure for the synthesis of albicidin-derivatives with variations of the central amino acid, in particular compounds of general formula (1)-(8), may comprises the steps according to the general reaction scheme 1:

Reaction scheme 1

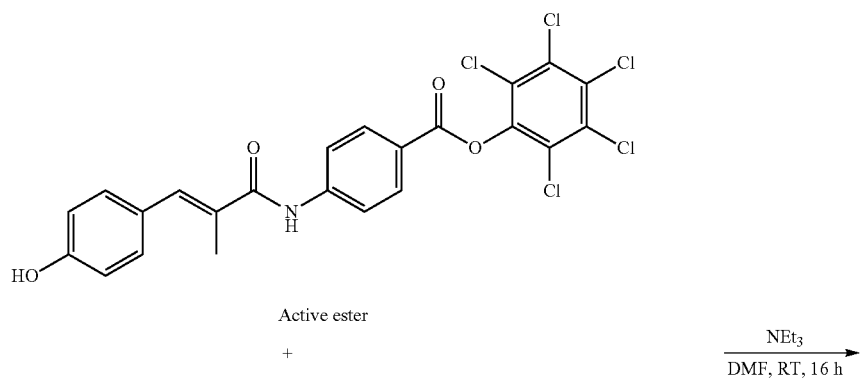

Active ester
+

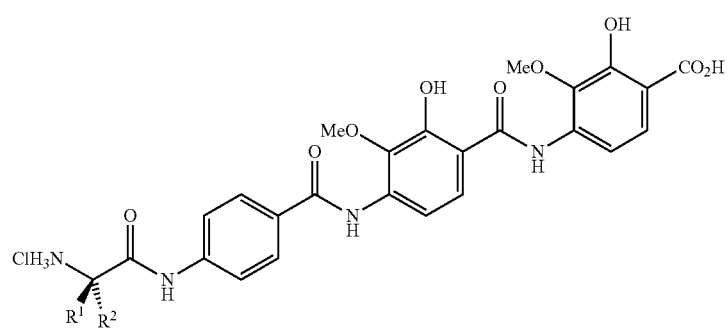

$\xrightarrow[\text{DMF, RT, 16 h}]{\text{NEt}_3}$

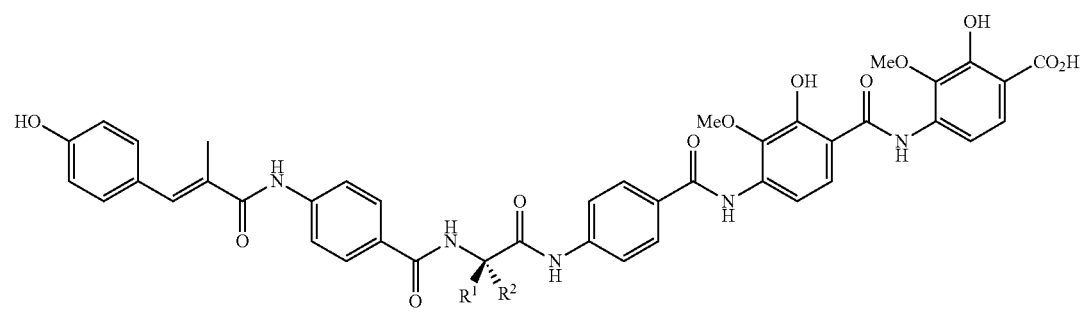

The amine is reacted with the active ester in basic conditions, preferably in the presence of triethylamine. Specifically, the corresponding amine is dissolved in anhydrous N,N'-dimethylformamide under an atmosphere of nitrogen. After the addition of triethylamine the active ester (see Figure 1) is added and the reaction mixture is stirred for 16 h in the dark. All volatiles were removed under high vacuum and the residue was purified by means of preparative HPLC.

Another general procedure according to reaction scheme 2 enables the synthesis of albicidin-derivatives with variations of C-terminal building blocks, in particular compounds of general formula (9):

Reaction scheme 2

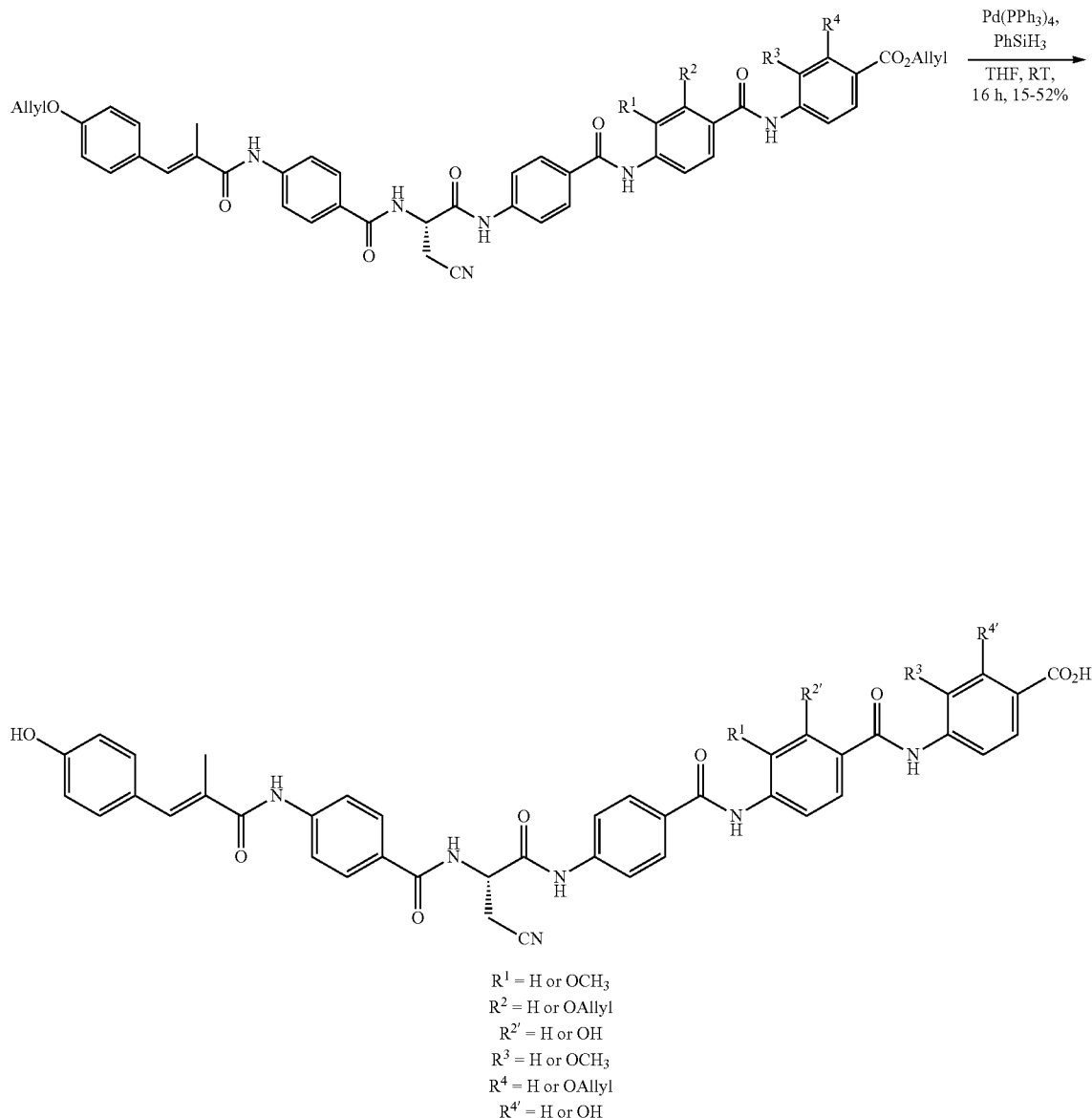

$R^1$ = H or $OCH_3$
$R^2$ = H or OAllyl
$R^{2'}$ = H or OH
$R^3$ = H or $OCH_3$
$R^4$ = H or OAllyl
$R^{4'}$ = H or OH Here, the corresponding protected albicidin is reacted with tetrakis(triphenylphosphine)palladium(0) and phenylsilane. Specifically, the corresponding protected albicidin (BBA-BBF) is dissolved in anhydrous tetrahydrofuran under an atmosphere of nitrogen. After the addition of tetrakis(triphenylphosphine)palladium(0) and phenylsilane the reaction mixture is stirred for 4 h in the dark. The reaction was quenched with acetic acid. All volatiles were removed in vacuo and the residue was dissolved in methanol, filtered and purified by means of preparative HPLC.

The present compounds can also be obtained in the form of their hydrates and/or also can include other solvents used for example for the crystallization of compounds present in the solid form. Depending on the method and/or the reaction conditions, the present compounds can be obtained in the free form or in the form of salts. Particularly in the form of salts of alkali metals, alkaline earth metals, ammonium or alkylammonium.

The present solution is explained in more detail by means of the following examples.

Compounds 1-11 are obtained in a synthesis procedure according to reaction scheme 1.

Compound 1: L-His-albicidin

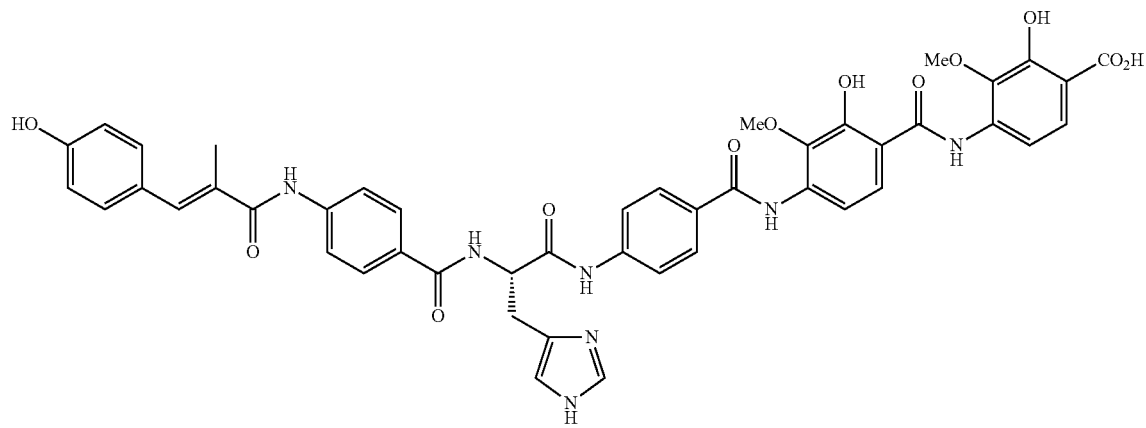

Compound 1 (L-His-albicidin) is synthesized in a multi-step synthesis route as follows:

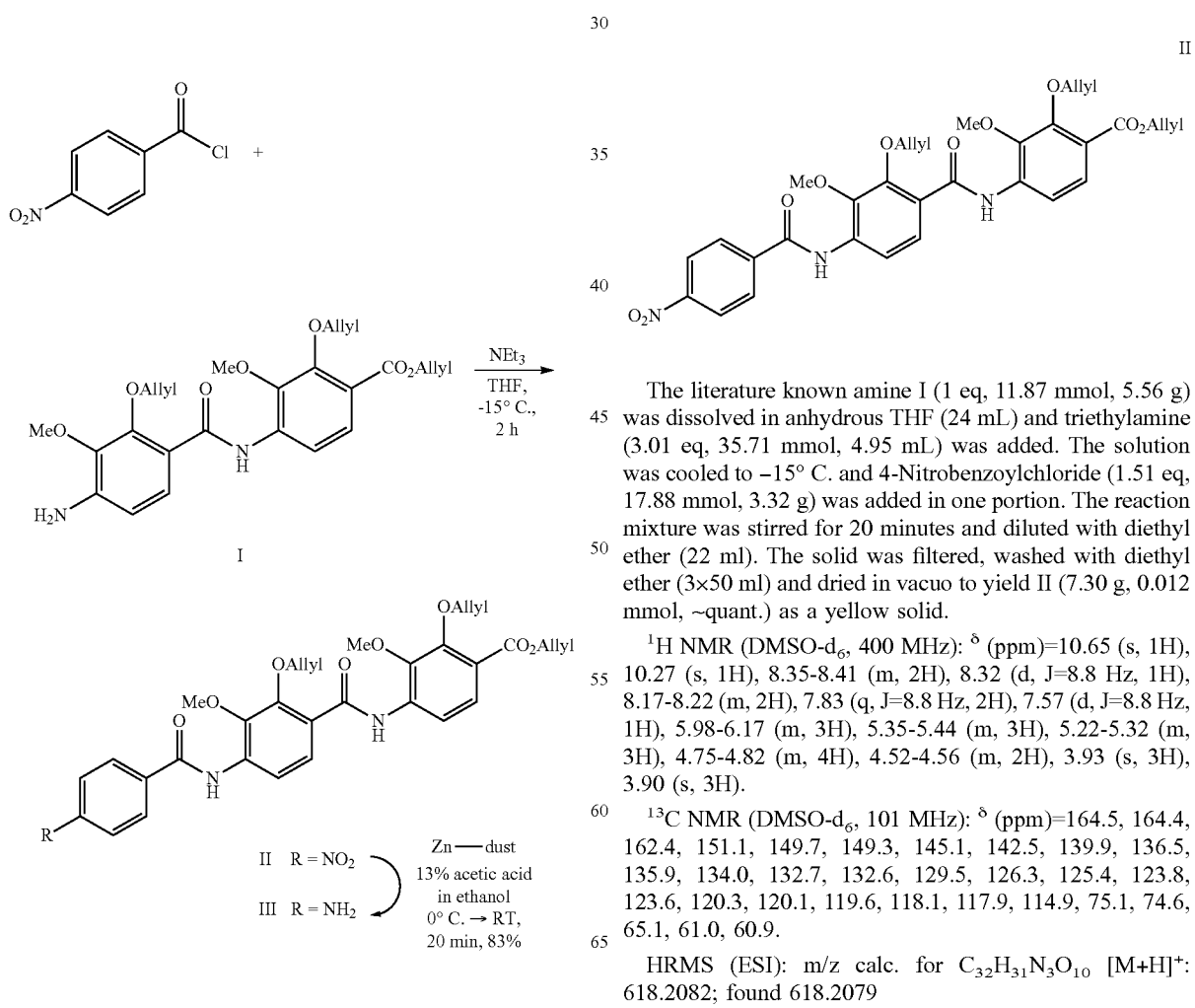

Preparation of Compound II:

The literature known amine I (1 eq, 11.87 mmol, 5.56 g) was dissolved in anhydrous THF (24 mL) and triethylamine (3.01 eq, 35.71 mmol, 4.95 mL) was added. The solution was cooled to −15° C. and 4-Nitrobenzoylchloride (1.51 eq, 17.88 mmol, 3.32 g) was added in one portion. The reaction mixture was stirred for 20 minutes and diluted with diethyl ether (22 ml). The solid was filtered, washed with diethyl ether (3×50 ml) and dried in vacuo to yield II (7.30 g, 0.012 mmol, ~quant.) as a yellow solid.

$^1$H NMR (DMSO-$d_6$, 400 MHz): δ (ppm)=10.65 (s, 1H), 10.27 (s, 1H), 8.35-8.41 (m, 2H), 8.32 (d, J=8.8 Hz, 1H), 8.17-8.22 (m, 2H), 7.83 (q, J=8.8 Hz, 2H), 7.57 (d, J=8.8 Hz, 1H), 5.98-6.17 (m, 3H), 5.35-5.44 (m, 3H), 5.22-5.32 (m, 3H), 4.75-4.82 (m, 4H), 4.52-4.56 (m, 2H), 3.93 (s, 3H), 3.90 (s, 3H).

$^{13}$C NMR (DMSO-$d_6$, 101 MHz): δ (ppm)=164.5, 164.4, 162.4, 151.1, 149.7, 149.3, 145.1, 142.5, 139.9, 136.5, 135.9, 134.0, 132.7, 132.6, 129.5, 126.3, 125.4, 123.8, 123.6, 120.3, 120.1, 119.6, 118.1, 117.9, 114.9, 75.1, 74.6, 65.1, 61.0, 60.9.

HRMS (ESI): m/z calc. for $C_{32}H_{31}N_3O_{10}$ [M+H]$^+$: 618.2082; found 618.2079

Preparation of Compound III

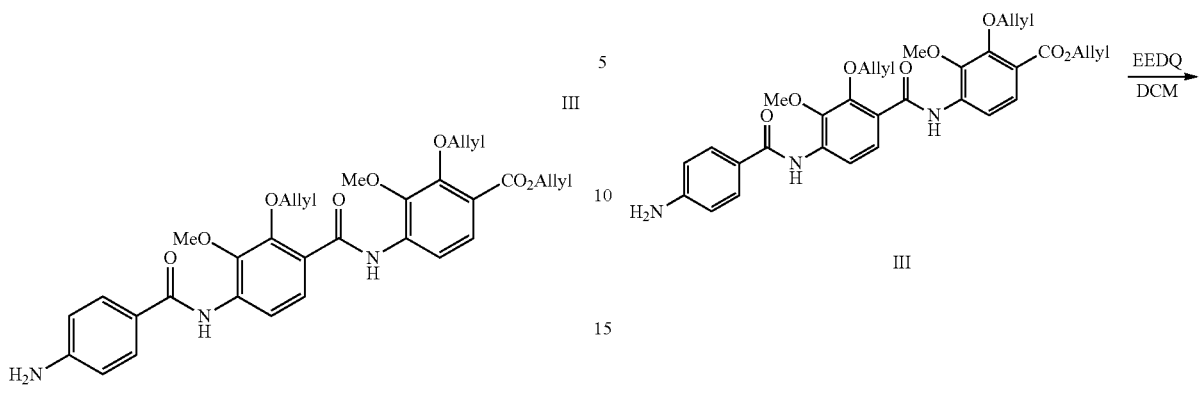

Compound II (1 eq, 12.84 mmol, 7.30 g) was suspended in a mixture of ethanol (800 ml) and acetic acid (100 ml) and cooled to 0° C. Zinc dust (33.80 g) was added portion wise. After 20 min the reaction was proven to be complete (verified by TLC-control). The solid was filtered and washed with DCM (3×100 ml). The combined liquids were evaporated to dryness. The residue was taken up in DCM (300 ml) and saturated aqueous $NaHCO_3$-Solution (300 ml). The aqueous phase was further extracted twice with DCM (2×100 ml). The combined organic fractions were washed successively with saturated aqueous $NaHCO_3$-Solution (1×300 ml), distilled water (1×300 ml) and brine (1×300 ml), dried over $Na_2SO_4$ and evaporated to obtain III (5.79 g, 9.85 mmol, 83%) as a yellow solid.

$^1$H NMR (DMSO-$d_6$, 400 MHz): δ (ppm)=10.65 (s, 1H), 9.19 (s, 1H), 8.34 (d, J=8.8 Hz, 1H), 8.01 (d, J=8.8 Hz, 1H), 7.79 (d, J=8.8 Hz, 1H), 7.68-7.74 (m, 2H), 7.57 (d, J=9.0 Hz, 1H), 6.59-6.65 (m, 2H), 5.98-6.18 (m, 3H), 5.89 (s, 2H), 5.40 (tdd, J=11.5, 5.6, 1.5 Hz, 3H), 5.21-5.32 (m, 3H), 4.75-4.83 (m, 4H), 4.54 (d, J=5.8 Hz, 2H), 3.93 (s, 3H), 3.92 (s, 3H).

$^{13}$C NMR (DMSO-$d_6$, 101 MHz): δ (ppm)=165.0, 164.4, 162.4, 152.7, 151.1, 149.4, 143.3, 142.4, 137.2, 136.6, 134.0, 132.7, 132.6, 129.4, 126.3, 125.6, 121.7, 120.2, 120.1, 120.0, 118.1, 117.8, 117.5, 114.8, 112.7, 75.1, 74.5, 65.1, 61.0, 60.9.

HRMS (ESI): m/z calc. for $C_{32}H_{33}N_3O_8$ [M+H]$^+$: 588.2340; found 588.2343

Preparation of Compound IV

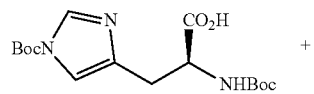 +

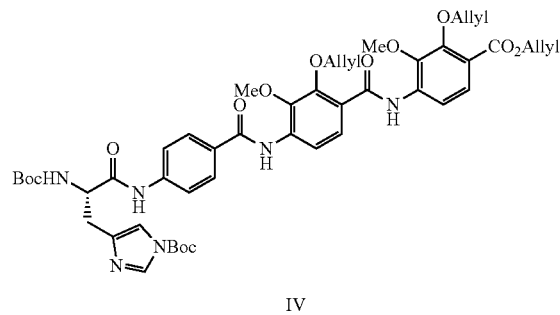

Commercially available N,N'-Bis(tert-Butoxycarbonyl)-L-Histidine (1 eq, 0.51 mmol, 181.5 mg) was dissolved in DCM (10 ml) and cooled to 0° C. N-Ethoxycarbonyl-2-ethoxy-1,2-dihydroqinoline (EEDQ) (1 eq, 0.51 mmol, 126 mg) was added and after 5 minutes compound III (0.34 eq, 0.17 mmol, 101.7 mg) was added. The reaction mixture was slowly warmed to room temperature and stirred for 16 h. All volatiles were removed in vacuo and the residue was taken up in ethyl acetate (100 ml). The organic fraction was washed with saturated aqueous $NaHCO_3$-Solution (3×50 ml) and brine (1×50 ml), dried over $Na_2SO_4$ and evaporated. The residue was purified via flash chromatography on silica gel eluting with 1-5% methanol in DCM. Compound IV (156.2 mg, 0.17 mmol, 98%) was obtained as a yellow oil.

$^1$H NMR (DMSO-$d_6$, 400 MHz): δ (ppm)=10.65-10.67 (m, 1H), 10.39-10.42 (m, 1H), 9.64-9.66 (m, 1H), 8.31-8.36 (m, 1H), 8.12-8.16 (m, 1H), 7.94-7.99 (m, 2H), 7.90-7.94 (m, 1H), 7.79-7.84 (m, 1H), 7.75-7.79 (m, 2H), 7.54-7.60 (m, 1H), 7.26-7.30 (m, 1H), 7.09-7.16 (m, 1H), 5.97-6.17 (m, 3H), 5.35-5.46 (m, 3H), 5.22-5.32 (m, 3H), 4.79-4.82 (m, 2H), 4.75-4.78 (m, 2H), 4.52-4.56 (m, 3H), 4.35-4.45 (m, 1H), 3.92-3.93 (m, 3H), 3.91-3.92 (m, 3H), 2.88-2.96 (m, 1H), 2.79-2.87 (m, 1H), 1.55 (s, 9H), 1.36 (s, 9H).

HRMS (ESI): m/z calc. for $C_{48}H_{56}N_6O_{13}$ [M+H]$^+$: 925.3978; found 925.3973

Preparation of Compound V

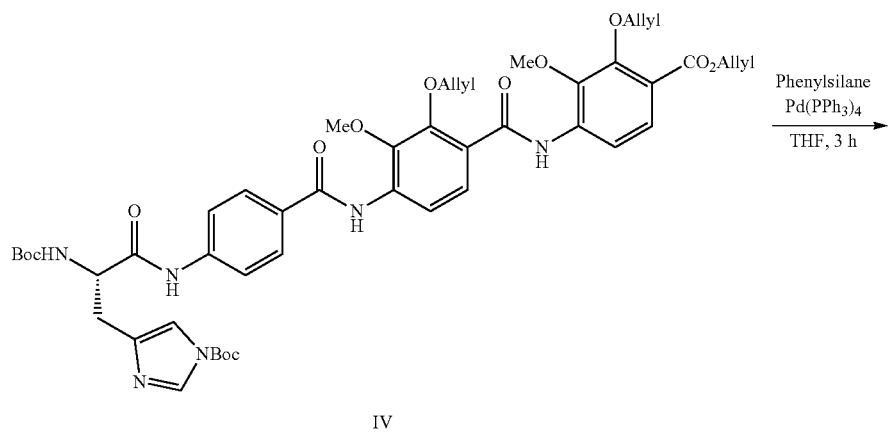

IV

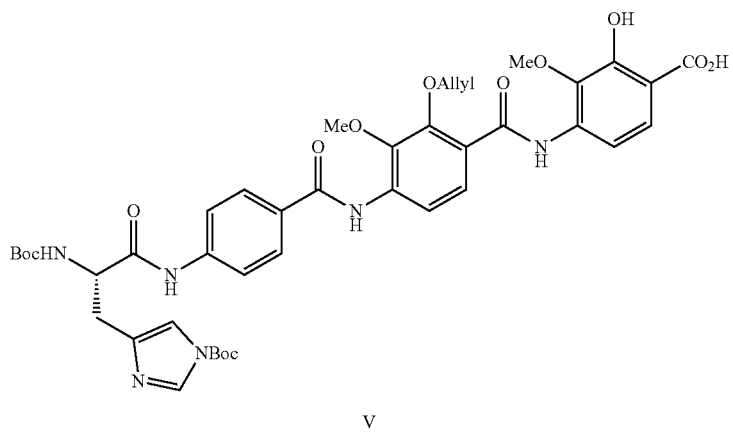

V

Tetrapeptide IV (1 eq, 0.16 mmol, 149.2 mg) was dissolved in THF (10 ml) and phenylsilane (8.04 eq, 1.30 mmol, 160 μL) and tetrakis(triphenylphosphin)palladium(0) (0.1 eq, 0.016 mmol, 19 mg) were added. The mixture was stirred for 2.5 h shielded from light. All volatiles were removed in vacuo and the residue was purified via flash chromatography on silica gel eluting with 5-20% methanol in DCM. Compound V (46.0 mg, 0.057 mmol, 35%) was obtained as a brown solid.

$^1$H NMR (DMSO-d$_6$, 400 MHz): $\delta$ (ppm)=11.79 (br. s, 1H), 10.88-10.94 (m, 1H), 10.50 (s, 1H), 9.62 (s, 1H), 8.13 (s, 1H), 7.96 (d, J=8.8 Hz, 2H), 7.79 (dd, J=8.8, 4.8 Hz, 3H), 7.68 (d, J=8.5 Hz, 1H), 7.55 (d, J=8.8 Hz, 1H), 7.49 (d, J=8.5 Hz, 1H), 7.28 (s, 1H), 7.13 (d, J=7.8 Hz, 1H), 4.39-4.46 (m, 1H), 3.87 (s, 3H), 3.79 (s, 3H), 2.90-2.97 (m, 1H), 2.82-2.90 (m, 1H), 1.55 (s, 9H), 1.34-1.38 (m, 9H).

$^{13}$C NMR (DMSO-d$_6$, 101 MHz): $\delta$ (ppm)=172.1, 171.1, 164.9, 163.6, 156.0, 155.3, 146.7, 142.3, 140.2, 139.3, 136.9, 136.7, 135.6, 134.5, 128.7, 125.1, 124.9, 118.7, 116.2, 114.5, 108.1, 85.2, 78.2, 60.5, 59.6, 56.0, 54.7, 48.6, 28.1, 27.4.

HRMS (ESI): m/z calc. for $C_{39}H_{44}N_6O_{13}$ [M+H]$^+$: 805.3039; Found 805.3041

Preparation of Compound VI
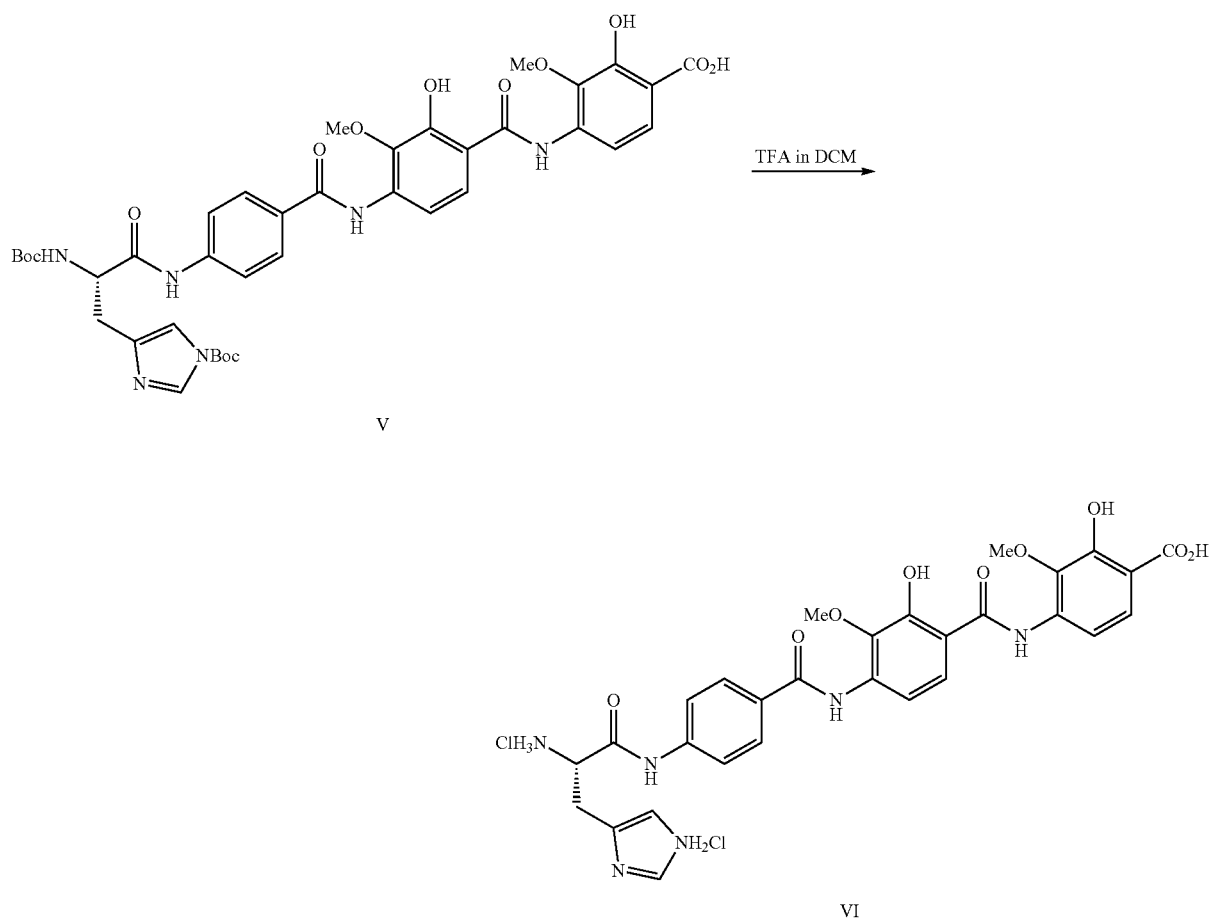
Tetrapeptide V (1 eq, 0.057 mmol, 46.0 mg) was dissolved in DCM (5 ml) and trifluoroacetic acid (2 ml) was added. After 3 h, all volatiles were removed in vacuo and compound VI (38.5 mg, 0.057 mmol, quant.) was used in the next step without further characterization.
HRMS (ESI): m/z cal. for $C_{29}H_{28}N_6O_9$ [M+H]$^+$: 605.1991; Found 605.2001
Preparation of Compound L-His-Albicidin
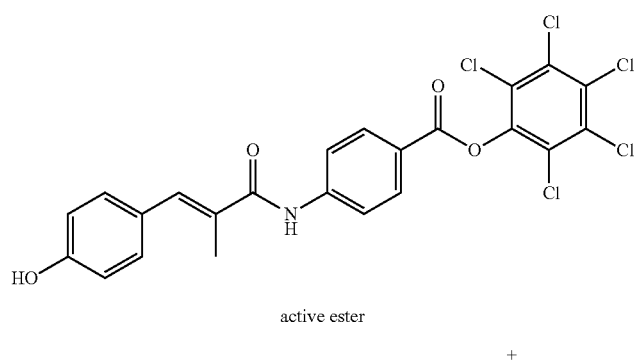
active ester
+

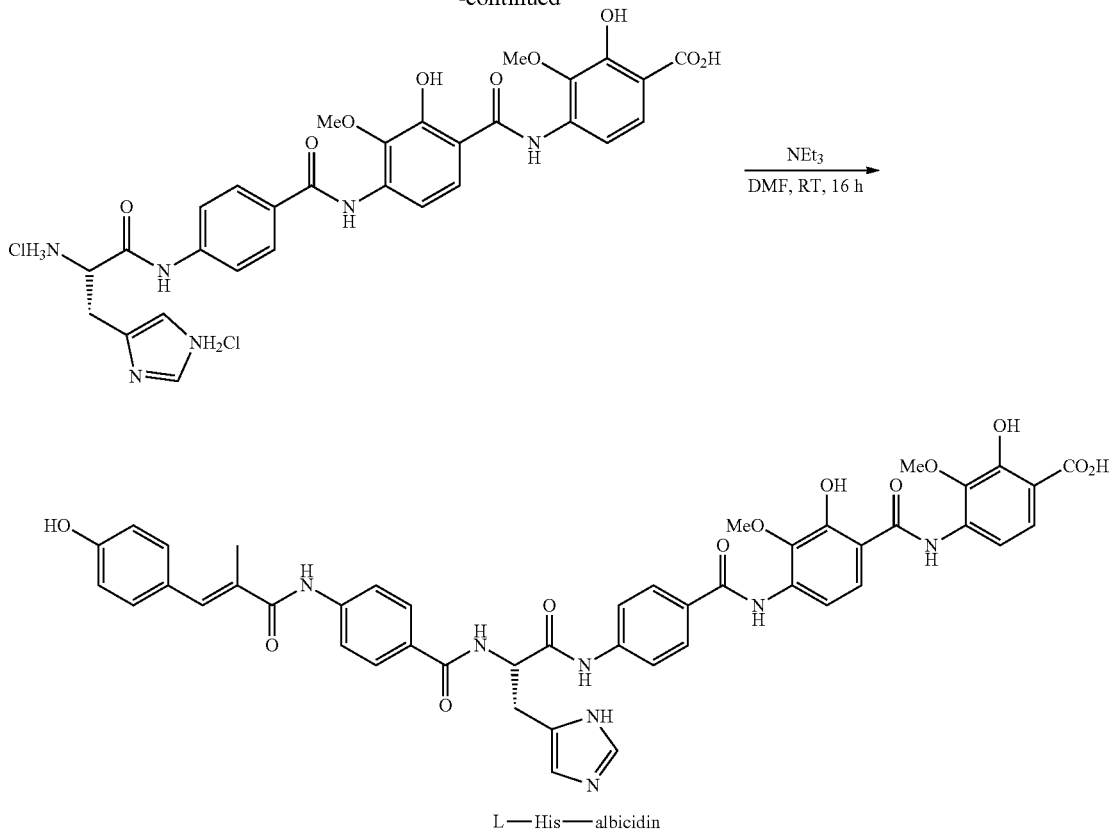

Compound VI (1 eq, 0.057 mmol, 38.5 mg) was dissolved in DMF (3 ml) and triethylamine (4.32 eq, 0.25 mmol, 34 µL) was added. After adding the active ester (1.52 eq, 0.086 mmol, 47.0 mg) (see reaction scheme), the mixture was stirred for 16 h shielded from light. All volatiles were removed in vacuo and the residue was purified via prep HPLC. L-His-Albicidin (18.0 mg, 0.021 mmol, 36%) was obtained as a white fluffy solid.

Analytical Data for L-his-Albicidin $^1$H NMR (DMSO-$d_6$, 400 MHz): δ (ppm)=11.54 (br. s, 1H), 11.17 (s, 1H), 10.46 (s, 1H), 10.10 (s, 1H), 9.80 (br. s., 1H), 9.69 (s, 1H), 8.98 (s, 1H), 8.79 (d, J=7.5 Hz, 1H), 8.05 (d, J=8.8 Hz, 1H), 7.99 (d, J=8.8 Hz, 2H), 7.85-7.90 (m, 2H), 7.83-7.84 (m, 1H), 7.80-7.82 (m, 2H), 7.78 (s, 1H), 7.58 (t, J=9.3 Hz, 2H), 7.43 (s, 1H), 7.35 (d, J=8.8 Hz, 2H), 7.26 (s, 1H), 6.84 (d, J=8.8 Hz, 2H), 4.91-4.99 (m, 1H), 3.91 (s, 3H), 3.78 (s, 3H), 3.29-3.37 (m, 1H), 3.19-3.26 (m, 1H), 2.11 (d, J=1.0 Hz, 3H).

HRMS (ESI): m/z calc. for $C_{46}H_{41}N_7O_{12}$ [M+H]$^+$: 884.2886; found 884.2891

The analytical data for the enantiomeric compound D-His-albicidin (compound 15), which was prepared in the same way, were identical.

The following compounds 2-11 were prepared in analogy to compound 1.

Compound 2: L-DMDAP-Albicidin

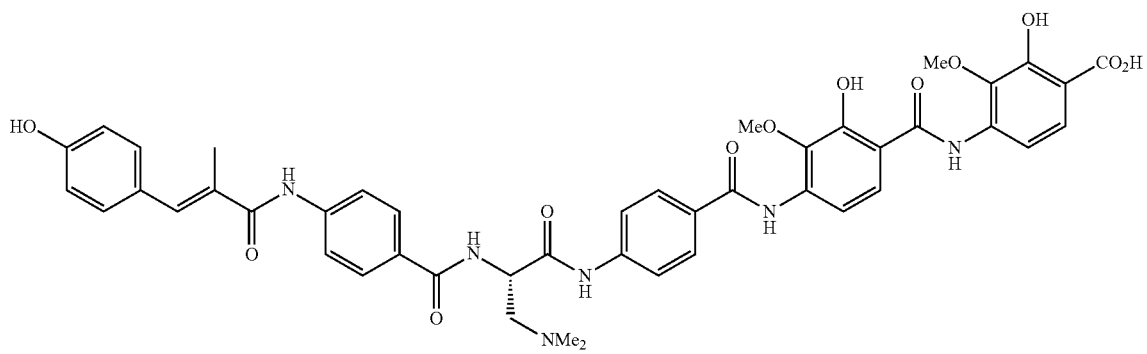

Corresponding tetrapeptide (1 eq, 0.19 mmol, 116.5 mg)
Active ester (1.20 eq, 0.23 mmol, 123.4 mg)
Triethylamin (2 eq, 0.38 mmol, 47 μL)
DMF (3 mL), reaction time: 16 h, purification via prep HPLC The described compound (36.0 mg, 0.042 mmol, 22%) was obtained as a white fluffy powder. The analytical data for the enantiomeric compound D-DMDAP-Albicidin (compound 16), which was prepared in the same way, were identical.

$^1$H NMR (DMSO-d$_6$, 400 MHz): δ (ppm)=11.15 (br. s, 1H), 10.71 (s, 1H), 10.11 (s, 1H), 9.57 (br. s., 1H), 8.54 (br. s., 1H), 7.97 (d, J=8.8 Hz, 2H), 7.90-7.94 (m, 2H), 7.85-7.89 (m, 1H), 7.82 (dd, J=8.7, 5.1 Hz, 4H), 7.77 (d, J=8.8 Hz, 1H), 7.65 (d, J=8.3 Hz, 1H), 7.49 (br. s., 1H), 7.44 (d, J=8.5 Hz, 1H), 7.35 (d, J=8.8 Hz, 2H), 7.27 (s, 1H), 6.85 (d, J=8.5 Hz, 2H), 4.77-4.84 (m, 1H), 3.85 (s, 3H), 3.79 (s, 3H), 2.29 (s, 6H), 2.11 (s, 3H).

HRMS (ESI): m/z ber. für C$_{45}$H$_{44}$N$_6$O$_{12}$ [M+H]$^+$: 861.3090; gef. 861.3104

Compound 3: L-Azahis-Albicidin

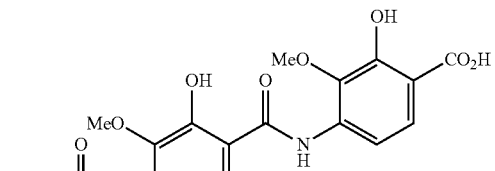

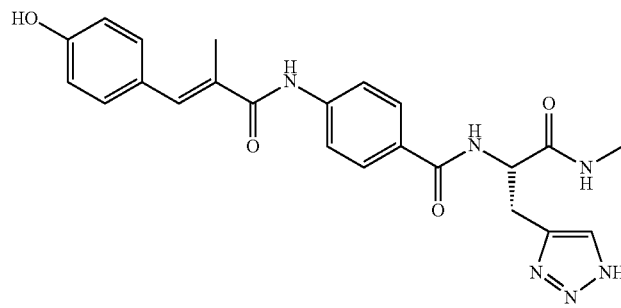

Corresponding POM-protected tetrapeptide (1 eq, 0.122 mmol, 93 mg)
Active ester (1.5 eq, 0.184 mmol, 100 mg)
Triethylamine (5 eq, 0.61 mmol, 86 μL)
DMF (3 mL), reaction time: 16 h, purification via prep HPLC After the alkylation reaction was finished (proven via LCMS analysis) the POM-protecting group of the triazole was removed without further analysis.

The described compound (36 mg, 0.035 mmol, 29%) was obtained as a white fluffy powder.

$^1$H NMR (DMSO-d$_6$, 400 MHz): δ (ppm)=11.57-11.64 (m, 1H), 11.54 (s, 1H), 11.19 (s, 1H), 10.53 (s, 1H), 10.09 (s, 1H), 9.69 (s, 1H), 8.72 (d, J=7.5 Hz, 1H), 8.06 (d, J=8.8 Hz, 1H), 7.97 (d, J=8.8 Hz, 2H), 7.84-7.90 (m, 2H), 7.76-7.83 (m, 5H), 7.69 (s, 1H), 7.59 (dd, J=8.9, 5.6 Hz, 2H), 7.35 (d, J=8.8 Hz, 2H), 7.26 (s, 1H), 6.84 (d, J=8.5 Hz, 2H), 4.86-4.96 (m, 1H), 3.91 (s, 3H), 3.78 (s, 3H), 3.28 (d, J=8.0 Hz, 2H), 2.11 ppm (d, J=1.3 Hz, 3H).

HRMS (ESI): m/z ber. für C$_{45}$H$_{40}$N$_8$O$_{12}$ [M+H]$^+$: 885.2838; gef. 885.2834

Compound 4: L-Morpholino-Albicidin

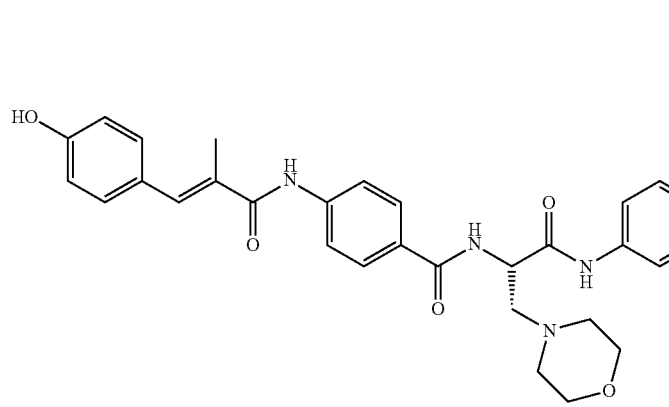

Corresponding tetrapeptide (1 eq, 0.08 mmol, 51 mg)
Active ester (1.3 eq, 0.1 mmol, 55 mg)
Triethylamine (5 eq, 0.386 mmol, 54 μL)
DMF (3 mL), reaction time: 16 h, purification via prep HPLC The described compound (14 mg, 0.016 mmol, 20%) was obtained as a white fluffy powder.

$^1$H NMR (DMSO-$d_6$, 400 MHz): δ (ppm)=11.55 (s, 1H), 11.17 (s, 1H), 10.58-10.64 (m, 1H), 10.12 (s, 1H), 9.77-9.82 (m, 1H), 9.70 (s, 1H), 8.80-8.89 (m, 1H), 8.05 (d, J=8.9 Hz, 1H), 8.00 (d, J=8.7 Hz, 2H), 7.90-7.96 (m, 3H), 7.82-7.88 (m, 3H), 7.77-7.82 (m, 3H), 7.54-7.62 (m, 3H), 7.35 (d, J=8.7 Hz, 2H), 7.27 (s, 1H), 6.84 (d, J=8.6 Hz, 2H), 5.01-5.09 (m, 1H), 3.91 (s, 4H), 3.78 (s, 3H), 2.11 ppm (d, J=0.9 Hz, 3H)

HRMS (ESI): m/z ber. für $C_{47}H_{46}N_6O_{13}$ $[M+H]^+$: 903.3196; gef. 903.3192

Compound 5: L-Methyl-His-Albicidin

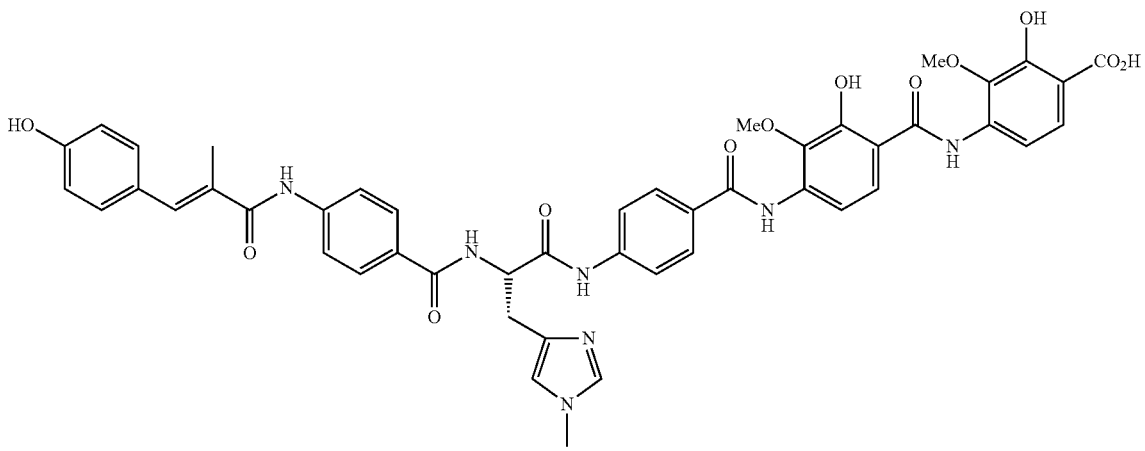

Corresponding tetrapeptide (1 eq, 0.204 mmol, 134 mg)
Active ester (1.6 eq, 0.327 mmol, 178 mg)
Triethylamine (7 eq, 1.43 mmol, 196 μL)
DMF (3 mL), reaction time: 16 h, purification via prep HPLC The described compound (17 mg, 0.019 mmol, 9%) was obtained as a white fluffy powder.

$^1$H NMR (DMSO-$d_6$, 400 MHz): δ (ppm)=11.57 (br. s., 1H), 11.19 (s, 1H), 10.50 (s, 1H), 10.12 (s, 1H), 9.78-9.87 (m, 1H), 9.72 (s, 1H), 8.94 (s, 1H), 8.81 (d, J=7.8 Hz, 1H), 8.06 (d, J=9.0 Hz, 1H), 7.99 (d, J=8.8 Hz, 2H), 7.86-7.91 (m, 2H), 7.76-7.85 (m, 5H), 7.58 (dd, J=12.0, 8.8 Hz, 2H), 7.46 (s, 1H), 7.35 (d, J=8.8 Hz, 2H), 7.26 (s, 1H), 6.84 (d, J=8.5 Hz, 2H), 4.87-4.96 (m, 1H), 3.91 (s, 3H), 3.80 (s, 3H), 3.77 (s, 3H), 3.17-3.33 (m, 2H), 2.11 ppm (d, J=1.0 Hz, 3H)

HRMS (ESI): m/z ber. für $C_{47}H_{43}N_7O_{12}$ $[M+H]^+$: 898.3042; gef. 898.3053

Compound 6: N-Methylpiperidino-Albicidin

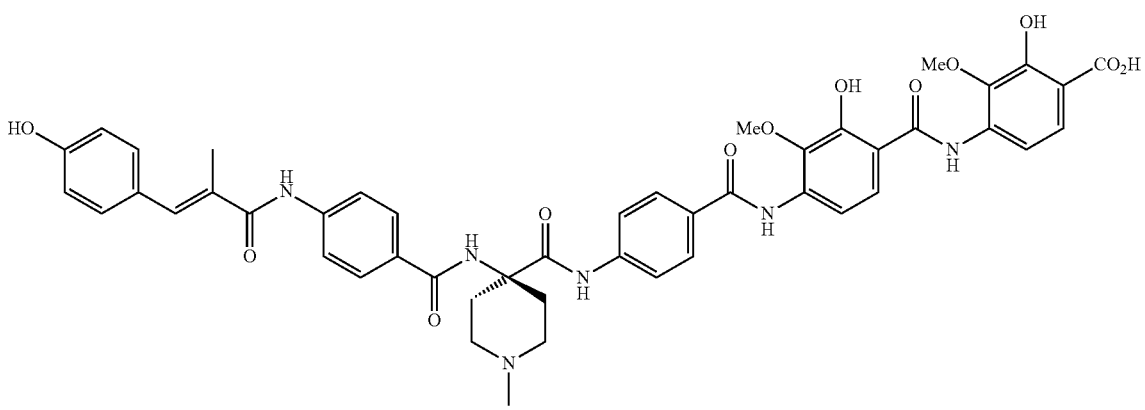

Corresponding tetrapeptide (1 eq, 0.254 mmol, 167 mg)
Active ester (1.35 eq, 0.331 mmol, 180 mg)
Triethylamine (6 eq, 1.47 mmol, 207 µL)
DMF (3 mL), reaction time: 16 h, purification via prep HPLC The described compound (22 mg, 0.025 mmol, 10%) was obtained as a white fluffy powder.

$^1$H NMR (DMSO-d$_6$, 400 MHz): δ (ppm)=11.52 (br. s., 1H), 11.16 (s, 1H), 10.09 (s, 1H), 9.92-9.95 (m, 1H), 9.74-9.81 (m, 1H), 9.65 (s, 1H), 8.56-8.60 (m, 1H), 8.39-8.42 (m, 1H), 8.04 (s, 1H), 7.97 (dd, J=15.5, 8.6 Hz, 4H), 7.85 (d, J=8.8 Hz, 2H), 7.81 (d, J=8.8 Hz, 2H), 7.72 (d, J=8.5 Hz, 2H), 7.59 (d, J=9.0 Hz, 1H), 7.53-7.57 (m, 1H), 7.35 (d, J=8.5 Hz, 2H), 7.28 (s, 1H), 6.84 (d, J=8.3 Hz, 2H), 3.91 (s, 3H), 3.74-3.79 (m, 3H), 3.46 (d, J=10.2 Hz, 8H), 2.12 ppm (s, 3H)

HRMS (ESI): m/z ber. für C$_{47}$H$_{46}$N$_6$O$_{12}$ [M+H]$^+$: 887.3246; gef. 887.3245

Compound 7: L-2-Py-Albicidin

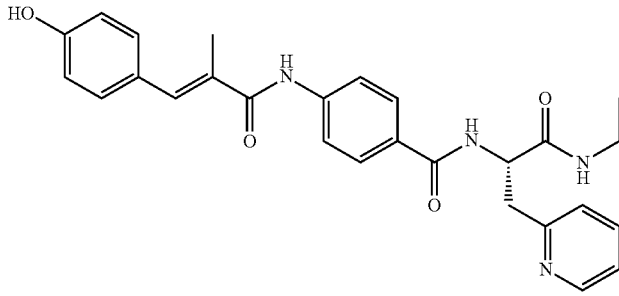

Corresponding tetrapeptide (1 eq, 0.290 mmol, 200 mg)
Active ester (1.10 eq, 0.320 mmol, 174 mg)
Triethylamine (5.00 eq, 1.45 mmol, 200 µL)
DMF (12 mL), reaction time: 16 h, purification via prep HPLC The described compound (195 mg, 0.218 mmol, 75%) was obtained as a fluffy white powder.

$^1$H NMR (DMSO-d$_6$, 700 MHz): δ (ppm)=10.59 (s, 1H), 10.09 (s, 1H), 9.84 (s, 1H), 9.56 (br. s, 1H), 8.76 (d, J=7.6 Hz, 1H), 8.54-8.52 (m, 1H), 7.96 (d, J=8.6 Hz, 2H), 7.84-7.82 (m, 2H), 7.82-7.78 (m, 4H), 7.78-7.75 (m, 2H), 7.72 (td, J$_1$=7.6 Hz, J$_2$=1.7 Hz, 2H), 7.63 (d, J=7.2 Hz, 1H), 7.45-7.40 (m, 2H), 7.50 (br. s, 1H), 7.35 (d, J=8.5 Hz, 2H), 7.26 (s, 1H), 7.23 (dd, J$_1$=7.1 Hz, J$_2$=5.2 Hz, 1H), 6.85 (d, J=8.5 Hz, 2H), 5.09 (q, J=7.5 Hz, 1H), 3.85 (s, 3H), 3.79 (s, 3H), 3.00 (br. s., 2H), 2.11 (s, 3H).

HRMS (ESI): m/z ber. für C$_{48}$H$_{41}$N$_6$O$_{12}$ [M-H]$^-$: 893.2782; gef. 893.2772

Compound 8

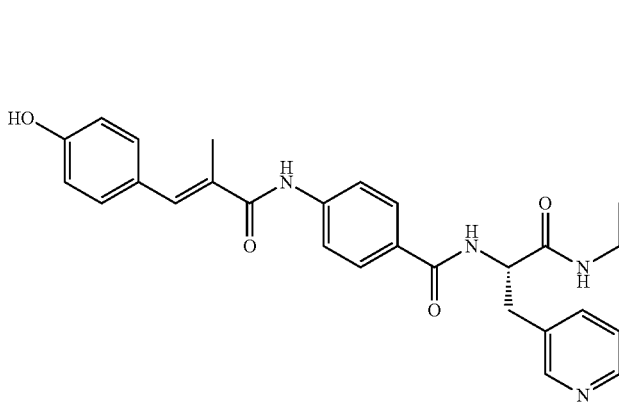

Corresponding tetrapeptide (1 eq, 0.145 mmol, 100 mg)
Active ester (1.16 eq, 0.169 mmol, 92.0 mg)
Triethylamine (5.29 eq, 0.767 mmol, 110 µL)
DMF (6 mL), reaction time: 16 h, purification via prep HPLC The described compound (15.0 mg, 0.017 mmol, 12%) was obtained as a fluffy white powder.

$^1$H NMR (DMSO-d$_6$, 500 MHz): δ (ppm)=11.51 (s, 1H), 11.15 (s, 1H), 10.55 (s, 1H), 10.05 (s, 1H), 9.74 (s, 1H), 9.66 (s, 1H), 8.75 (d, J=7.9 Hz, 1H), 8.05 (d, J=8.9 Hz, 1H), 7.99 (d, J=8.9 Hz, 2H), 7.88 (br.s, 1H), 7.85-7.81 (m, 2H), 7.81-7.75 (m, 4H), 7.59 (dd, J$_1$=8.8 Hz, J$_2$=2.5 Hz, 2H), 7.41 (br.s, 1H), 7.35 (d, J=8.5 Hz, 2H), 7.26 (s, 1H), 6.84 (d, J=8.7 Hz, 2H), 4.90 (br.s, 1H), 3.91 (s, 3H), 3.78 (s, 3H), 2.10 (d, J=1.2 Hz, 3H).

HRMS (ESI): m/z ber. für C$_{48}$H$_{43}$N$_6$O$_{12}$ [M+H]$^+$: 895.2933; gef. 895.2914

Compound 9

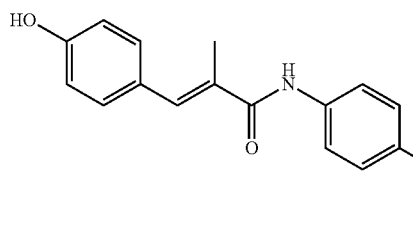
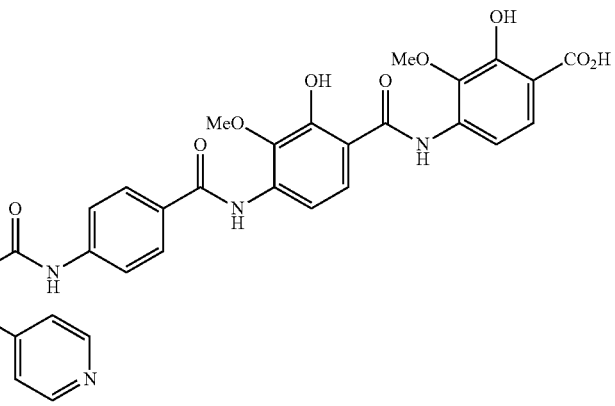

Corresponding tetrapeptide (1 eq, 0.119 mmol, 82.0 mg)
Active ester (1.16 eq, 0.138 mmol, 75.5 mg)
Triethylamine (5.29 eq, 0.629 mmol, 88.4 µL)
DMF (5 mL), reaction time: 16 h, purification via prep HPLC The described compound (5.00 mg, 0.017 mmol, 10%) was obtained as a fluffy white powder.

$^1$H NMR (DMSO-d$_6$, 500 MHz): δ (ppm)=11.55 (s, 1H), 11.16 (s, 1H), 10.59 (s, 1H), 10.07 (s, 1H), 9.78 (s, 1H), 9.68 (s, 1H), 8.79-8.73 (m, 1H), 8.07-7.97 (m, 4H), 7.86-7.77 (m, 7H), 7.76-7.70 (m, 1H), 7.62-7.44 (m, 5H), 7.38-7.33 (m, 2H), 7.26 (s, 1H), 6.87-6.82 (m, 2H), 5.00-4.93 (m, 1H), 3.92 (s, 3H), 3.79 (s, 3H), 2.10-2.07 (m, 3H)

HRMS (ESI): m/z ber. für C$_{48}$H$_{43}$N$_6$O$_{12}$ [M+H]$^+$: 895.2933; gef. 895.2935

Compound 10

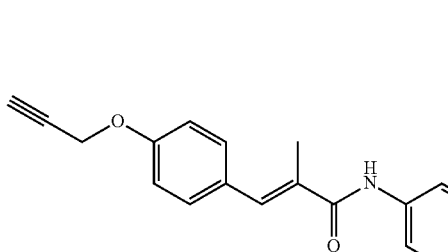
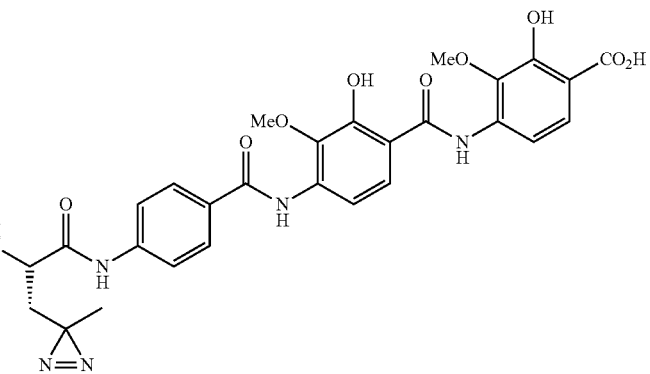

Corresponding tetrapeptide (1 eq, 44 μmol, 26 mg)
Succinimidyl active ester of Building block AB (2 eq, 88 μmol, 38 mg)
Triethylamine (3 eq, 132 μmol, 18 μL)
DMF (5 mL), reaction time: 16 h, purification via prep HPLC The described compound (18.7 mg, 20.7 μmol, 47%) was obtained as a fluffy white powder.

$^1$H-NMR (400 MHz, DMSO-$d_6$): δ (ppm)=1.12 (s, 3H), 1.99 (d, J=7.52 Hz, 2H), 2.14 (d, J=0.81 Hz, 3H), 3.61 (t, J=2.28 Hz, 1H), 3.78 (s, 3H), 3.92 (s, 3H), 4.53 (q, J=7.79 Hz, 1H), 4.86 (d, J=2.15 Hz, 2H), 7.08 (d, J=8.60 Hz, 2H), 7.32 (s, 1H), 7.48 (d, J=8.60 Hz, 1H), 7.59 (dd, J=8.87, 4.57 Hz, 1H), 7.76-7.88 (m, 4H), 7.96 (dd, J=14.37, 8.73 Hz, 3H), 8.06 (d, J=8.87 Hz, 1H), 8.66 (d, J=7.52 Hz, 1H), 9.68 (s, 1H), 10.15 (s, 1H), 10.54 (s, 1H), 10.81-10.88 (m, 1H), 11.18 (s, 1H), 11.49-12.29 (m, 1H), 11.54 (s, 1H), 11.56-11.71 (br, 1H), 13.33-14.56 (br, 1H).

$^{13}$C-NMR (101 MHz, DMSO-$d_6$): δ (ppm)=172.1, 170.5, 168.7, 166.1, 164.9, 163.3, 157.0, 154.4, 149.7, 142.4, 142.2, 140.2, 137.9, 136.1, 136.0, 133.2, 131.0, 128.9, 128.8, 128.7, 128.4, 128.3, 125.7, 125.5, 119.2, 118.8, 116.2, 114.9, 110.3, 109.0, 79.1, 78.4, 60.5, 60.2, 55.5, 50.4, 35.8, 24.6, 19.8, 14.5

HRMS (ESI): m/z berechnet $C_{48}H_{43}N_7O_{12}$ [M+H]$^+$: 910.3042; gefunden 910.3049.

Compound 11

$^{13}$C-NMR (101 MHz, DMSO-$d_6$): δ (ppm)=172.0, 170.5, 166.0, 165.2, 164.9, 163.3, 159.9, 154.4, 149.7, 142.3, 142.2, 140.2, 137.9, 136.1, 136.0, 129.7, 128.8, 128.8, 128.5, 128.4, 127.4, 125.7, 125.5, 119.3, 118.8, 116.2, 114.9, 114.6, 110.3, 109.0, 78.9, 78.6, 60.5, 60.2, 55.6, 50.4, 35.8, 24.6, 19.8

HRMS (ESI): m/z berechnet $C_{45}H_{39}N_7O_{12}$ [M+H]$^+$: 870.2729; gefunden 870.2741.

Compound 12 is obtained in a synthesis procedure according to reaction scheme 2. Compound 12 is synthesized in a multistep synthesis route in analogy to the following reaction route:

Allyl-2-(allyloxy)-4-nitrobenzoate (VII)

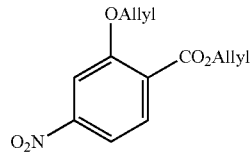

Commercially available 2-Hydroxy-4-nitrobenzoic acid (1.00 eq, 27.32 mmol, 5.0 g) was dissolved in DMF (150 mL) and $K_2CO_3$ (4.00 eq, 109.28 mmol, 15.1 g) and allyl

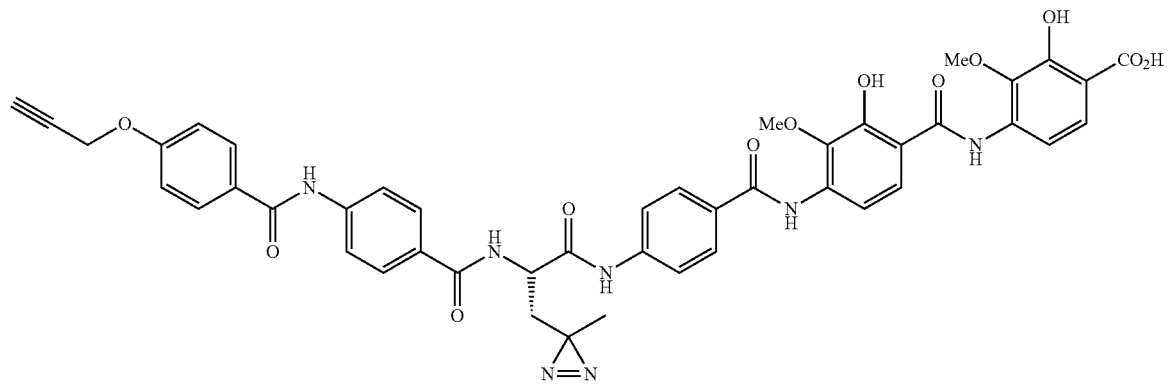

Corresponding tetrapeptide (1 eq, 42 μmol, 25 mg)
Succinimidyl active ester of Building block AB (1.5 eq, 63 μmol, 25 mg)
Triethylamine (3 eq, 127 μmol, 18 μL)
DMF (5 mL), reaction time: 16 h, purification via prep HPLC The described compound (25 mg, 28.7 μmol, 68%) was obtained as a fluffy white powder.

$^1$H-NMR (400 MHz, DMSO-$d_6$): δ (ppm)=1.12 (s, 3H), 1.99 (d, J=7.79 Hz, 2H), 3.63 (t, J=2.28 Hz, 1H), 3.78 (s, 3H), 3.89-3.95 (m, 3H), 4.48-4.58 (m, 1H), 4.92 (d, J=2.42 Hz, 2H), 7.14 (d, J=8.87 Hz, 2H), 7.59 (dd, J=8.87, 4.30 Hz, 2H), 7.79 (d, J=8.86 Hz, 2H), 7.82 (s, 1H), 7.91 (d, J=9.13 Hz, 2H), 7.94-8.02 (m, 6H), 8.05 (d, J=8.87 Hz, 1H), 8.67 (d, J=7.79 Hz, 1H), 9.68 (s, 1H), 10.36 (s, 1H), 10.53 (s, 1H), 11.18 (s, 1H), 11.53 (s, 1H), 11.58-11.68 (m, 1H), 13.42-14.50 (m, 1H).

bromide (3.00 eq, 81.96 mmol, 7.1 mL) were added. The reaction mixture was stirred at rt for 22 h and diluted with ethyl acetate (300 mL). The organic fraction was washed with brine (3×150 ml), dried over $Na_2SO_4$, filtered and evaporated. Purification via flash chromatography eluting with hexanes/ethyl acetate 13:1 yielded compound 1 (6.5 g, 90%) as a colorless oil.

$^1$H-NMR (400 MHz, DMSO-$d_6$): δ (ppm)=4.79-4.80 (m, 4H), 5.24-5.30 (m, 2H), 5.37-5.48 (m, 2H), 5.95-6.07 (m, 2H), 7.84-7.89 (m, 3H).

$^{13}$C-NMR (101 MHz, DMSO-$d_6$): δ (ppm)=65.7, 69.5, 108.6, 115.4, 117.7, 118.3, 126.5, 131.6, 132.2, 132.5, 150.3, 157.1, 164.4.

HRMS (ESI): m/z calc. for $C_{13}H_{14}NO_5^+$ [M+H]$^+$ 264.0866, found 264.0866.

2-(Allyloxy)-4-nitrobenzoic acid (VIII)

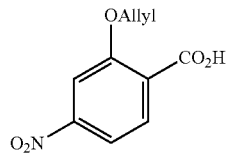

Compound VII (1.00 eq, 3.72 mmol, 980 mg) was dissolved in THF (50 mL), dist. water (50 mL) and methanol (50 mL). KOH (5.00 eq, 18.58 mmol, 1.0 g) was added. The reaction mixture was stirred for 23 h at rt. The organic solvents were removed by rotary evaporation. The remaining aqueous phase was treated with 5% aqueous hydrochloric acid, until a pH of ~1 was reached. The resulting precipitate was filtered, washed with 5% aqueous hydrochloric acid and dried in vacuo to yield VIII (775 mg, 94%) as a white solid.

$^1$H-NMR (400 MHz, DMSO-$d_6$): δ (ppm)=4.78 (d, J=4.5 Hz, 2H), 5.26-5.29 (m, 1H), 5.44-5.49 (m, 1H), 5.98-6.07 (m, 1H), 7.80-7.84 (m, 3H).

$^{13}$C-NMR (101 MHz, DMSO-$d_6$): δ (ppm)=69.3, 108.4, 115.3, 117.6, 128.4, 131.1, 132.7, 149.8, 156.8, 166.4.

HRMS (ESI): m/z calc. for $C_{10}H_8NO_5^-$ [M−H]$^-$ 222.0397, found 222.0399.

Allyl-2-(allyloxy)-4-aminobenzoate (IX)

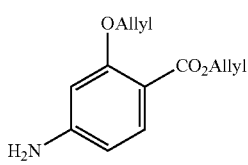

Compound VII (1.00 eq, 3.80 mmol, 1.0 g) was dissolved in ethanol (30 ml) and $SnCl_2$*$2H_2O$ (5.00 eq, 19.01 mmol, 4.3 g) was added. The reaction mixture was heated to 60° C. and stirred for 4 h. After the evaporation of ethanol via rotary evaporation, the residue was taken up in ethyl acetate (100 ml) and saturated aqueous $NaHCO_3$-Solution. The aqueous fraction was further extracted with ethyl acetate (2×100 ml). The combined organic fractions were washed with brine (1×100 ml), dried over $Na_2SO_4$, filtered and evaporated. Purification via flash chromatography eluting with hexanes/ethyl acetate 3:1 yielded compound IX (779 mg, 88%) as a red oil.

$^1$H-NMR (500 MHz, DMSO-$d_6$): δ (ppm)=4.50 (d, J=4.16 Hz, 2H), 4.65 (d, J=5.15 Hz, 2H), 5.20-5.26 (m, 2H), 5.34-5.56 (m, 2H), 5.89-6.07 (m, 4H), 6.16-6.21 (m, 2H), 7.56 (d, J=8.52 Hz, 1H).

$^{13}$C-NMR (125 MHz, DMSO-$d_6$): δ (ppm)=64.2, 68.6, 98.0, 105.9, 106.2, 117.1, 117.4, 133.9, 134.1, 155.1, 160.8, 165.0.

HRMS (ESI): m/z calc. for $C_{13}H_{16}NO_3^+$ [M+H]$^+$ 234.1125, found 234.1115.

$O_2N$-HpABA(Allyl)-HpABA(Allyl)-OAllyl (X)

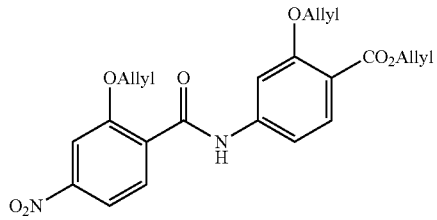

BTC (0.66 eq, 0.57 mmol, 168 mg) and the benzoic acid VIII (2.00 eq, 1.72 mmol, 383 mg) were dissolved in THF (10 ml) under an atmosphere of argon. 2,4,6-Collidine (8.00 eq, 6.84 mmol, 910 µL) was slowly added via syringe and the resulting suspension was stirred 15 min at room temperature. The amine IX (1.00 eq, 0.86 mmol, 200 mg) and DIPEA (10.00 eq, 8.58 mmol, 1.5 mL) were dissolved in THF (10 ml) under an atmosphere of argon and added to the suspension via syringe. The resulting solution was stirred 16 h at room temperature and the reaction was quenched by the addition of water. After separation of the organic layer the aqueous layer was extracted with ethyl acetate (3×20 ml). The combined organic layers were washed with brine (1×30 ml), dried over $Na_2SO_4$, filtered and the solvent was removed in vacuo. Purification via flash chromatography eluting with hexanes/ethyl acetate 5:1 yielded compound X (345 mg, 92%) as a white solid.

$^1$H-NMR (500 MHz, DMSO-$d_6$): δ (ppm)=4.61 (d, J=4.7 Hz, 2H), 4.75 (d, J=5.3 Hz, 2H), 4.84 (d, J=4.7 Hz, 2H), 5.25-5.30 (m, 3H), 5.40-5.55 (m, 3H), 5.93-6.10 (m, 3H), 7.35 (d, J=10.1 Hz, 1H), 7.63 (d, J=1.3 Hz, 1H), 7.78 (d, J=8.5 Hz, 1H), 7.81 (d, J=8.9 Hz, 1H), 7.93-7.94 (m, 2H), 10.69 (s, 1H).

$^{13}$C-NMR (125 MHz, DMSO-$d_6$): δ (ppm)=65.1, 69.2, 70.0, 104.7, 108.5, 111.5, 115.2, 116.2, 117.7, 118.1, 118.3, 130.7, 132.4, 132.8, 133.1, 133.3, 133.4, 144.1, 149.8, 156.2, 158.9, 164.4, 165.0.

HRMS (ESI): m/z calc. for $C_{23}H_{23}N_2O_7^+$ [M+H]$^+$ 439.1500, found 439.1492.

H-HpABA(Allyl)-HpABA(Allyl)-OAllyl (XI)

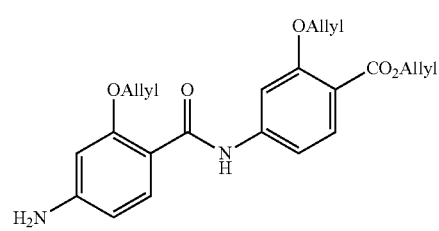

Compound X (1.00 eq, 0.78 mmol, 340 mg) was dissolved in ethanol (40 ml) and $SnCl_2$*$2H_2O$ (5.00 eq, 3.88 mmol, 875 mg) was added. The reaction mixture was heated to 60° C. and stirred for 6 h. After the evaporation of ethanol via rotary evaporation, the residue was taken up in ethyl acetate (50 ml) and saturated aqueous $NaHCO_3$-Solution. The aqueous fraction was further extracted with ethyl acetate (2×50 ml). The combined organic fractions were washed with brine (1×200 ml), dried over $Na_2SO_4$, filtered and evaporated. Purification via flash chromatography eluting with hexanes/ethyl acetate 2:1 yielded compound XI (216 mg, 68%). as a red solid.

$^1$H-NMR (400 MHz, DMSO-$d_6$): δ (ppm)=4.61 (d, J=4.5 Hz, 2H), 4.68 (d, J=5.6 Hz, 2H), 4.73 (d, J=5.1 Hz, 2H), 5.23-5.29 (m, 2H), 5.36-5.42 (m, 2H), 5.48-5.56 (m, 2H), 5.95 (s, 2H), 5.97-6.11 (m, 2H), 6.17-6.30 (m, 3H), 7.24 (dd, $J_1$=8.6 Hz, $J_2$=1.8 Hz, 1H), 7.61-7.64 (m, 2H), 7.74 (d, J=8.6 Hz, 1H), 10.08 (s, 1H).

$^{13}$C-NMR (101 MHz, DMSO-$d_6$): δ (ppm)=64.5, 68.5, 69.0, 97.0, 103.8, 106.7, 108.9, 110.7, 113.4, 117.1, 117.5, 118.9, 132.3, 132.7, 132.9, 133.0, 144.4, 154.1, 157.9, 158.6, 163.9, 164.5.

HRMS (ESI): m/z calc. for $C_{23}H_{25}N_2O_5^+$ [M+H]$^+$ 409.1758, found 409.1748.

O$_2$N-pABA-L-Cya-PABA-HpABA(Allyl)-HpABA (Allyl)-OAllyl (XII)

BTC (1.15 eq, 0.57 mmol, 168 mg) and the literature known benzoic acid XIII (3.50 eq, 1.72 mmol, 659 mg) were dissolved in THF (20 ml) under an atmosphere of argon. 2,4,6-Collidine (8.00 eq, 3.94 mmol, 522 μL) was slowly added via syringe and the resulting suspension was stirred 15 min at room temperature. The amine XI (1.00 eq, 0.49 mmol, 201 mg) and DIPEA (10.00 eq, 4.92 mmol, 837 μL) were dissolved in THF (15 ml) under an atmosphere of argon and added to the suspension via syringe. The resulting solution was stirred 16 h at room temperature and the reaction was quenched by the addition of water. After separation of the organic layer the aqueous layer was extracted with ethyl acetate (3×20 ml). The combined organic layers were washed with brine (1×50 ml), dried over $Na_2SO_4$, filtered and the solvent was removed in vacuo. Purification via flash chromatography eluting with 1.5% methanol in DCM yielded compound XII (311 mg, 82%) as a brown oil.

$^1$H-NMR (500 MHz, DMSO-$d_6$): δ (ppm)=3.09 (dd, $J_1$=17.0 Hz, $J_2$=8.7 Hz, 1H), 3.17-3.22 (m, 1H), 4.62-4.63

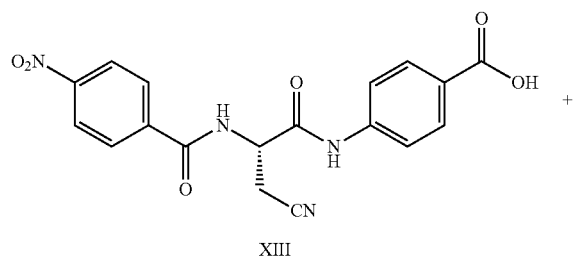

XIII

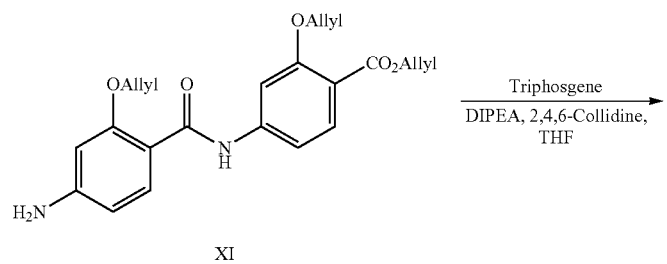

XI

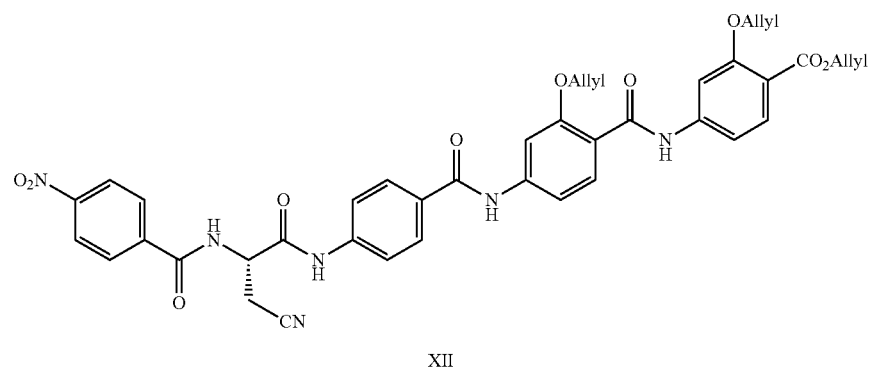

XII (m, 2H), 4.72-4.75 (m, 4H), 5.01-5.06 (m, 1H), 5.25-5.35 (m, 3H), 5.40-5.56 (m, 3H), 5.99-6.11 (m, 2H), 6.14-6.22 (m, 1H), 7.35 (d, J=8.5 Hz, 1H), 7.54 (d, J=9.9 Hz, 1H), 7.67 (s, 1H), 7.73-7.81 (m, 5H), 8.01 (d, J=8.7 Hz, 2H), 8.18 (d, J=8.5 Hz, 2H), 8.39-8.40 (m, 2H), 9.53 (d, J=7.7 Hz, 1H), 10.31 (s, 1H), 10.40 (s, 1H), 10.61 (s, 1H).

$^{13}$C-NMR (125 MHz, DMSO-d$_6$): δ (ppm)=19.9, 50.7, 64.5, 68.6, 69.1, 104.1, 104.4, 110.9, 112.2, 114.0, 117.2, 117.5, 118.1, 118.8, 118.9, 123.6, 128.8, 129.1, 129.3, 130.8, 132.3, 132.9, 133.0, 139.0, 141.7, 143.3, 144.1, 149.3, 156.1, 158.5, 164.2, 164.5, 165.0, 165.1, 167.6.

HRMS (ESI): m/z calc. for $C_{41}H_{37}N_6O_{10}^+$ [M+H]$^+$ 773.2566, found 773.2584.

H-pABA-L-Cya-PABA-HpABA(Allyl)-HpABA(Allyl)-OAllyl (XIV)

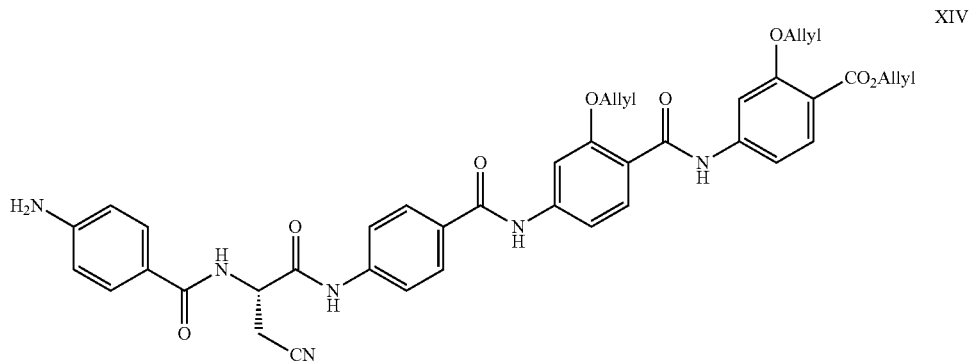

Compound XII (1.00 eq, 0.39 mmol, 304 mg) was dissolved in ethanol (50 ml) and SnCl$_2$*2H$_2$O (8.00 eq, 3.15 mmol, 710 mg) was added. The reaction mixture was heated to 60° C. and stirred for 9 h. After the evaporation of ethanol via rotary evaporation, the residue was taken up in ethyl acetate (50 ml) and saturated aqueous NaHCO$_3$-Solution (50 ml). The aqueous fraction was further extracted with ethyl acetate (2×50 ml). The combined organic fractions were washed with brine (1×200 ml), dried over Na$_2$SO$_4$, filtered and evaporated. Purification via flash chromatography eluting with 2.5% to 5% methanol in chloroform yielded compound XIV (167 mg, 57%) as a yellow oil.

$^1$H-NMR (500 MHz, DMSO-d$_6$): δ (ppm)=3.04 (dd, J$_1$=16.7 Hz, J$_2$=8.82 Hz, 1H), 3.10-3.14 (m, 1H), 4.62-4.63 (m, 2H), 4.72-4.75 (m, 4H), 4.91-4.96 (m, 1H), 5.25-5.35 (m, 3H), 5.40-5.56 (m, 3H), 5.74 (s, 2H), 5.99-6.11 (m, 2H), 6.14-6.22 (m, 1H), 6.59 (d, J=8.7 Hz, 2H), 7.35 (d, J=8.5 Hz, 1H), 7.54 (d, J=8.5 Hz, 1H), 7.67-7.68 (m, 3H), 7.73-7.80 (m, 5H), 8.00 (d, J=8.7 Hz, 2H), 8.61 (d, J=7.9 Hz, 1H), 10.31 (s, 1H), 10.39 (s, 1H), 10.51 (s, 1H).

$^{13}$C-NMR (125 MHz, DMSO-d$_6$): δ (ppm)=20.4, 51.0, 65.0, 69.1, 69.6, 104.6, 105.0, 111.4, 112.7, 113.0, 114.5, 117.7, 118.0, 118.8, 119.3, 120.3, 129.2, 129.6, 129.8, 131.3, 132.8, 133.4, 142.4, 143.9, 144.6, 152.7, 156.6, 159.0, 164.7, 165.0, 165.6, 167.1, 169.1.

HRMS (ESI): m/z calc. for $C_{41}H_{39}N_6O_8^+$ [M+H]$^+$ 743.2824, found 743.2827.

HMZS(Allyl)-pABA-L-Cya-pABA-HpABA(Allyl)-HpABA(Allyl)-OAllyl (XV)

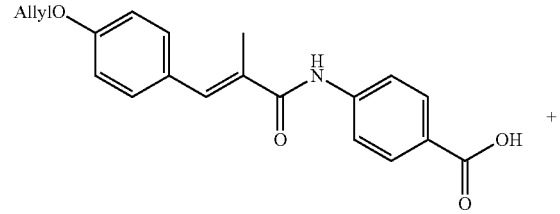

XVI

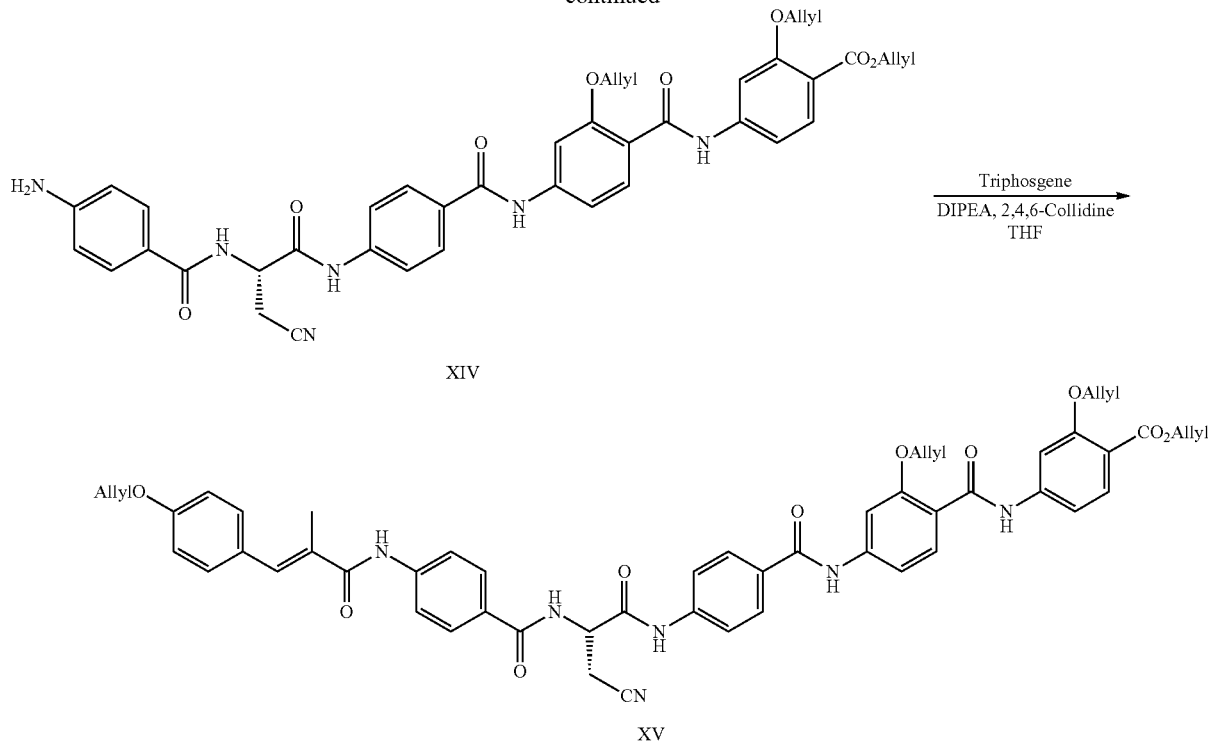

XIV

XV

BTC (1.00 eq, 0.09 mmol, 28 mg) and the literature known benzoic acid XVI (3.50 eq, 0.33 mmol, 72 mg) were dissolved in THF (15 ml) under an atmosphere of argon. 2,4,6-Collidine (8.00 eq, 0.75 mmol, 100 μL) was slowly added via syringe and the resulting suspension was stirred 15 min at room temperature. The amine XIV (1.00 eq, 0.09 mmol, 70 mg) and DIPEA (10.00 eq, 0.94 mmol, 160 μL) were dissolved in THF (20 ml) under an atmosphere of argon and added to the suspension via syringe. The resulting solution was stirred 16 h at room temperature and the reaction was quenched by the addition of water. After separation of the organic layer the aqueous layer was extracted with ethyl acetate (3×20 ml). The combined organic layers were washed with brine (1×30 ml), dried over $Na_2SO_4$, filtered and the solvent was removed in vacuo. Purification via flash chromatography eluting with 1.8% to 3% methanol in chloroform yielded compound XV (30 mg, 34%) as a white solid.

$^1$H NMR (400 MHz, DMSO-$d_6$): δ (ppm)=2.13 (s, 3H), 3.07 (dd, $J_1$=16.6 Hz, $J_2$=8.60 Hz, 1H), 3.14-3.19 (m, 1H), 4.61-4.63 (m, 4H), 4.71-4.75 (m, 4H), 4.95-5.01 (m, 1H), 5.24-5.35 (m, 4H), 5.38-5.56 (m, 4H), 5.97-6.22 (m, 4H), 7.04 (d, J=8.8 Hz, 2H), 7.31 (s, 1H), 7.34 (dd, $J_1$=8.6 Hz, $J_2$=1.6 Hz, 1H), 7.46 (d, J=8.8 Hz, 2H), 7.53 (dd, $J_1$=8.4 Hz, $J_2$=1.7 Hz, 1H), 7.66 (s, 1H), 7.71-7.81 (m, 5H), 7.86 (d, J=8.87 Hz, 2H), 7.92-7.95 (m, 2H), 8.00 (d, J=8.8 Hz, 2H), 9.06 (d, J=7.5 Hz, 1H), 10.16 (s, 1H), 10.32 (s, 1H). 10.40 (s, 1H). 10.61 (s, 1H).

HRMS (ESI): m/z calc. for $C_{54}H_{51}N_6O_{10}^+$ [M+H]$^+$ 943.3661, found 943.3656.

HMZS-pABA-L-Cya-pABA-HpABA-HpABA-OH

Compound XV (1.00 eq, 0.03 mmol, 28 mg) was dissolved in THF (5 ml) under an atmosphere of argon. After the addition of tetrakis(triphenylphosphine)palladium(0) (0.50 eq, 0.02 mmol, 17 mg) and phenylsilane (8.00 eq, 0.24 mmol, 29 μL) the reaction mixture was stirred for 4 h in the dark. The reaction was quenched with acetic acid. All volatiles were removed in vacuo and the residue was dissolved in methanol, filtered and purified by means of preparative HPLC. Compound 12 (5 mg, 21%) was obtained as a white fluffy solid.

$^1$H-NMR (700 MHz, DMSO-d$_6$): δ (ppm)=2.12 (s, 3H), 3.07 (dd, J$_1$=16.9 Hz, J$_2$=8.8 Hz, 1H), 3.14-3.18 (m, 1H), 4.79-5.00 (m, 1H), 6.64 (d, J=8.4 Hz, 1H), 6.85 (d, J=8.4 Hz, 2H), 7.28 (s, 1H), 7.35-7.36 (m, 4H), 7.50 (s, 1H), 7.55-7.56 (m, 1H), 7.71-7.72 (m, 2H), 7.76-7.80 (m, 2H), 7.85 (d, J=8.6 Hz, 2H), 7.93 (d, J=8.7 Hz, 2H), 7.99 (d, J=8.6 Hz, 2H), 9.02 (d, J=7.4 Hz, 1H), 9.79 (s, 1H), 10.12 (s, 1H), 10.36-10.38 (m, 2H), 10.46 (s, 1H), 10.57 (s, 1H), 11.85 (s, 1H). $^{13}$C-NMR (from HSQC, 175 MHz, DMSO-d$_6$): δ (ppm)=14.8, 20.5, 50.9107.6, 108.9, 111.5, 111.9, 119.2, 119.6, 128.1, 128.4, 129.2, 131.3, 131.6, 134.2, 134.8.

HRMS (ESI): m/z calc. for C$_{42}$H$_{33}$N$_6$O$_{10}$$^-$ [M–H]$^-$ 804.2511, found 804.2517.

Compound 13

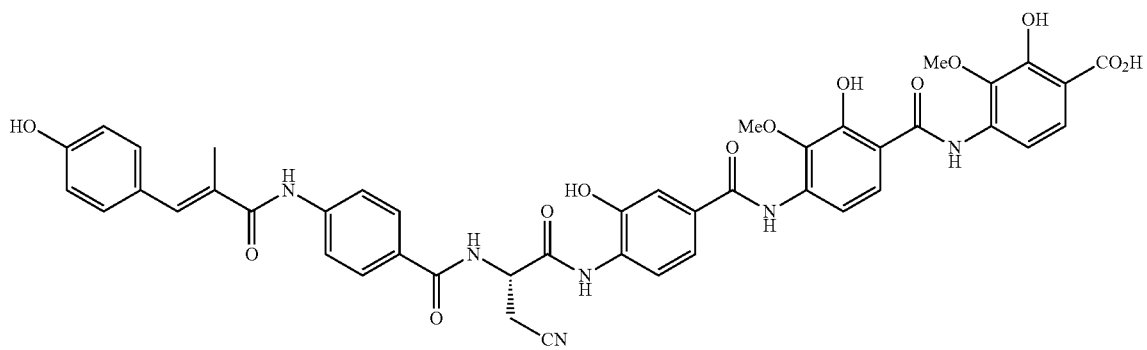

Due to the small amount of material no NMR-spectra were recorded.

HRMS (ESI): m/z calc. for C$_{44}$H$_{38}$N$_6$O$_{13}$$^-$ [M–H]$^-$ 857,24241, found 857,24260.

Compound 14

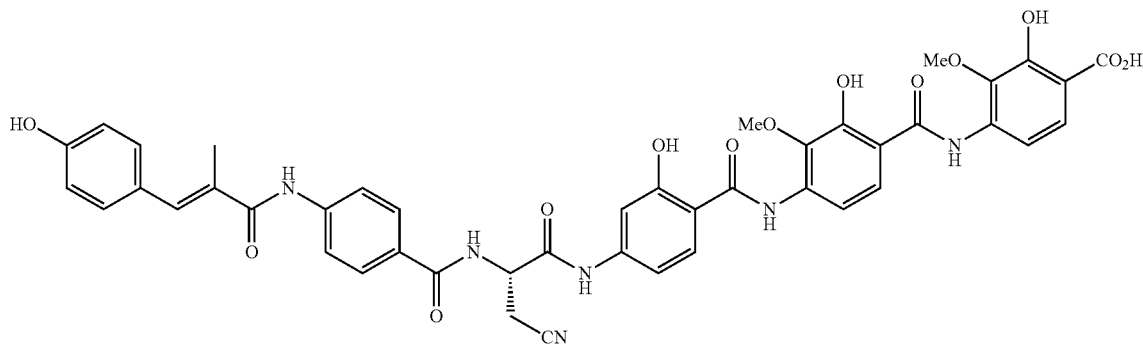

Due to the small amount of material no NMR-spectra were recorded.
HRMS (ESI): m/z calc. for $C_{44}H_{38}N_6O_{13}^+$ [M+H]$^+$ 859.2570, found 859.2565.
Compound 17
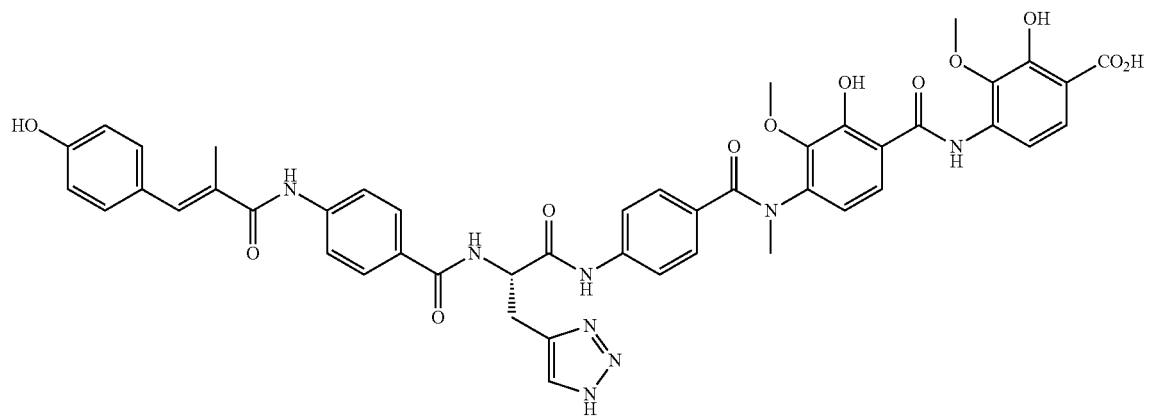
$^1$H NMR (DMSO-d$_6$, 400 MHz): δ=11.56 (br. s, 1H), 11.48 (s, 1H), 11.12 (s, 1H), 10.27 (s, 1H), 10.05 (s, 1H), 9.76 (br. s, 1H), 8.61 (d, J=7.5 Hz, 1H), 8.02 (d, J=8.8 Hz, 2H), 7.85-7.75 (m, 5H), 7.64 (br. s, 1H), 7.57 (d, J=8.8 Hz, 1H), 7.47 (d, J=8.5 Hz, 2H), 7.34 (d, J=8.5 Hz, 2H), 7.32 (d, J=8.5 Hz, 2H), 7.25 (s, 1H), 7.04 (d, J=8.8 Hz, 1H), 6.84 (d, J=8.5 Hz, 2H), 4.84-4.78 (m, 1H), 3.85 (s, 3H), 3.69 (s, 3H), 3.36 (s, 3H), 3.24-3.13 (m, 2H), 2.10 (s, 3H)
HRMS (ESI): m/z calc. for $C_{46}H_{43}N_8O_{12}^+$ [M+H]$^+$ 899.3000, found 899.2994.
Compound 18
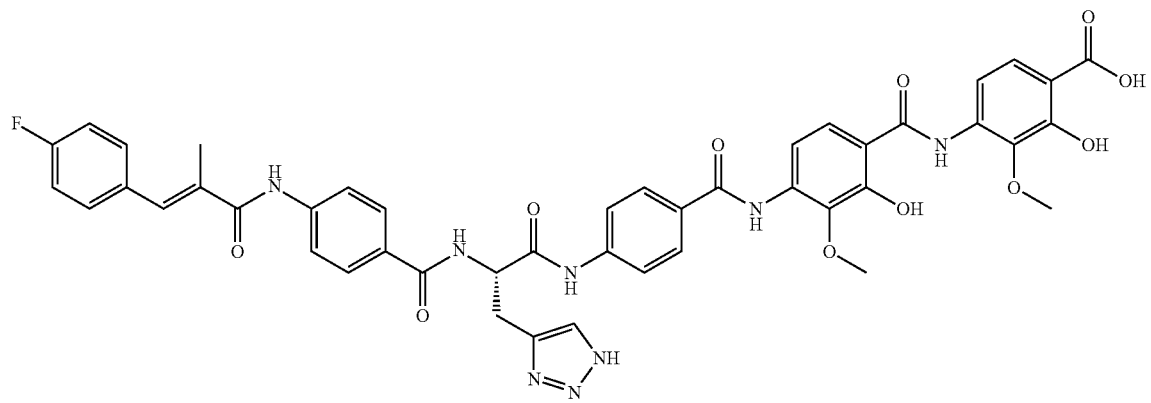

¹H NMR (DMSO-d₆, 400 MHz): δ=11.59 (br. s, 1H), 11.54 (s, 1H), 11.19 (s, 1H), 10.53 (s, 1H), 10.18 (s, 1H), 9.68 (s, 1H), 8.73 (d, J=7.8 Hz, 1H), 8.06 (d, J=8.8 Hz, 1H), 7.97 (d, J=8.8 Hz, 2H), 7.86-7.90 (m, 2H), 7.76-7.84 (m, 4H), 7.69 (s, 1H), 7.51-7.61 (m, 2H), 7.33 (s, 1H), 7.26-7.32 (m, 2H), 4.87-4.96 (m, 1H), 3.91 (s, 3H), 3.78 (s, 3H), 3.19-3.34 (m, 2H), 2.11 ppm (s, 3H)
HRMS (ESI): m/z calc. for $C_{45}H_{39}FN_8O_{11}^+$ [M+H]⁺ 887.2795, found 887.2792.
Compound 19
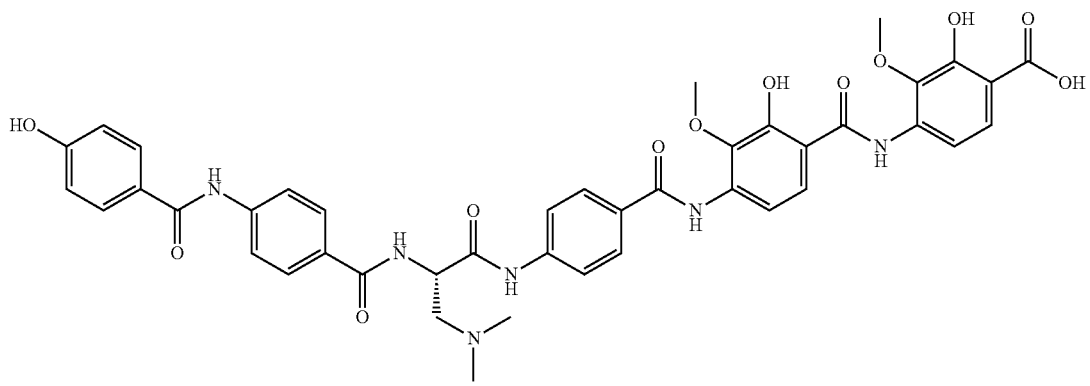 [SMILES: COc1c(NC(=O)c2ccc(NC(=O)c3ccc(NC(=O)[C@H](CN(C)C)NC(=O)c4ccc(NC(=O)c5ccc(O)cc5)cc4)cc3)c(OC)c2O)ccc(C(=O)O)c1O]
¹H NMR (DMSO-d₆, 400 MHz): δ=11.56 (s, 1H), 11.18 (s, 1H), 10.63 (s, 1H), 10.27 (s, 1H), 10.20 (s, 1H), 9.73 (s, 1H), 8.93 (d, J=8.8 Hz, 1H), 8.05 (d, J=9.0 Hz, 1H), 8.01 (d, J=8.8 Hz, 2H), 7.90-7.98 (m, 4H), 7.88 (d, J=8.8 Hz, 2H), 7.76-7.83 (m, 3H), 7.59 (d, J=8.8 Hz, 1H), 7.55 (d, J=8.8 Hz, 1H), 6.88 (d, J=8.3 Hz, 2H), 5.09-5.20 (m, 1H), 3.91 (s, 3H), 3.77 (s, 3H), 3.04-3.12 (m, 2H), 2.91 ppm (br. s, 6H)
HRMS (ESI): m/z calc. for $C_{42}H_{40}N_6O_{12}^+$ [M+H]⁺ 821.2777, found 821.2802.
Compound 20
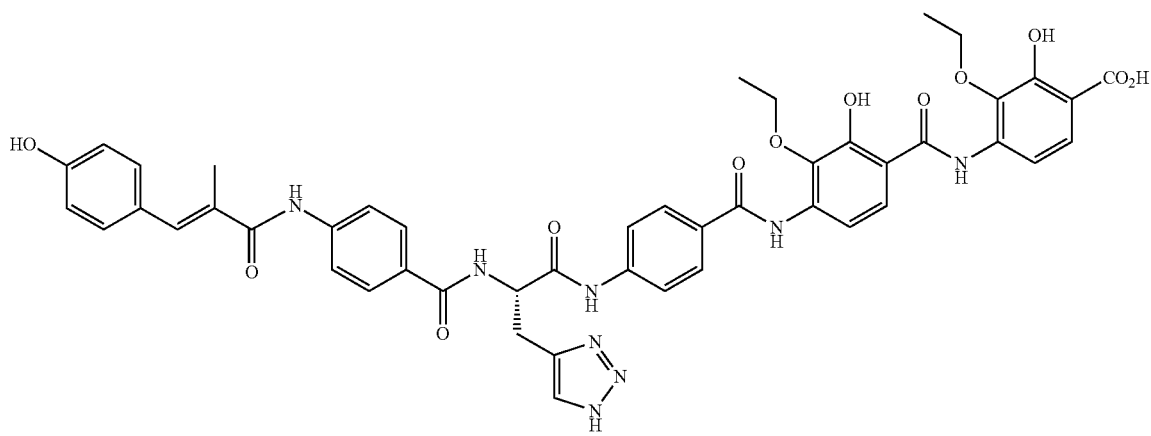 [SMILES: CCOc1c(NC(=O)c2ccc(NC(=O)c3ccc(NC(=O)[C@H](Cc4c[nH]nn4)NC(=O)c4ccc(NC(=O)/C(C)=C/c5ccc(O)cc5)cc4)cc3)c(OCC)c2O)ccc(C(=O)O)c1O]

¹H NMR (DMSO-d₆, 400 MHz): δ=11.63 (br. s, 1H), 11.42 (s, 1H), 11.08 (s, 1H), 10.54 (s, 1H), 10.10 (s, 1H), 9.79 (br. s, 1H), 9.63 (s, 1H), 8.72 (d, J=7.3 Hz, 1H), 8.06 (d, J=9.0 Hz, 1H), 7.97 (d, J=8.8 Hz, 2H), 7.92-7.75 (m, 7H), 7.69 (br. s, 1H), 7.61-7.54 (m, 2H), 7.35 (d, J=8.5 Hz, 2H), 7.26 (s, 1H), 6.84 (d, J=8.5 Hz, 2H), 4.96-4.86 (m, 1H), 4.17 (q, J=7.0 Hz, 2H), 4.00 (q, J=7.0 Hz, 2H), 3.36-3.19 (m, 2H), 2.11 (s, 3H), 1.37 (t, J=7.0 Hz, 3H), 1.32 (t, J=7.0 Hz, 3H).
HRMS (ESI): m/z calc. for $C_{47}H_{45}N_8O_{12}^+$ [M+H]⁺ 913.3157, found 913.3151.
Compound 21
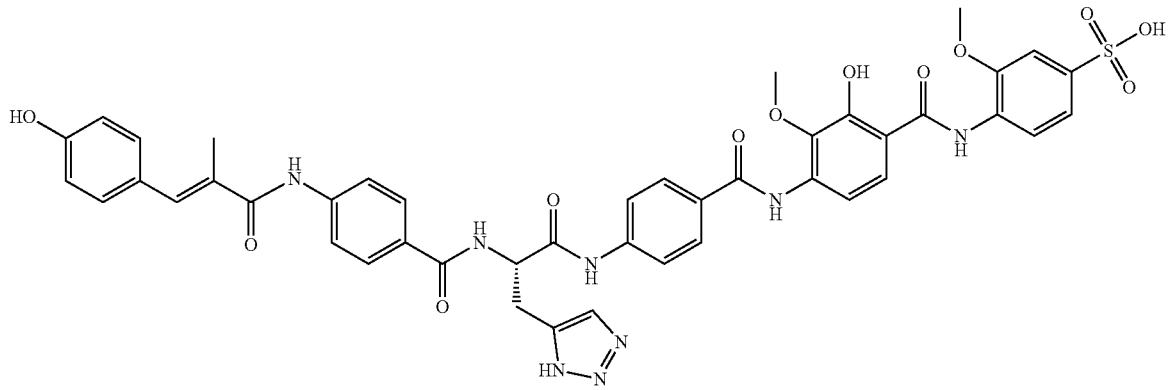 [SMILES: COc1cc(S(=O)(=O)O)ccc1NC(=O)c1ccc(NC(=O)c2ccc(NC(=O)[C@H](Cc3cnn[nH]3)NC(=O)c3ccc(NC(=O)/C(C)=C/c4ccc(O)cc4)cc3)cc2)c(OC)c1O]
¹H NMR (DMSO-d₆, 700 MHz): δ=11.80 (s, 1H), 10.64 (s, 1H), 10.50 (s, 1H), 10.07 (s, 1H), 9.75 (br. s, 1H), 9.59 (s, 1H), 8.69 (d, J=7.5 Hz, 1H), 8.10 (d, J=8.1 Hz, 1H), 7.97 (d, J=8.8 Hz, 2H), 7.85-7.88 (m, 2H), 7.80-7.83 (m, 3H), 7.78 (d, J=8.5 Hz, 2H), 7.68 (br. s, 1H), 7.58 (d, J=8.8 Hz, 1H), 7.35 (d, J=8.5 Hz, 2H), 7.27 (d, J=7.5 Hz, 2H), 7.22 (d, J=8.1 Hz, 1H), 6.84 (d, J=8.5 Hz, 2H), 4.89-4.94 (m, 1H), 3.90 (s, 3H), 3.80 (s, 3H), 3.27-3.32 (m, 1H), 3.21-3.26 (m, 1H), 2.11 ppm (s, 3H)
HRMS (ESI): m/z calc. for $C_{44}H_{40}N_8O_{12}S^+$ [M+H]⁺ 905.2559, found 905.2568.
Compound 22
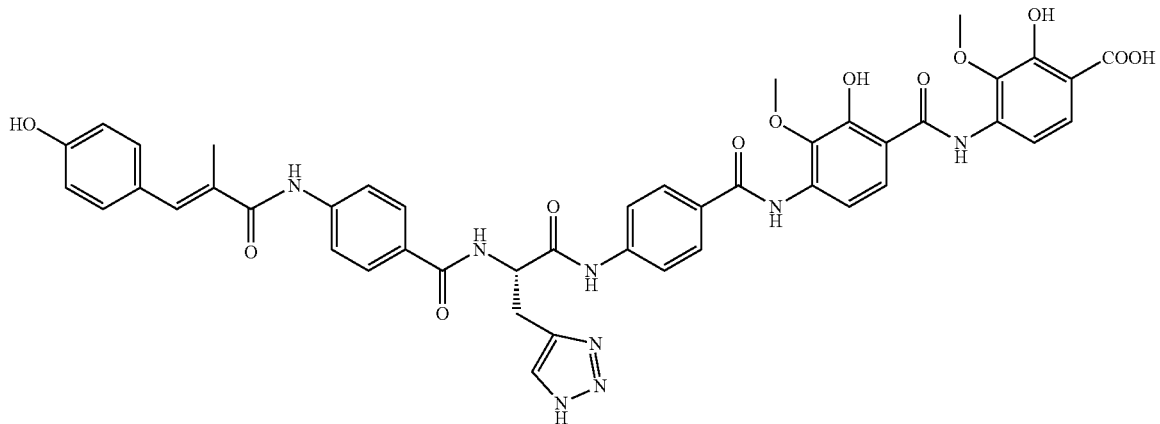 [SMILES: COc1c(NC(=O)c2ccc(NC(=O)c3ccc(NC(=O)[C@H](Cc4c[nH]nn4)NC(=O)c4ccc(NC(=O)/C(C)=C/c5ccc(O)cc5)cc4)cc3)c(OC)c2O)ccc(C(=O)O)c1O]

¹H NMR (DMSO-d₆, 700 MHz): δ=11.58 (br. s, 1H), 11.55 (s, 1H), 11.19 (s, 1H), 10.06 (s, 1H), 9.92 (br. s, 1H), 9.76 (br. s, 1H), 8.62 (br. s, 1H), 8.02-8.08 (m, 3H), 7.77-7.85 (m, 5H), 7.60 (d, J=8.8 Hz, 1H), 7.49-7.56 (m, J=8.8 Hz, 3H), 7.35 (d, J=8.7 Hz, 2H), 7.25 (s, 1H), 6.84 (d, J=8.7 Hz, 2H), 4.78 (br. s, 1H), 3.92 (s, 3H), 3.79 (s, 3H), 3.24 (br. s, 3H), 3.08 (br. s, 2H), 2.11 ppm (d, J=1.1 Hz, 3H)
HRMS (ESI): m/z calc. for $C_{46}H_{42}N_8O_{12}^+$ [M+H]⁺ 899.2995, found 899.2996
Compound 23
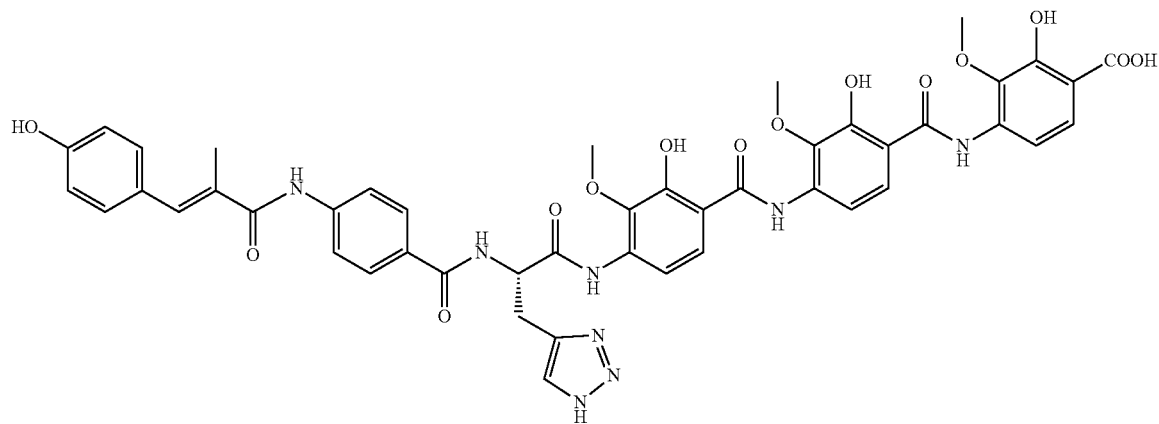 [SMILES: COc1c(NC(=O)c2ccc(NC(=O)c3ccc(NC(=O)[C@H](Cc4c[nH]nn4)NC(=O)c4ccc(NC(=O)/C(C)=C/c5ccc(O)cc5)cc4)c(OC)c3O)c(OC)c2O)ccc(C(=O)O)c1O]
¹H NMR (DMSO-d₆, 700 MHz): δ=11.62 (s, 1H), 11.58 (s, 1H), 11.13 (s, 1H), 11.03 (s, 1H), 10.09 (s, 1H), 9.76 (br. s, 1H), 9.65 (s, 1H), 8.89 (d, J=7.4 Hz, 1H), 8.02-8.07 (m, 2H), 7.86-7.89 (m, 2H), 7.79-7.85 (m, 5H), 7.71 (br. s, 1H), 7.59 (d, J=8.8 Hz, 1H), 7.35 (d, J=8.8 Hz, 2H), 7.26 (s, 1H), 6.84 (d, J=8.5 Hz, 2H), 5.05-5.11 (m, 1H), 3.91 (s, 3H), 3.83 (s, 3H), 3.69 (s, 3H), 3.34-3.39 (m, 1H), 3.24-3.30 (m, 1H), 2.11 ppm (d, J=1.1 Hz, 3H)
HRMS (ESI): m/z calc. for $C_{46}H_{42}N_8O_{14}^+$ [M+H]⁺ 931.2893, found 931.2893.
Compound 24
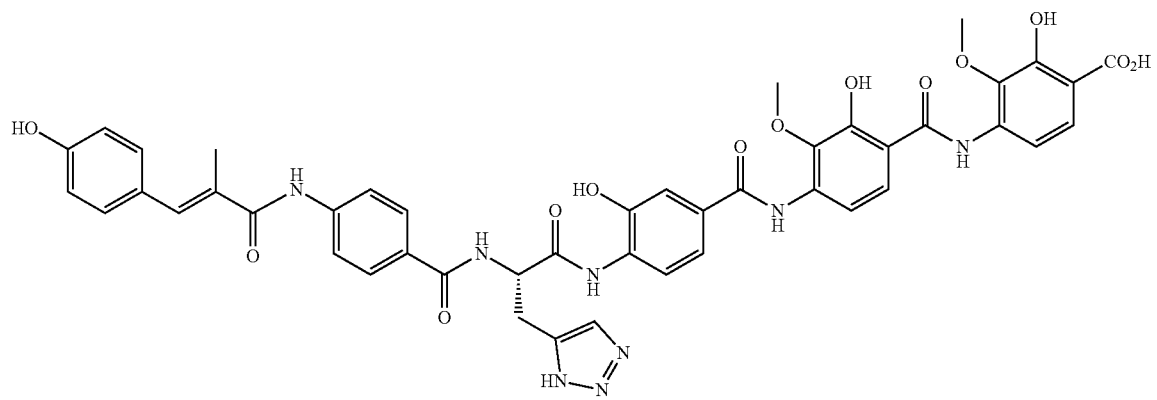 [SMILES: COc1c(NC(=O)c2ccc(NC(=O)c3ccc(NC(=O)[C@H](Cc4cnn[nH]4)NC(=O)c4ccc(NC(=O)/C(C)=C/c5ccc(O)cc5)cc4)c(O)c3)c(OC)c2O)ccc(C(=O)O)c1O]

¹H NMR (DMSO-d₆, 700 MHz): δ=11.52 (s, 1H), 11.16 (s, 1H), 11.03-11.05 (m, 1H), 10.46 (br. s, 1H), 10.09 (s, 1H), 9.76 (br. s, 1H), 9.53-9.59 (m, 1H), 9.37-9.41 (m, 1H), 8.86 (d, J=8.1 Hz, 1H), 8.19 (s, 1H), 8.05 (d, J=9.0 Hz, 1H), 7.84-7.87 (m, 3H), 7.79-7.84 (m, 4H), 7.68 (br. s, 1H), 7.59 (dd, J=8.9, 4.8 Hz, 2H), 7.35 (d, J=8.5 Hz, 2H), 7.26 (s, 1H), 6.84 (d, J=8.5 Hz, 2H), 5.00-5.04 (m, 1H), 3.91 (s, 3H), 3.76-3.79 (m, 3H), 3.35-3.40 (m, 1H), 3.23-3.28 (m, 1H), 2.11 (s, 2H), 2.10-2.12 ppm (m, 3H)

HRMS (ESI): m/z calc. for $C_{45}H_{40}N_8O_{13}^+$ [M+H]⁺ 901.2788, found 901.2788.

Compound 25

¹H NMR (DMSO-d₆, 500 MHz): δ=11.53 (s, 1H), 11.17 (s, 1H), 10.52 (s, 1H), 9.66 (s, 1H), 8.92 (d, J=7.8 Hz, 2H), 8.05 (d, J=9.2 Hz, 1H), 7.97 (d, J=8.9 Hz, 2H), 7.92 (d, J=8.5 Hz, 2H), 7.81 (d, J=8.9 Hz, 1H), 7.78 (d, J=8.9 Hz, 2H), 7.68 (br. s, 1H), 7.63 (d, J=8.4 Hz, 3H), 7.59 (dd, J=8.9, 4.6 Hz, 2H), 7.53 (d, J=8.9 Hz, 2H), 7.01 (d, J=9.0 Hz, 2H), 4.93 (m, 1H), 3.92 (s, 3H), 3.81 (s, 3H), 3.78 (s, 3H), 3.34-3.21 (m, 2H).

HRMS (ESI): m/z calc. for $C_{44}H_{38}N_7O_{11}^+$ [M+H]⁺ 840.2623, found 840.2629.

Test for Biological Activity

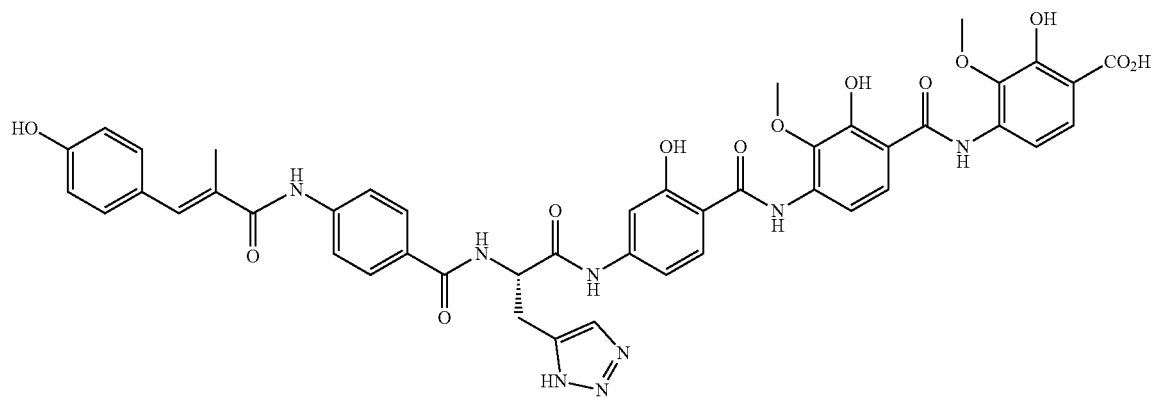 [SMILES: COc1c(NC(=O)c2ccc(NC(=O)c3ccc(NC(=O)[C@H](Cc4cnn[nH]4)NC(=O)c4ccc(NC(=O)/C(C)=C/c5ccc(O)cc5)cc4)cc3O)c(OC)c2O)ccc(C(=O)O)c1O]

¹H NMR (DMSO-d₆, 700 MHz): δ=11.91 (s, 1H), 11.57 (s, 1H), 11.12 (s, 1H), 11.08 (s, 1H), 10.46 (s, 1H), 10.07-10.15 (m, 1H), 9.76 (br. s, 1H), 8.68 (d, J=7.5 Hz, 1H), 8.16 (d, J=8.8 Hz, 1H), 8.03 (d, J=8.7 Hz, 1H), 7.97 (d, J=8.7 Hz, 1H), 7.79-7.91 (m, 5H), 7.68 (br. s, 1H), 7.62 (s, 1H), 7.59 (d, J=8.8 Hz, 1H), 7.35 (d, J=8.5 Hz, 2H), 7.26 (s, 1H), 7.16 (d, J=8.7 Hz, 1 H), 6.84 (d, J=8.4 Hz, 2H), 4.86-4.92 (m, 1H), 3.91 (s, 3H), 3.82 (s, 3H), 3.25-3.30 (m, 1H), 3.20-3.25 (m, 1H), 2.10-2.12 ppm (m, 3H)

HRMS (ESI): m/z calc. for $C_{45}H_{40}N_8O_{13}^+$ [M+H]⁺ 901.2788, found 901.2791.

Compound 26

Strains

*E. coli* DSM 1116; *S. typhimurium* TA100; *Bacillus subtilis* DSM10; and *Micrococcus luteus* DSM1790

Biological Testing

The tests were performed using the micro dilution method.

Microdilution Assay

The determination of MIC values was performed according to the ninth edition of the Approved Standard M07-A9

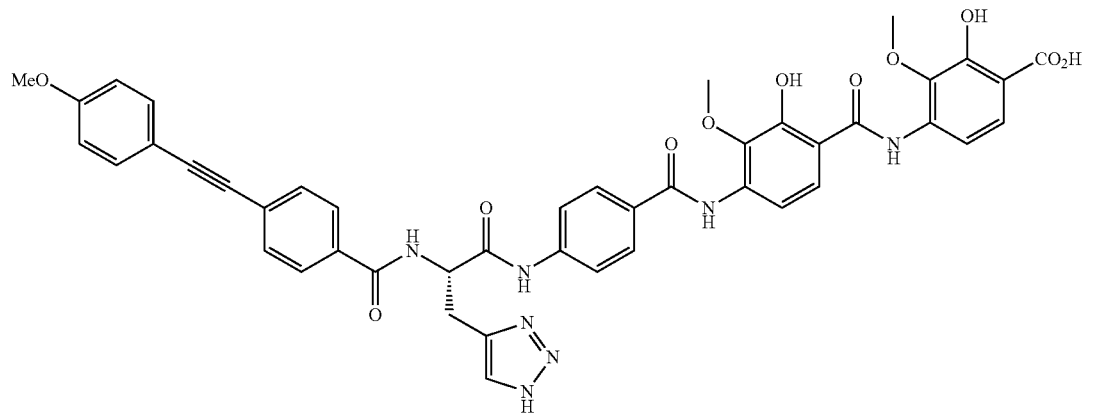 [SMILES: COc1ccc(C#Cc2ccc(C(=O)N[C@@H](Cc3c[nH]nn3)C(=O)Nc3ccc(C(=O)Nc4ccc(C(=O)Nc5ccc(C(=O)O)c(O)c5OC)c(O)c4OC)cc3)cc2)cc1]

(CLSI. Methods for Dilution Antimicrobial Susceptibility Tests for Bacteria That Grow Aerobically; Approved Standard—Ninth Edition. CLSI document M07-A9. Wayne, Pa.: Clinical and Laboratory Standards Institute; 2012.)

The test was carried out for four different bacterial strains (*E. coli* DSM 1116 [gram negative], *B. subtilis* DSM 10 [gram positive], *M. luteus* DSM 1790 [gram positive], *S. typhimurium* TA100 [gram negative]). 20 µL of cryo stock of each strain were inoculated in 20 mL of LB media (Lysogeny broth: 10 g/L peptone, 5 g/L yeast extract, 5 g/L NaCl) followed by incubation over night at 37° C., 200 rpm. The test inoculum was adjusted by the 0.5 McFarland Standard (OD625 from 0.08 to 0.1). Within 15 min of preparation, the adjusted inoculum suspension was diluted in MHBII media (BBL T M Mueller-Hinton Broth II, Becton, Dickinson and Company, N.J./USA) so that each well contained approximately 5×105 CFU/mL in a final volume of 100 µL. 95 µL of the inoculum were applied per well and 5 µL of the (diluted) antibiotic substance were added.

Previously the dry antibiotic compounds were dissolved in DMSO (100%) with a concentration of 2560 µg/mL and the resulting stock solutions were further diluted in DMSO (100%). 5 µL of each antibiotic dilution were applied to the microdilution tray to reach final concentrations of 64 µg/mL to 0.008 µg/mL. One row of each well plate was left as a growth control without antibiotic substances and another row of the microdilution tray was used as sterility control (only MHB II-media). The antimicrobial effect of the solvent (DMSO) was tested by adding 5 µL DMSO to several wells without antibiotics.

Purity check and cell titer control were performed according to International Standard M07-A9 on Mueller-Hinton II Agar (Mueller Hinton II Broth, 15 g/L agar-agar). Both microdilution trays and agar plates were incubated at 37° C. for 20 h and subsequently analyzed visually. The results are summarized in table 1.

TABLE 1

Antibacterial activity of compounds according to the solution against selected strains Compounds 1, 2, 3 and 16 were tested against a number of further strains. The results are summarized in Table 2.

| MIC [µg/µL] | *E. coli* DSM1116 | *S. typhimurium* TA100 | *B. subtilis* DSM10 | *M. luteus* DSM1790 |
|---|---|---|---|---|
| Albicidin | 0.063 | 0.063 | 0.25 | 1.0 |
| Compound 1 | 0.063 | 0.031 | 0.5 | 4.0 |
| Compound 2 | 0.125 | 0.031 | 0.125 | 2 |
| Compound 3 | ≤0.016 | ≤0.016 | 0.125 | 0.5 |
| Compound 4 | 0.5 | 0.063 | 0.25 | 8 |
| Compound 5 | 0.125 | 0.063 | 0.5 | 4.0 |
| Compound 6 | 2 | 2 | ≥8 | ≥8 |
| Compound 7 | 0.25 | 0.125 | 0.25 | 2 |
| Compound 8 | 0.25 | — | 0.5 | 1 |
| Compound 9 | 0.5 | 0.125 | 2 | 8 |
| Compound 10 | 0.063 | ≤0.016 | 0.125 | 0.25 |
| Compound 11 | 0.063 | 0.016 | 0.125 | 0.125 |
| Compound 12 | 16 | 4 | 128 | 32 |
| Compound 13 | 2 | 0.5 | 2 | — |
| Compound 14 | 0.031 | 0.016 | 0.25 | — |
| Compound 15 | 0.125 | 0.125 | 1.0 | 8 |
| Compound 16 | 0.5 | 0.25 | 1.0 | ≥8 |
| Compound 18 | 0.031 | ≤0.016 | 0.125 | 0.25 |
| Compound 19 | 2 | 0.5 | 4 | ≥8 |
| Compound 20 | 0.016 | 0.016 | 0.031 | 0.5 |
| Compound 22 | ≥8 | 2 | ≥8 | ≥8 |
| Compound 23 | ≥8 | 2 | ≥8 | ≥8 |
| Compound 24 | 0.125 | 0.063 | 1 | 8 |
| Compound 25 | 0.031 | 0.016 | 0.25 | 4 |
| Compound 26 | 0.063 | ≤0.016 | 0.25 | 0.5 |

TABLE 2

ATCC strains were obtained from the American Type Culture Collection (ATCC). PEG-strains are clinical isolates that were collected during a study of the Paul-Ehrlich-Society for Chemotherapie e.V. (PEG) in 2010 and 2013/14. The strains without any further designations such as 100-2-49 are further clinical isolates obtained from a lab in Germany.

| | | | | MHK [mg/l] | | | |
|---|---|---|---|---|---|---|---|
| Nr. Strain | | KBE/ml | CIP | Compound 1 | Compound 3 | Compound 2 | Compound 16 |
| 1 *Escherichia coli* | ATCC 25922 | 2.80E+05 | 0.015 | 0.063 | 0.008 | 0.125 | 16 |
| | | | 0.004-0.015 | n.a. | n.a. | n.a. | n.a. |
| 2 *Escherichia coli* | 100-2-49 | 3.80E+05 | 32 | 0.5 | 0.063 | 32 | 32 |
| 3 *Escherichia coli* | 100-2-56 | | 32 | 2 | 0.25 | 32 | 32 |
| 4 *Klebsiella pneumoniae* | PEG-10-20-4 | | 0.063 | 32 | 32 | 32 | 32 |
| 5 *Klebsiella pneumoniae* | PEG-10-90-74 | 4.00E+05 | 32 | 32 | 32 | 32 | 32 |
| 6 *Pseudomonas aeruginosa* | ATCC 27853 | 5.60E+05 | 0.5 | 2 | 1 | 32 | 32 |
| | | | 0.25-1 | n.a. | n.a. | n.a. | n.a. |
| 7 *Pseudomonas aeruginosa* | PEG-10-2-61 | | 16 | 32 | 8 | 32 | 32 |
| 8 *Staphylococcus aureus* | ATCC 29213 | 6.60E+05 | 0.5 | 8 | 0.5 | 32 | 32 |
| | | | 0.12-0.5 | n.a. | n.a. | n.a. | n.a. |
| 9 *Staphylococcus aureus* | PEG 10-38-22 | | 32 | 32 | 2 | 32 | 32 |
| 10 *Escherichia coli* | PEG 10-2-81 | | 32 | 0.5 | 0.063 | 32 | 32 |
| 11 *Escherichia coli* | PEG 10-79-22 | | 32 | 0.25 | 0.063 | 32 | 32 |
| 12 *Klebsiella pneumoniae* | PEG-10-48-8 | | 32 | 32 | 32 | 32 | 32 |
| 13 *Klebsiella pneumoniae* | PEG-10-75-61 | 4.00E+05 | 32 | 32 | 32 | 32 | 32 |
| 14 *Klebsiella pneumoniae* | 310-1-54 | | 32 | 32 | 32 | 32 | 32 |
| 15 *Klebsiella oxytoca* | PEG-10-75-18 | | 0.125 | 32 | 8 | 32 | 32 |
| 16 *Klebsiella oxytoca* | PEG-10-45-54 | 4.40E+05 | 0.031 | 4 | 0.5 | 32 | 32 |
| 17 *Enterobacter cloacae* | PEG-10-52-78 | | 16 | 32 | 32 | 32 | 32 |
| 18 *Enterobacter aerogenes* | 220-1-22 | | 0.25 | 32 | 4 | 32 | 32 |
| 19 *Enterobacter asburiae* | PEG-13-74-62 | 8.20E+05 | 0.063 | 32 | 32 | 32 | 32 |
| 20 *Pseudomonas aeruginosa* | PEG-10-47-57 | | 16 | 8 | 4 | 32 | 32 |
| 21 *Pseudomonas aeruginosa* | PEG-10-44-76 | | 0.125 | 4 | 0.5 | 32 | 32 |
| 22 *Acinetobacter baumannii* | PEG 10-12-26 | | 16 | 16 | 16 | 32 | 32 |

TABLE 2-continued

ATCC strains were obtained from the American Type Culture Collection (ATCC). PEG-strains are clinical isolates that were collected during a study of the Paul-Ehrlich-Society for Chemotherapie e.V. (PEG) in 2010 and 2013/14.The strains without any further designations such as 100-2-49 are further clinical isolates obtained from a lab in Germany.

| | | | | MHK [mg/l] | | | |
|---|---|---|---|---|---|---|---|
| Nr. | Strain | | KBE/ml | CIP | Compound 1 | Compound 3 | Compound 2 | Compound 16 |
| 23 | *Acinetobacter baumannii* | PEG 10-57-31 | 2.60E+05 | 32 | 32 | 32 | 32 | 32 |
| 24 | *Acinetobacter baumannii* | PEG 10-57-24 | | 0.125 | 2 | 1 | 32 | 32 |
| 25 | *Acinetobacter baumannii* | PEG 10-86-5 | 2.00E+05 | 0.125 | 4 | 4 | 32 | 32 |
| 26 | *Staphylococcus aureus* | PEG 13-18-19 | | 0.5 | 8 | 0.5 | 32 | 32 |
| 27 | *Staphylococcus aureus* | PEG 13-71-26 | | 0.125 | 4 | 0.125 | 32 | 32 |
| 28 | *Enterococcus faecium* | PEG 13-9-13 | | 32 | 32 | 8 | 32 | 32 |
| 29 | *Enterococcus faecium* | PEG 13-17-59 | | 32 | 32 | 8 | 32 | 32 |
| 30 | *Enterococcus faecium* | PEG 13-73-65 | | 32 | 32 | 8 | 32 | 32 |

The invention claimed is:

1. A compound having a modular structure as defined by formula (1):

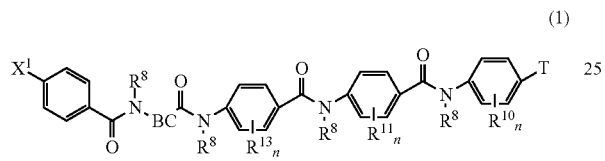
(1)

a) with BC being selected from:

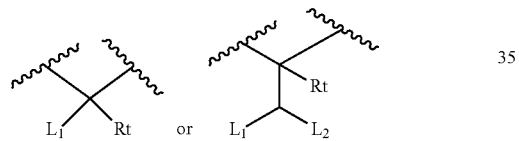

with $L_1$ being a substituted or unsubstituted aromatic heterocycle or a substituted or unsubstituted non-aromatic heterocycle with Rt being selected from H or $C_1$-$C_4$ alkyl, or with $L_1$ and Rt forming a non-aromatic heterocycle, which is optionally substituted, with $L_2$ being —H, b) with $X^1$ being BA-CONR$^8$— with BA being selected from:

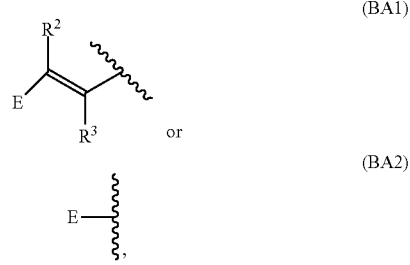
(BA1)

(BA2)

with $R^2$ and $R^3$ being selected independently from each other from —H, —F, —CN, —OH, a substituted or unsubstituted $C_1$-$C_3$ alkyl, a substituted or unsubstituted $C_1$-$C_3$ alkoxy or a $C_1$-$C_3$ haloalkyl, with E being:
a substituted or unsubstituted $C_1$-$C_{16}$ alkyl, a substituted or unsubstituted $C_2$-$C_{16}$ alkenyl, a substituted or unsubstituted $C_2$-$C_{16}$ alkynyl, or a substituted or unsubstituted $C_3$-$C_{10}$ cycloalkyl,
a substituted or unsubstituted $C_3$-$C_{10}$ heterocycle,
a substituted or unsubstituted $C_5$-$C_{10}$ heteroaryl, or
a substituted or unsubstituted $C_6$-$C_{10}$ aryl,
wherein at least one optional substituent is hydroxy or halogen;

c) with each $R^8$ being —H, or $C_1$-$C_4$ alkyl, optionally substituted with one or more F, d) with n of $R^{10}{}_n$ and n of $R^{11}{}_n$ being independently from each other 0, 1, 2, 3 or 4,
with each $R^{10}$ and $R^{11}$ being selected independently from any other $R^{10}$ and $R^{11}$ from:
—OH, —F, —Cl, —Br, —I, —CCH, —CN, —N$_3$, or —O$C_1$-$C_6$ alkyl, optionally substituted with OH or F; or
OCF$_3$, —NH$_2$, —NHCH$_3$, —N(CH$_3$)$_2$, —$C_1$-$C_6$ alkyl; —(CH$_2$)m-OR$_a$, —CHCH$_2$, —CH$_2$OH, —SO$_2$NH$_2$, —SO$_2$N(CH$_3$)$_2$, —SO$_2$NHCH$_3$, —CH$_3$, —CF$_3$, —NO$_2$, —O—PO$_3$H$_2$, —O—PO$_3$R$_a$H, or —O—PO$_3$ (R$_a$)$_2$, —OCH$_3$, —OC$_2$H$_5$, —O-i-C$_3$H$_7$, or —O-n-C$_3$H$_7$, with $R_a$ being selected from:
hydrogen,
a substituted or unsubstituted $C_1$-$C_{16}$ alkyl, a substituted or unsubstituted $C_2$-$C_{16}$ alkenyl, a substituted or unsubstituted $C_2$-$C_{16}$ alkynyl, or a $C_1$-$C_{16}$ haloalkyl, or
a substituted or unsubstituted $C_3$-$C_{10}$ cycloalkyl or a substituted or unsubstituted $C_3$-$C_{10}$ halo cycloalkyl;
with m being selected from 0, 1 or 2, e) with T being selected from:
CO$_2$H, —SO$_3$H, —C(=O)OR$_a$ or —CON(R$_a$)$_2$
with $R_a$ having the above meaning, f) with n of $R^{13}{}_n$ being 0, 1, 2, 3 or 4, and
with each $R^{13}$ being selected independently from any other $R^{13}$ from —OH, substituted or unsubstituted $C_1$-$C_6$ alkyl or substituted or unsubstituted $C_1$-$C_6$ alkoxy.

2. The compound according to claim 1, wherein moiety $L_1$ is a five membered or six membered aromatic heterocycle or 3-7 membered non-aromatic heterocycle, that may be substituted or unsubstituted.

3. The compound according to claim 1, wherein $L_1$ is a five membered aromatic N-heterocycle selected from a group consisting of substituted or unsubstituted:

pyrroles, imidazoles, pyrazoles, triazoles, tetrazoles;
pyrazolone;
thiadiazoles; and
isoxazoles, oxazoles, and oxadiazoles.

4. The compound according to claim 1, wherein $L_1$ is a five membered non-aromatic N-heterocycle selected from a group consisting of substituted or unsubstituted:
pyrrolidines, pyrazolidines, hydantoines, imidazolidinones, isoxazolidines, oxazolidinones, isothiazolidines, and isothiazolinone.

5. The compound according to claim 1, wherein $L_1$ is a six membered aromatic N-heterocycle selected from a group consisting of substituted or unsubstituted pyridines, pyridazines, pyrimidines, pyrazines, triazines and tetrazines.

6. The compound according to claim 1, wherein $L_1$ is a six membered non-aromatic N heterocycle selected from a group consisting of substituted or unsubstituted piperidines and piperazines.

7. The compound according to claim 1, having a modular structure as defined by the formula (2):

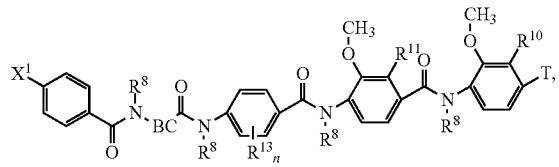

(2)

wherein $X^1$, BC, $R^8$, $R^{11}$, $R^{10}$, $R^{13}$ and T have the meaning defined in claim 1.

8. The compound according to claim 1, wherein:
$X^1$ is BA-CONHR$^8$—, with BA being BA1, with $R^2$ and $R^3$ having the meaning defined in claim 1, and with E being:

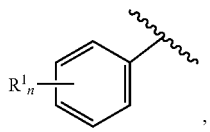

, with n of $R^1_n$ being 0, 1, 2, 3, 4 or 5, and
with each $R^1$ independently from any other $R^1$ being selected from:
OH, —F, —C$_1$, —Br, I, —CCH, —CN, —N$_3$, —OCH$_3$, —OC$_2$H$_5$, —OC$_3$H$_7$, —O-i-Pr, —OCF$_3$, —NH$_2$, —NHCH$_3$, —N(CH$_3$)$_2$, —CH$_3$, —CH$_2$—CH$_3$, —CF$_3$, —OCONH$_2$, —NO$_2$, —OCH$_2$O—, —O—PO$_3$H$_2$, —O—PO$_3$R$_a$H, —O—PO$_3$ (R$_a$)$_2$ or —(CH$_2$)$_m$—OR$_a$, with m and R$_a$ having the meaning defined in claim 1.

9. The compound according to claim 1, wherein:
n of $R^{10}_n$ and n of $R^{11}_n$ are 0, 1, 2, 3 or 4, and with each $R^{10}$ and with each $R^{11}$ independently from any other $R^{10}$ being selected from —OH, —F, —OCH$_3$, —OC$_2$H$_5$, —OC$_3$H$_7$, —OCF$_3$, —CF$_3$ or —(CH$_2$)$_m$—OR$_a$,
with R$_a$ being selected from hydrogen, —CH$_3$, —CH$_2$CH$_3$, —CH$_2$CH$_2$CH$_3$, —CH$_2$CH$_2$CH$_2$CH$_3$, —CH(CH$_3$)$_2$, —CH$_2$CH(CH$_3$)$_2$, or —C(CH$_3$)$_3$, with m being selected from 1 or 2.

10. The compound according to claim 1, wherein:
T is —CO$_2$H, —SO$_3$H, —C(=O) OR$_a$ or —CONR$_a$, with R$_a$ being selected from hydrogen, —CH$_3$, —CH$_2$CH$_3$, —CH$_2$CH$_2$CH$_3$, —CH$_2$CH$_2$CH$_2$CH$_3$, —CH(CH$_3$)$_2$, —CH$_2$CH(CH$_3$)$_2$, or —C(CH$_3$)$_3$.

11. A compound having a modular structure as defined by formula (9):

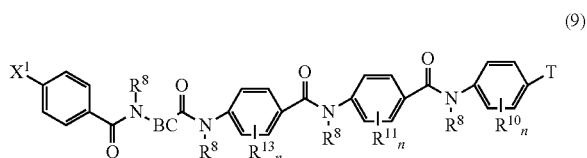

(9)

wherein BC is selected from:

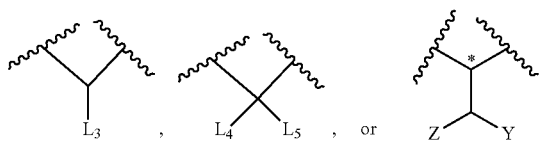

$L_3$, $L_4$ being selected independently from each other from
—H, —CH$_3$, —CH$_2$CH$_2$CH$_2$NHC(NR$^c$)N(R$^b$)(R$^a$), —CH$_2$CON(R$^b$)(R$^a$), —CH$_2$C(=O)OR$^a$, —CH$_2$SR$^a$, —CH$_2$CH$_2$C(=O)N(R$^b$)(R$^a$), —CH$_2$CH$_2$C(=O)OR$^a$, —CH$_2$(C$_3$H$_3$N$_2$), —CH$_2$CH$_2$CH$_2$NH$_2$, —CH$_2$CH$_2$SCH$_3$, —CH$_2$(C$_6$H$_5$), —CH$_2$CH$_2$CH$_2$—, —CH$_2$OR$^a$, —CH(OR$^a$)CH$_3$, —CH$_2$(C$_8$H$_6$N)OR$^a$, —CH$_2$(C$_6$H$_4$)OR$^a$, —CH(CH$_3$)$_2$, —CCH, —CN, —OCH$_3$, —CF$_3$, —R$^a$, —CH(R$^b$)(R$^a$), —CH$_2$C(=O) R$^a$, —C(=O)OR$^a$, —OC(=O)NR$^b$R$^a$, —C(=O) NR$^b$R$^a$, —CH$_2$C(=O)NR$^b$ (OR$^a$), —CH$_2$S(O$_2$)R$^a$, —S(O$_2$)OR$^a$, —CH$_2$S(O$_2$)OR$^a$, —CH$_2$NR$^b$C(=O)R$^a$, —CH$_2$NR$^b$S(O$_2$)R$^a$, —CH$_2$P(=O)(OR$^b$)(OR$^a$), —CH$_2$P(=O)(OR$^b$)(R$^a$), —CH$_2$P(=O)(R$^b$)(R$^a$) or —CH$_2$S(O$_2$)NR$^b$R$^a$, and
with R$^a$, R$^b$, and R$^c$ being selected independently from each other from:
a substituted or unsubstituted C$_1$-C$_4$ alkyl, a substituted or unsubstituted C$_1$-C$_4$ alkoxy, a substituted or unsubstituted C$_1$-C$_4$ carboxy, a substituted or unsubstituted C$_2$-C$_4$ alkenyl, a substituted or unsubstituted C$_2$-C$_4$ alkynyl, or a C$_1$-C$_4$ haloalkyl, or
a substituted or unsubstituted C$_3$-C$_{10}$ cycloalkyl or a substituted or unsubstituted C$_3$-C$_{10}$ halo cycloalkyl, or
a substituted or unsubstituted C$_3$-C$_{10}$ heterocycle or a substituted or unsubstituted C$_3$-C$_{10}$ halo heterocycle, or
a substituted or unsubstituted C$_5$-C$_{10}$ heteroaryl, or
a substituted or unsubstituted C$_6$-C$_{10}$ aryl,
with $L_5$ being selected from —CH$_3$, —CH$_2$CH$_3$, —OCH$_3$, —OCH$_2$CH$_3$, a C$_1$-C$_2$-fluoro alkyl, or —NH$_2$;
with Y being —CN, —C(=O)OH, —C(=O)OCH$_3$, —C(=O)OCH$_2$CH$_3$, —C(=O)NHCH$_3$, —C(=O) NHCH$_2$CH$_3$, —C(=O)N(CH$_3$)$_2$, —C(=O)N (CH$_2$CH$_3$)$_2$, —C(=O)N(CH$_3$)(CH$_2$CH$_3$) or —C(=O) NH$_2$,
with Z being —H, —OH, —CH$_3$, —CH$_2$CH$_3$, —OCH$_3$, —NH$_2$, —NHCH$_3$, —N(CH$_3$)$_2$ or, —N(CH$_3$)$_3^+$, with n of $R^{13}{}_n$ being 1, 2, 3 or 4,
with $X^1$ being BA-CONR$^8$— with BA being selected from:

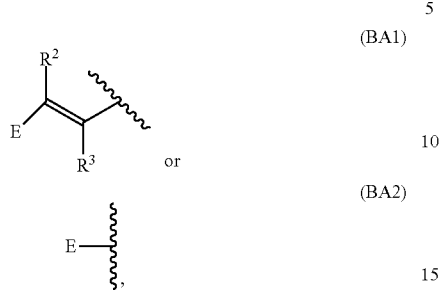

with $R^2$ and $R^3$ being selected, independently from each other from —H, —F, —CN, —OH, a substituted or unsubstituted $C_1$-$C_3$ alkyl, a substituted or unsubstituted $C_1$-$C_3$ alkoxy or a $C_1$-$C_3$ haloalkyl,
with E being:
a substituted or unsubstituted $C_1$-$C_{16}$ alkyl, a substituted or unsubstituted $C_2$-$C_{16}$ alkenyl, a substituted or unsubstituted $C_2$-$C_{16}$ alkynyl, or a substituted or unsubstituted $C_3$-$C_{10}$ cycloalkyl,
a substituted or unsubstituted $C_3$-$C_{10}$ heterocycle,
a substituted or unsubstituted $C_5$-$C_{10}$ heteroaryl, or
a substituted or unsubstituted $C_6$-$C_{10}$ aryl,
wherein at least one optional substituent is hydroxy or halogen:
c) with each $R^8$ being —H, or $C_1$-$C_4$ alkyl, optionally substituted with one or more F,
d) with n of $R^{10}{}_n$ and n of $R^{11}{}_n$ being independently from each other 0, 1, 2, 3 or 4,
with each $R^{10}$ and $R^{11}$ being selected independently from any other $R^{10}$ and $R^{11}$ from:
—OH, —F, —C$_1$, —Br, —I, —CCH, —CN, —N$_3$, or —OC$_1$-C$_6$ alkyl, optionally substituted with OH or F; or
—OCF$_3$, —NH$_2$, —NHCH$_3$, —N(CH$_3$)$_2$, —C$_1$-C$_6$ alkyl, —(CH$_2$)m-OR$^a$, —CHCH$_2$, —CH$_2$OH, —SO$_2$NH$_2$, —SO$_2$N(CH$_3$)$_2$, —SO$_2$NHCH$_3$, —CH$_3$, —CF$_3$, —NO$_2$, —O—PO$_3$H$_2$, —O—PO$_3$R$_a$H, —O—PO$_3$(Ra)$_2$, —OCH$_3$, —OC$_2$H$_5$, —O-i-C$_3$H$_7$, or —O-n-C$_3$H$_7$, with $R^a$ being selected from:
hydrogen,
a substituted or unsubstituted $C_1$-$C_{16}$ alkyl, a substituted or unsubstituted $C_2$-$C_{16}$ alkenyl, a substituted or unsubstituted $C_2$-$C_{16}$ alkynyl, or a $C_1$-$C_{16}$ haloalkyl, or
a substituted or unsubstituted $C_3$-$C_{10}$ cycloalkyl or a substituted or unsubstituted $C_3$-$C_{10}$ halo cycloalkyl:
with m being selected from 0, 1 or 2,
e) with T being selected from:
CO$_2$H, —SO$_3$H, —C(=O)OR$^a$ or —CON(R$^a$)$_2$
with $R_a$ having the above meaning,
f) with each $R^{13}$ being selected independently from any other $R^{13}$ from —OH, substituted or unsubstituted —C$_1$-C$_6$ alkyl or substituted or unsubstituted C$_1$-C$_6$ alkoxy.

12. The compound according to claim 11, wherein BC is selected from:
$L^3$, $L^4$ being selected independently from each other from —H, —CH$_3$, —CH$_2$CH$_2$CH$_2$NHC(NR$^c$)N(R$^b$)(R$^a$), —CH$_2$CON(R$^b$)(R$^a$), —CH$_2$C(=O)OR$^a$, —CH$_2$SR$^a$, —CH$_2$CH$_2$C(=O)N(R$^b$)(R$^a$), —CH$_2$CH$_2$C(=O)OR$^a$, —CH$_2$(C$_3$H$_3$N$_2$), —CH$_2$CH$_2$CH$_2$NH$_2$, —CH$_2$CH$_2$SCH$_3$, —CH$_2$(C$_6$H$_5$), —CH$_2$OR$^a$, —CH(OR$^a$)CH$_3$, —CH$_2$(C$_8$H$_6$N)OR$^a$, —CH$_2$(C$_6$H$_4$)OR$^a$, —CH(CH$_3$)$_2$, —CN, —OCH$_3$, —CH(R$^b$)(R$^a$), —CH$_2$C(=O)R$^a$, —C(=O)OR$^a$, —OC(=O)NR$^b$R$^a$, —C(=O)NR$^b$R$^a$, —CH$_2$C(=O)NR$^b$ (OR$^a$), or —CH$_2$NR$^b$C(=O)R$^a$,
$L^5$ being selected from —CH$_3$, —CH$_2$CH$_3$, —OCH$_3$, —OCH$_2$CH$_3$, or —NH$_2$; and
Z being H and Y being CN or —C(=O)NH$_2$.

13. A method of treatment of a bacterial infection in an individual, comprising administering the compound according to claim 1, wherein the bacterial infection is caused by one of the following bacterial strains: E. coli, S. typhimurium; Bacillus subtilis, Micrococcus luteus, Klebsiella pneumoniae, Pseudomonas aeruginosa, Staphylococcus aureus, Klebsiella oxytoca, Enterobacter cloacae, Enterobacter aerogenes, Enterobacter asburiae, Acinetobacter baumannii, Enterococcus faecium.

14. A compound having the structure:

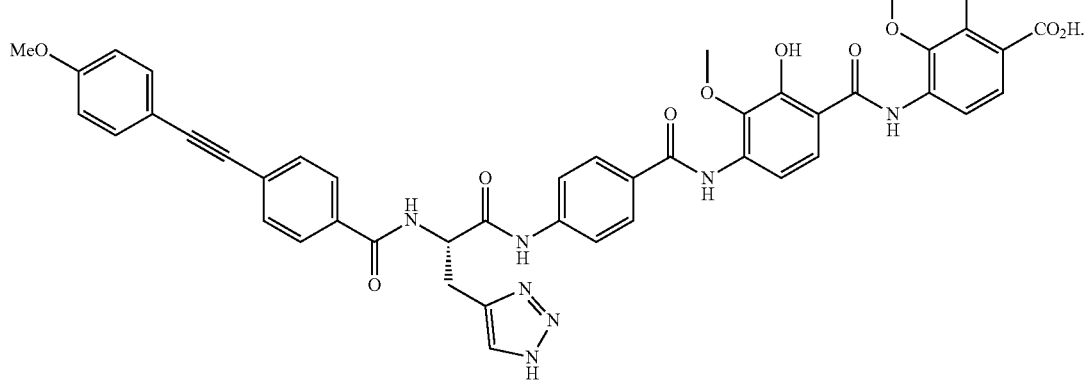

15. The compound of claim 1, wherein at least one of:
the $L_1$ and Rt forming a non-aromatic N-heterocyclic ring, which is optionally substituted;
$R^2$ and $R^3$ being selected independently from each other from —H, —F, —CN, —OH, a substituted or unsubstituted $C_1$-$C_3$ alkyl, a substituted or unsubstituted $C_1$-$C_3$ alkoxy or a $C_1$-$C_3$ haloalkyl;

E being a substituted or unsubstituted $C_1$-$C_8$ alkyl, a substituted or unsubstituted $C_2$-$C_8$ alkenyl, a substituted or unsubstituted $C_2$-$C_8$ alkynyl, a substituted or unsubstituted $C_3$-$C_{10}$ cycloalkyl;

each $R^8$ being selected independently from each other from H or $CH_3$;

n of $R^{10}{}_n$ and n of $R^{11}{}_n$ being 0, 1, 2 or 3;

each $R^{10}$ and $R^{11}$ being selected independently from any other $R^{10}$ and $R^{11}$ from —$OCF_3$, —$NH_2$, —$NHCH_3$, —$N(CH_3)_2$, —$C_1$-$C_6$ alkyl, —$CH_3$, —$CH_2CH_3$, —$(CH_2)$m-$OR^a$, —$CHCH_2$, —$CH_2OH$, —$SO_2NH_2$, —$SO_2N(CH_3)_2$, —$SO_2NHCH_3$, —$CF_3$, —$NO_2$, —O—$PO_3H_2$, —O—$PO_3R_aH$ or —O—$PO_3(R_a)_2$;

m being selected from 0 or 1;

n of $R^{13}{}_n$ being 0, 1, 2 or 3; or each $R^{13}$ being selected independently from any other $R^{13}$ from —OH or —$OCH_3$.

16. The compound of claim 1, wherein at least one of:

$L_1$ is a five membered or six membered aromatic N-heterocycle or non-aromatic N heterocycle that may be substituted or unsubstituted;

$R^2$ and $R^3$ being selected independently from each other from —H, —F, —CN, —OH, —$CH_3$, —$CH_2CH_3$, —$OCH_3$, —$OCH_2CH_3$, —$OCH_2CH_2CH_3$, —$OCH(CH_3)_2$, —$OCF_3$, —$CH_2CF_3$, —$CHFCF_3$, —$CF_2CF_3$, —$CHF_2$, —$CH_2F$ or —$CF_3$;

E being a substituted or unsubstituted $C_4$-$C_{10}$ heterocycle;

$R^8$ being H; or each $R^{10}$ and $R^{11}$ being selected independently from any other $R^{10}$ and $R^{11}$ from —OH, —F, —$OCH_3$, —$OC_2H_5$, —O-i-$C_3H_7$, —O-n-$C_3H_7$, —$OCF_3$ or —$CF_3$.

17. The compound of claim 1, wherein at least one of:

$R^2$ and $R^3$ being selected independently from each other from —H, —F, —$OCH_3$ or —$CH_3$; or $L_1$ is 1,2,4-triazol-3-one, imidazolones, pyrrolidones, 1,3,4-thiadiazoles, thiazoles, isothiazoles, or thiazolidinediones, substituted or unsubstituted.

18. The compound of claim 11, wherein at least one of:

$R^2$ and $R^3$ being selected independently from each other from —H, —F, —CN, —OH, a substituted or unsubstituted $C_1$-$C_3$ alkyl, a substituted or unsubstituted $C_1$-$C_3$ alkoxy or a $C_1$-$C_3$ haloalkyl;

E being a substituted or unsubstituted $C_1$-$C_8$ alkyl, a substituted or unsubstituted $C_2$-$C_8$ alkenyl, a substituted or unsubstituted $C_2$-$C_8$ alkynyl or a substituted or unsubstituted $C_3$-$C_{10}$ cycloalkyl;

each $R^8$ being selected independently from each other from H or $CH_3$;

n of $R^{10}{}_n$ and n of $R^{11}{}_n$ being 0, 1, 2 or 3;

each $R^{10}$ and $R^{11}$ being selected independently from any other $R^{10}$ and $R^{11}$ from —$OCF_3$, —$NH_2$, —$NHCH_3$, —$N(CH_3)_2$, —$C_1$-$C_6$ alkyl, —$CH_3$, —$CH_2CH_3$, —$(CH_2)$m-$OR^a$, —$CHCH_2$, —$CH_2OH$, —$SO_2NH_2$, —$SO_2N(CH_3)_2$, —$SO_2NHCH_3$, —$CH_3$, —$CF_3$, —$NO_2$, —O—$PO_3H_2$, —O—$PO_3R_aH$ or —O—$PO_3(R_a)_2$;

m being selected from 0 or 1;

n of $R^{13}{}_n$ being 0, 1, 2 or 3; or each $R^{13}$ being selected independently from any other $R^{13}$ from —OH or —$OCH_3$.

19. The compound of claim 11, wherein at least one of:

$R^2$ and $R^3$ being selected independently from each other from —H, —F, —CN, —OH, —$CH_3$, —$CH_2CH_3$, —$OCH_3$, —$OCH_2CH_3$, —$OCH_2CH_2CH_3$, —$OCH(CH_3)_2$, —$OCF_3$, —$CH_2CF_3$, —$CHFCF_3$, —$CF_2CF_3$, —$CHF_2$, —$CH_2F$ or —$CF_3$;

E being a substituted or unsubstituted $C_4$-$C_{10}$ heterocycle;

$R^8$ being H; or each $R^{10}$ and $R^{11}$ being selected independently from any other $R^{10}$ and $R^{11}$ from —OH, —F, —$OCH_3$, —$OC_2H_5$, —O-i-$C_3H_7$, —O-n-$C_3H_7$, —$OCF_3$ or —$CF_3$.

20. The compound of claim 11, wherein $R^2$ and $R^3$ being selected independently from each other from —H, —F, —$OCH_3$ or —$CH_3$.

* * * * *